(12) United States Patent
Gupta et al.

(10) Patent No.: US 11,255,839 B2
(45) Date of Patent: Feb. 22, 2022

(54) APPARATUS AND METHODS FOR ANALYTE SENSOR MISMATCH CORRECTION

(71) Applicant: GlySens Incorporated, San Diego, CA (US)

(72) Inventors: Piyush Gupta, San Diego, CA (US); Joseph Lucisano, San Diego, CA (US)

(73) Assignee: GLYSENS INCORPORATED, San Diego, CA (US)

( * ) Notice: Subject to any disclaimer, the term of this patent is extended or adjusted under 35 U.S.C. 154(b) by 183 days.

(21) Appl. No.: 16/233,536

(22) Filed: Dec. 27, 2018

(65) Prior Publication Data

US 2019/0212323 A1  Jul. 11, 2019

Related U.S. Application Data

(60) Provisional application No. 62/613,695, filed on Jan. 4, 2018.

(51) Int. Cl.
*G01N 33/49* (2006.01)
*G16C 20/20* (2019.01)
(Continued)

(52) U.S. Cl.
CPC ......... *G01N 33/4925* (2013.01); *A61B 5/076* (2013.01); *A61B 5/1468* (2013.01);
(Continued)

(58) Field of Classification Search
None
See application file for complete search history.

(56) References Cited

U.S. PATENT DOCUMENTS 2,508,523 A   5/1950   Eduard et al.
2,563,062 A   8/1951   Perley et al.
(Continued)

FOREIGN PATENT DOCUMENTS

AU   2016382976 A1   8/2018
AU   2017201943 B2   10/2018
(Continued)

OTHER PUBLICATIONS

Alvarez-Icaza M., et al., "Mass Production of Biosensors," Analytical Chemistry, 1993, vol. 65 (11), pp. 525-533.
(Continued)

*Primary Examiner* — Xiaoyun R Xu
(74) *Attorney, Agent, or Firm* — Gazdzinski & Associates, PC

(57) ABSTRACT

Apparatus and methods for response modeling and correction of signals associated with a parameter sensor. In one exemplary embodiment, the parameter sensor is configured to measure a physiologic analyte of a living being (e.g., blood glucose), and the apparatus and methods employ a mathematical transformation of two or more sensing elements (electrodes) of the sensor in order to compensate for temporal response differences or "mismatch." This compensation enables the calculated blood analyte level, which results from processing of the signals of the two or more sensing electrodes, to be more accurate than calculations made without such compensation. In one variant, the parameter signals are generated, and compensation processing conducted, autonomously via a common implanted sensor platform.

22 Claims, 21 Drawing Sheets

(51) Int. Cl.
*A61B 5/1468* (2006.01)
*A61B 5/1473* (2006.01)
*G16H 10/40* (2018.01)
*A61B 5/07* (2006.01)
*A61B 5/145* (2006.01)

(52) U.S. Cl.
CPC ........ *A61B 5/1473* (2013.01); *A61B 5/14532* (2013.01); *G16C 20/20* (2019.02); *G16H 10/40* (2018.01)

(56) References Cited

U.S. PATENT DOCUMENTS

| | | | |
|---|---|---|---|
| 2,805,191 A | 9/1957 | Paul et al. | |
| 2,864,750 A | 12/1958 | Hughes, Jr. et al. | |
| 2,998,371 A | 8/1961 | Sabins et al. | |
| 3,099,575 A | 7/1963 | Hill et al. | |
| 3,246,235 A | 4/1966 | James et al. | |
| 3,249,250 A | 5/1966 | McKee et al. | |
| 3,300,345 A | 1/1967 | Lyons, Jr. et al. | |
| 3,308,046 A | 3/1967 | Suleski et al. | |
| 3,458,421 A | 7/1969 | Dahms et al. | |
| 3,505,195 A | 4/1970 | Nielsen et al. | |
| 3,542,662 A | 11/1970 | Hicks et al. | |
| 3,616,412 A | 10/1971 | Gnage et al. | |
| 3,957,613 A | 5/1976 | Macur et al. | |
| 4,036,716 A | 7/1977 | Hulthe et al. | |
| 4,088,550 A | 5/1978 | Malkin et al. | |
| 4,240,438 A | 12/1980 | Shults et al. | |
| 4,306,952 A | 12/1981 | Jansen et al. | |
| 4,340,457 A | 7/1982 | Kater et al. | |
| 4,361,153 A | 11/1982 | Slocum et al. | |
| 4,366,033 A | 12/1982 | Richter et al. | |
| 4,431,004 A | 2/1984 | Bessman et al. | |
| 4,458,686 A | 7/1984 | Clark, Jr. | |
| 4,484,987 A | 11/1984 | Gough et al. | |
| 4,494,950 A | 1/1985 | Fischell | |
| 4,541,431 A | 9/1985 | Ibrahim et al. | |
| 4,550,732 A | 11/1985 | Batty, Jr. et al. | |
| 4,553,547 A | 11/1985 | Keimel | |
| 4,571,589 A | 2/1986 | Slocum et al. | |
| 4,637,861 A | 1/1987 | Krull et al. | |
| 4,650,547 A | 3/1987 | Gough et al. | |
| 4,671,288 A | 6/1987 | Gough | |
| 4,703,756 A | 11/1987 | Gough et al. | |
| 4,746,218 A | 5/1988 | Lord, III | |
| 4,748,562 A | 5/1988 | Miller et al. | |
| 4,759,828 A | 7/1988 | Young et al. | |
| 4,781,798 A | 11/1988 | Gough | |
| 4,830,713 A | 5/1989 | Gagescu | |
| 4,890,620 A | 1/1990 | Gough et al. | |
| 5,042,902 A | 8/1991 | Huebscher et al. | |
| 5,046,242 A | 9/1991 | Kuzma et al. | |
| 5,077,476 A | 12/1991 | Rosenthal | |
| 5,105,811 A | 4/1992 | Kuzma et al. | |
| 5,112,455 A | 5/1992 | Cozzette et al. | |
| 5,150,516 A | 9/1992 | Boero et al. | |
| 5,165,406 A | 11/1992 | Wong | |
| 5,189,717 A | 2/1993 | Larson et al. | |
| 5,264,103 A | 11/1993 | Yoshioka et al. | |
| 5,272,283 A | 12/1993 | Kuzma et al. | |
| 5,273,203 A | 12/1993 | Webster et al. | |
| 5,283,104 A | 2/1994 | Aoude et al. | |
| 5,283,204 A | 2/1994 | Rhodes et al. | |
| 5,284,140 A | 2/1994 | Allen et al. | |
| 5,322,063 A | 6/1994 | Allen et al. | |
| 5,337,475 A | 8/1994 | Aoude et al. | |
| 5,395,504 A | 3/1995 | Saurer et al. | |
| 5,431,160 A | 7/1995 | Wilkins | |
| 5,487,855 A | 1/1996 | Moeggenborg et al. | |
| 5,497,772 A | 3/1996 | Schulman et al. | |
| 5,560,098 A | 10/1996 | Robins et al. | |
| 5,660,163 A | 8/1997 | Schulman et al. | |
| 5,692,299 A | 12/1997 | Daems et al. | |
| 5,695,623 A | 12/1997 | Michel et al. | |
| 5,711,861 A | 1/1998 | Ward et al. | |
| 5,727,283 A | 3/1998 | Webster | |
| 5,741,330 A | 4/1998 | Brauker et al. | |
| 5,750,926 A | 5/1998 | Schulman et al. | |
| 5,776,324 A | 7/1998 | Usala | |
| 5,777,060 A | 7/1998 | Van Antwerp | |
| 5,782,755 A | 7/1998 | Chance et al. | |
| 5,782,891 A | 7/1998 | Hassler et al. | |
| 5,791,344 A | 8/1998 | Schulman et al. | |
| 5,804,048 A | 9/1998 | Wong et al. | |
| 5,821,011 A | 10/1998 | Taylor et al. | |
| 5,842,983 A | 12/1998 | Abel et al. | |
| 5,855,995 A | 1/1999 | Haq et al. | |
| 5,864,088 A | 1/1999 | Sato et al. | |
| 5,882,494 A | 3/1999 | Van Antwerp | |
| 5,887,240 A | 3/1999 | Fournier et al. | |
| 5,932,175 A | 8/1999 | Knute et al. | |
| 5,942,842 A | 8/1999 | Fogle, Jr. et al. | |
| 5,964,993 A | 10/1999 | Blubaugh, Jr. et al. | |
| 5,985,129 A | 11/1999 | Gough et al. | |
| 6,001,067 A | 12/1999 | Shults et al. | |
| 6,027,479 A | 2/2000 | Alei et al. | |
| 6,041,496 A | 3/2000 | Haq et al. | |
| 6,081,736 A | 6/2000 | Colvin et al. | |
| 6,090,503 A | 7/2000 | Taylor et al. | |
| 6,096,066 A | 8/2000 | Chen et al. | |
| 6,107,083 A | 8/2000 | Collins et al. | |
| 6,119,208 A | 9/2000 | White et al. | |
| 6,175,752 B1 | 1/2001 | Say et al. | |
| 6,193,421 B1 | 2/2001 | Tamekuni et al. | |
| 6,200,772 B1 | 3/2001 | Vadgama et al. | |
| 6,212,416 B1 | 4/2001 | Ward et al. | |
| 6,221,513 B1 | 4/2001 | Lasater et al. | |
| 6,403,944 B1 | 6/2002 | MacKenzie et al. | |
| 6,466,810 B1 | 10/2002 | Ward et al. | |
| 6,516,808 B2 | 2/2003 | Schulman et al. | |
| 6,551,252 B2 | 4/2003 | Sackner et al. | |
| 6,558,321 B1 | 5/2003 | Burd et al. | |
| 6,642,015 B2 | 11/2003 | Vachon et al. | |
| 6,721,587 B2 | 4/2004 | Gough et al. | |
| 6,741,877 B1 | 5/2004 | Shults et al. | |
| 6,809,607 B2 | 10/2004 | Nagasaka | |
| 6,812,404 B1 | 11/2004 | Martinez et al. | |
| 6,832,114 B1 | 12/2004 | Whitehurst et al. | |
| 6,843,107 B2 | 1/2005 | Newman et al. | |
| 6,931,268 B1 | 8/2005 | Kiani-Azarbayjany et al. | |
| 7,005,796 B2 | 2/2006 | Kolluri et al. | |
| 7,079,881 B2 | 7/2006 | Schulman et al. | |
| 7,106,939 B2 | 9/2006 | LaBrake et al. | |
| 7,110,803 B2 | 9/2006 | Shults et al. | |
| 7,134,999 B2 | 11/2006 | Brauker et al. | |
| 7,136,689 B2 | 11/2006 | Shults et al. | |
| 7,140,787 B2 | 11/2006 | Yamauchi et al. | |
| 7,146,203 B2 | 12/2006 | Botvinick et al. | |
| 7,161,727 B2 | 1/2007 | Callies et al. | |
| 7,189,341 B2 | 3/2007 | Li et al. | |
| 7,192,450 B2 | 3/2007 | Brauker et al. | |
| 7,226,978 B2 | 6/2007 | Tapsak et al. | |
| 7,248,912 B2 | 7/2007 | Gough et al. | |
| 7,323,142 B2 | 1/2008 | Pendo et al. | |
| 7,336,984 B2 | 2/2008 | Gough et al. | |
| 7,460,898 B2 | 12/2008 | Brister et al. | |
| 7,467,003 B2 | 12/2008 | Brister et al. | |
| 7,471,972 B2 | 12/2008 | Rhodes et al. | |
| 7,480,988 B2 | 1/2009 | Ok et al. | |
| 7,497,827 B2 | 3/2009 | Brister et al. | |
| 7,514,791 B2 | 4/2009 | Shah et al. | |
| 7,525,298 B2 | 4/2009 | Morgan et al. | |
| 7,761,130 B2 | 7/2010 | Simpson et al. | |
| 7,857,760 B2 | 12/2010 | Brister et al. | |
| 7,871,456 B2 | 1/2011 | Gough et al. | |
| 7,875,293 B2 | 1/2011 | Shults et al. | |
| 7,881,763 B2 | 2/2011 | Brauker et al. | |
| 7,894,870 B1 | 2/2011 | Lucisano et al. | |
| 8,133,178 B2 | 3/2012 | Brauker et al. | |
| 8,270,661 B2 | 9/2012 | Sorensen et al. | |
| 8,357,107 B2 | 1/2013 | Draudt et al. | |
| 8,690,820 B2 | 4/2014 | Cinar et al. | |
| 8,763,245 B1 | 7/2014 | Lucisano et al. | |

(56) References Cited

U.S. PATENT DOCUMENTS

| | | |
|---|---|---|
| 9,002,711 B2 | 4/2015 | Morinaka et al. |
| 9,119,528 B2 | 9/2015 | Cobelli et al. |
| 9,247,901 B2 | 2/2016 | Kamath et al. |
| 9,325,060 B2 | 4/2016 | Kalistaja et al. |
| 9,362,776 B2 | 6/2016 | Low et al. |
| 9,444,027 B2 | 9/2016 | Dibra et al. |
| 9,451,908 B2 | 9/2016 | Kamath et al. |
| 10,041,897 B2 | 8/2018 | Lucisano et al. |
| 10,638,979 B2 | 5/2020 | Gupta et al. |
| 10,736,553 B2 | 8/2020 | Lucisano et al. |
| 2002/0013613 A1 | 1/2002 | Haller et al. |
| 2002/0026108 A1 | 2/2002 | Colvin |
| 2002/0042561 A1 | 4/2002 | Schulman et al. |
| 2002/0123087 A1 | 9/2002 | Vachon et al. |
| 2002/0156355 A1 | 10/2002 | Gough |
| 2002/0161286 A1 | 10/2002 | Gerber et al. |
| 2002/0193671 A1 | 12/2002 | Ciurczak et al. |
| 2003/0048621 A1 | 3/2003 | Blood et al. |
| 2003/0049166 A1 | 3/2003 | Pendo et al. |
| 2003/0053784 A1 | 3/2003 | LaBrake et al. |
| 2003/0126593 A1 | 7/2003 | Mault |
| 2003/0179167 A1 | 9/2003 | Kolluri et al. |
| 2003/0181794 A1 | 9/2003 | Rini et al. |
| 2003/0187338 A1 | 10/2003 | Say et al. |
| 2003/0217966 A1 | 11/2003 | Tapsak et al. |
| 2003/0228681 A1 | 12/2003 | Ritts et al. |
| 2004/0011671 A1 | 1/2004 | Shults et al. |
| 2004/0012935 A1 | 1/2004 | Tagi et al. |
| 2004/0057043 A1 | 3/2004 | Newman et al. |
| 2004/0064133 A1 | 4/2004 | Miller et al. |
| 2004/0106857 A1 | 6/2004 | Gough |
| 2004/0158194 A1 | 8/2004 | Wolff et al. |
| 2004/0167080 A1 | 8/2004 | Dodge et al. |
| 2004/0176669 A1 | 9/2004 | Colvin et al. |
| 2004/0190111 A1 | 9/2004 | Callies et al. |
| 2004/0199059 A1 | 10/2004 | Brauker et al. |
| 2004/0211260 A1 | 10/2004 | Girmonsky |
| 2004/0220459 A1 | 11/2004 | Schlegel et al. |
| 2005/0027175 A1 | 2/2005 | Yang |
| 2005/0031689 A1 | 2/2005 | Shults et al. |
| 2005/0033132 A1 | 2/2005 | Shults et al. |
| 2005/0052858 A1 | 3/2005 | Shima et al. |
| 2005/0059871 A1 | 3/2005 | Gough et al. |
| 2005/0107677 A1 | 5/2005 | Ward et al. |
| 2005/0124873 A1 | 6/2005 | Shults et al. |
| 2005/0154271 A1 | 7/2005 | Rasdal et al. |
| 2005/0177036 A1 | 8/2005 | Shults et al. |
| 2005/0196322 A1 | 9/2005 | Truex et al. |
| 2005/0245799 A1 | 11/2005 | Brauker et al. |
| 2005/0245971 A1 | 11/2005 | Brockway et al. |
| 2005/0251083 A1 | 11/2005 | Carr-Brendel et al. |
| 2005/0272989 A1 | 12/2005 | Shah et al. |
| 2006/0020186 A1 | 1/2006 | Brister et al. |
| 2006/0074338 A1 | 4/2006 | Greenwald et al. |
| 2006/0085137 A1 | 4/2006 | Bartkowiak et al. |
| 2006/0086624 A1 | 4/2006 | Tapsak et al. |
| 2006/0195029 A1 | 8/2006 | Shults et al. |
| 2006/0200044 A1 | 9/2006 | Freeman et al. |
| 2006/0204536 A1 | 9/2006 | Shults et al. |
| 2006/0247736 A1 | 11/2006 | Roberts |
| 2006/0257995 A1 | 11/2006 | Simpson et al. |
| 2006/0257996 A1 | 11/2006 | Simpson et al. |
| 2006/0263763 A1 | 11/2006 | Simpson et al. |
| 2007/0151868 A1 | 7/2007 | Staib et al. |
| 2007/0173761 A1 | 7/2007 | Kanderian, Jr. et al. |
| 2008/0033269 A1 | 2/2008 | Zhang |
| 2008/0033272 A1 | 2/2008 | Gough et al. |
| 2008/0034972 A1 | 2/2008 | Gough et al. |
| 2008/0039702 A1 | 2/2008 | Hayter et al. |
| 2008/0086042 A1 | 4/2008 | Brister et al. |
| 2008/0132974 A1 | 6/2008 | Strother et al. |
| 2008/0197024 A1 | 8/2008 | Simpson et al. |
| 2008/0200791 A1 | 8/2008 | Simpson et al. |
| 2008/0317276 A1 | 12/2008 | Sorensen et al. |
| 2009/0055149 A1 | 2/2009 | Hayter et al. |
| 2009/0102678 A1 | 4/2009 | Mazza et al. |
| 2009/0131176 A1 | 5/2009 | Cheng et al. |
| 2009/0131776 A1 | 5/2009 | Simpson et al. |
| 2009/0182388 A1 | 7/2009 | Von Arx et al. |
| 2009/0221890 A1 | 9/2009 | Saffer |
| 2009/0240120 A1 | 9/2009 | Mensinger et al. |
| 2009/0242425 A1 | 10/2009 | Ullas et al. |
| 2009/0281399 A1 | 11/2009 | Keel et al. |
| 2010/0041971 A1 | 2/2010 | Goode, Jr. et al. |
| 2010/0094110 A1 | 4/2010 | Heller et al. |
| 2010/0145317 A1 | 6/2010 | Laster et al. |
| 2010/0149042 A1 | 6/2010 | Utsi et al. |
| 2010/0222847 A1 | 9/2010 | Goetz |
| 2010/0249558 A1 | 9/2010 | Yodfat et al. |
| 2011/0022025 A1 | 1/2011 | Savoie et al. |
| 2011/0137142 A1 | 6/2011 | Lucisano et al. |
| 2011/0221590 A1 | 9/2011 | Baker et al. |
| 2011/0319734 A1 | 12/2011 | Gottlieb et al. |
| 2012/0262298 A1 | 10/2012 | Bohm et al. |
| 2012/0283960 A1 | 11/2012 | Budiman |
| 2012/0323100 A1 | 12/2012 | Kamath et al. |
| 2013/0016573 A1 | 1/2013 | Goel et al. |
| 2013/0030273 A1 | 1/2013 | Tapsak et al. |
| 2013/0132416 A1 | 5/2013 | Hayter et al. |
| 2013/0165819 A1 | 6/2013 | Tieu |
| 2013/0172692 A1 | 7/2013 | Choi et al. |
| 2013/0178727 A1 | 7/2013 | Hayter et al. |
| 2013/0197332 A1 | 8/2013 | Lucisano et al. |
| 2014/0046148 A1 | 2/2014 | Simpson et al. |
| 2014/0121989 A1 | 5/2014 | Kamath et al. |
| 2014/0309510 A1 | 10/2014 | Lucisano et al. |
| 2014/0323960 A1 | 10/2014 | Sloan |
| 2014/0350652 A1 | 11/2014 | Suwito |
| 2015/0163602 A1 | 6/2015 | Pedersen et al. |
| 2015/0250429 A1 | 9/2015 | Hampapuram et al. |
| 2015/0289823 A1 | 10/2015 | Rack-Gomer et al. |
| 2015/0306304 A1 | 10/2015 | Schabbach et al. |
| 2015/0335285 A1 | 11/2015 | Poon et al. |
| 2016/0022180 A1 | 1/2016 | Joseph et al. |
| 2016/0029966 A1 | 2/2016 | Salas-Boni et al. |
| 2016/0033340 A1 | 2/2016 | Todd et al. |
| 2016/0073964 A1 | 3/2016 | Cobelli et al. |
| 2016/0134980 A1 | 5/2016 | Abolfathi |
| 2016/0163174 A1 | 6/2016 | Zhang |
| 2016/0235300 A1 | 8/2016 | Goodnow |
| 2016/0310027 A1 | 10/2016 | Han |
| 2016/0317744 A1 | 11/2016 | Rule |
| 2017/0074757 A1 | 3/2017 | Garcia et al. |
| 2017/0173262 A1 | 6/2017 | Veltz |
| 2017/0181628 A1 | 6/2017 | Burnette et al. |
| 2017/0181630 A1 | 6/2017 | Mahalingam et al. |
| 2017/0181674 A1 | 6/2017 | Lucisano et al. |
| 2017/0325725 A1 | 11/2017 | Shah et al. |
| 2017/0347932 A1 | 12/2017 | Lucisano et al. |
| 2017/0357776 A1 | 12/2017 | Baker et al. |
| 2018/0000395 A1 | 1/2018 | Lucisano et al. |
| 2018/0140239 A1 | 5/2018 | Lucisano et al. |
| 2018/0153450 A1 | 6/2018 | Routh et al. |
| 2018/0279911 A1 | 10/2018 | Lucisano et al. |
| 2018/0348154 A1 | 12/2018 | Lucisano et al. |
| 2019/0150805 A1 | 5/2019 | Routh et al. |
| 2019/0192768 A1 | 6/2019 | Gupta et al. |
| 2019/0246957 A1 | 8/2019 | Lucisano et al. |
| 2019/0380628 A1 | 12/2019 | Routh et al. |
| 2020/0000386 A1 | 1/2020 | Gupta et al. |
| 2020/0037932 A1 | 2/2020 | Lucisano et al. |
| 2020/0330043 A1 | 10/2020 | Gupta et al. |
| 2020/0337619 A1 | 10/2020 | Lucisano et al. |
| 2020/0352480 A1 | 11/2020 | Lucisano et al. |
| 2021/0022652 A1 | 1/2021 | Lucisano et al. |

FOREIGN PATENT DOCUMENTS

| | | |
|---|---|---|
| AU | 2020201630 A1 | 3/2020 |
| CA | 2843008 A1 | 1/2013 |
| CA | 3009489 A1 | 7/2017 |
| CN | 1355670 A | 6/2002 |
| CN | 1592570 A | 3/2005 |
| CN | 101006374 A | 7/2007 |

(56) References Cited

FOREIGN PATENT DOCUMENTS

| | | |
|---|---|---|
| CN | 201207090 Y | 3/2009 |
| EP | 0206531 A2 | 12/1986 |
| EP | 0852414 B1 | 11/2004 |
| EP | 2312782 A1 | 4/2011 |
| EP | 2736404 A1 | 6/2014 |
| EP | 3463059 A1 | 4/2019 |
| EP | 3478171 A1 | 5/2019 |
| EP | 3544491 A1 | 10/2019 |
| EP | 3547905 A1 | 10/2019 |
| EP | 3652547 A1 | 5/2020 |
| EP | 3906842 A1 | 11/2021 |
| JP | H11295556 A | 10/1999 |
| JP | 2000121863 A | 4/2000 |
| JP | 2005308982 A | 11/2005 |
| JP | 2007121886 A | 5/2007 |
| JP | 6321540 B2 | 5/2018 |
| KR | 20140082642 A | 7/2014 |
| WO | WO-9207525 A1 | 5/1992 |
| WO | WO-9213271 A1 | 8/1992 |
| WO | WO-2008013881 A2 | 1/2008 |
| WO | WO-2010002502 A2 | 1/2010 |
| WO | WO-2011018407 A1 | 2/2011 |
| WO | WO-2011120014 A1 | 9/2011 |
| WO | WO-2013016573 A1 | 1/2013 |
| WO | WO-2014035672 A2 | 3/2014 |
| WO | WO-2016014987 A2 | 1/2016 |
| WO | WO-2017117283 A1 | 7/2017 |
| WO | WO-2017210110 A1 | 12/2017 |
| WO | WO-2018005773 A1 | 1/2018 |
| WO | WO-2018097885 A1 | 5/2018 |
| WO | WO-2018102011 A1 | 6/2018 |
| WO | WO-2018183345 A1 | 10/2018 |
| WO | WO-2019013936 A1 | 1/2019 |
| WO | WO-2019126795 A1 | 6/2019 |
| WO | WO-2019135988 A1 | 7/2019 |
| WO | WO-2019246133 A1 | 12/2019 |
| WO | WO-2020006307 A1 | 1/2020 |

OTHER PUBLICATIONS

Anderson J.M., "Biological Responses to Materials." Annual Review of Materials Research, 2001, vol. 31, pp. 81-110.
Armour J.C., et al., "Application of a Chronic intravascular Blood Glucose Sensor in Dogs," Diabetes, 1990, vol. 39 (12), pp. 1519-1526.
Bard A.J., et al., "Electrochemical Methods: Fundamentals and Applications," 2nd Edition, 2000.
Bilitewski U., et al., "Glucose Biosensors Based on Thick Film Technology," Biosensors and Bioelectronics, 1991, vol. 6, pp. 369-373.
Bremer, T.M., et al., "Benchmark Data from the Literature for Evaluation of New Glucose Sensing Technologies," Diabetes Technology and< gwmw class="ginger-module-highlighter-mistake-type-2" id="gwmw-15482927780468996237581">therapeutics</gwmw>, 2001, vol. 3 (3), pp. 409-418.
Cha, C.S., et al., "Electrochemical Behaviour of Microfabricated Thick-film Electrodes," Sensors and Actuators B., 1990, vol. 2, pp. 277-281.
Choleau, et al., "Calibration of a Subcutaneous Amperometric Glucose Sensor Implanted for 7 Days in Diabetic Patients Part 2. Superiority of the One-point Calibration Method," Biosensors and Bioelectronics, 2002, vol. 17, pp. 641-646.
Choleau, et al., "Calibration of a Subcutaneous Amperometric Glucose Sensor Part 1. Effect of Measurement Uncertainties on the Determination of Sensor Sensitivity and Background Current.," Biosensors and Bioelectronics, 2002, vol. 17, pp. 647-654.
Conway M.J., et al., "Radio Telemetry of Blood Po2 in Vivo," Biomedical Engineering, 1973, vol. 8 (10), pp. 428-430.
Data Sheet—Platinum Oxygen Sensor Materials, Component Metallizations, OS1/OS2/OS3, Heraeus.
Data Sheet—Cermet Platinum Conductor, 5542 Print GD, 5542 Pouring GD, Electro-Science Laboratories,Inc.
Data Sheet—4082 and 3804 Platinum Conductors, MEMS Sensor Materials, Ferro Electronic Materials.
DuTronc, P., et al., "Influence of the Nature of the Screen-printed Electrode Metal on the Transport and Detection Properties of Thick-film Semiconductor Gas Sensors," Sensors and Actuators B, 1992, vol. 6, pp. 279-284.
Fischer U., et al., "A Membrane Combination for Implantable Glucose Sensors. Measurements in Undiluted Biological Fluids," Transactions—American Society for Artificial Internal Organs, 1982, vol. 28, pp. 245-248.
Golonka, et al., "The influence of the Electrode Material on the Sensitivity of an $Sno_2$ Thick-film Gas Sensor," Sensors and Actuators B, 1994, vol. 18-19, pp. 453-456.
Gough, et al., "A Novel Rotated Disc Electrode and Time Lag Method for Characterizing Mass Transport in Liquid-membrane Systems," Journal of the American Institute of Chemical Engineers, 1980, vol. 26, pp. 1013.
Gough, et al., "Membrane-covered, Rotated Disc Electrode," Analytical Chemistry, 1979, vol. 51, pp. 439-444.
Gough D.A., et al., "Two-Dimensional Enzyme Electrode Sensor for Glucose," Analytical Chemistry, 1985, vol. 57 (12), pp. 2351-2357.
Holc J., et al., "Interaction Between Thick-film Platinum Electrodes and Yttria-stabilized $Zro_2$ Ceramic," Journal of Materials Science Letters, 1989, vol. 8, pp. 635-637.
Jablecki M., et al., "Simulations of the Frequency Response of Implantable Glucose Sensors," Analytical Chemistry, 2000, vol. 72 (8), pp. 1853-1859.
Kovatchev B.P., et al., "Graphical and Numerical Evaluation of Continuous Glucose Sensing Time Lag," Diabetes Technology Therapeutics, 2009, vol. 11<gwmw class="ginger-module-highlighter-mistake-type-3" id="gwmw-15482928322330876684042">(</gwmw>3), pp. 139-143.
Leypoldt J.K., et al., "Diffusion and the Limiting Substrate in Two-substrate Immobilized Enzyme Systems," Biotechnology and Bioengineering, 1982, vol. 24 (12), pp. 2705-2719.
Leypoldt J.K., et al., "Model of a Two-substrate Enzyme Electrode for Glucose," Analytical Chemistry, 1984, vol. 56 (14), pp. 2896-2904.
Lucisano, et al., "In Vitro Stability of an Oxygen Sensor," Analytical Chemistry, 1987, vol. 59 (5), pp. 736-739.
Ma, et al., "A Biocompatible and Biodegradable Protein Hydrogel with Green and Red Autofluorescence: Preparation, Characterization and In Vivo Biodegradation Tracking and Modeling," Scientific Reports (Nature.com) published Jan. 27, 2016.
Makale M.T., et al., "Tissue Window Chamber System for Validation of Implanted Oxygen Sensors," American Journal of Physiology. Heart and Circulatory Physiology, 2003, vol. 284 (6), pp. 2288-2294.
McKean B.D., et al., "A Telemetry-Instrumentation System for Chronically Implanted Glucose and Oxygen Sensors," IEEE Transactions on Biomedical Engineering, 1988, vol. 35 (7), pp. 526-532.
Rich A., "Shielding and Guarding," Analog Dialogue, 1983,vol. 17 (1), pp. 8-13.
Sargent B.J., et al., "Design and Validation of the Transparent Oxygen Sensor Array," Biomedical Engineering, IEEE Transactions On, 1991, vol. 38 (5), pp. 476-482.
Morris C.G., Definition of "Machine Learning", Academic Press Dictionary of Science and Technology (4th ed.), 1992, Oxford, UK: Elsevier Science & Technology. Retrieved from https://search.credoreference.com/content/entry/apdst/machine_learning/0?institutionId=743.
Dhakar L., "Skin Based Flexible Triboelectric Nanogenerators with Motion Sensing Capability," Micro Electro Mechanical Systems (MEMS), 2015 28th IEEE International Conference on, 2015, IEEE, pp. 106-109.
ELISA Kit Manual Human C3a, catalog #550499, copyright 2001.
ELISA Kit Manual Human C4a, catalog #5550947, revised Feb. 2001.

(56) References Cited

OTHER PUBLICATIONS

Gough, et al., "Function of an Implanted Tissue Glucose Sensor for More than 1 Year in Animals", Science Translational Medicine, Jul. 28, 2010, vol. 2 (42), pp. 42ra53.

Heraeus Technical Data Sheet,Thick Film Materials, Product CL11-5100, retrieved from the Internet on Jun. 14, 2019.

Heraeus Technical Data Sheet,Thick Film Materials, Product CL11-5349, retrieved from the Internet on Jun. 14, 2019.

Heraeus Technical Data Sheet,Thick Film Materials, Product CL11-6109, retrieved from the Internet on Jun. 14, 2019.

Heraeus Technical Data Sheet,Thick Film Materials, Product LP11-4493, retrieved from the Internet on Jun. 14, 2019.

Holmes, et al., Handbook of Thick Film Technology, Electrochemical Publications Ltd (Glasgow: Bell and Bain Ltd., 1976).

Kroschwitz J., "Concise encyclopedia of polymer science and engineering," John Wiley, 1990, pp. 599-1341.

Lemey S., et al., "Wearable Flexible Lightweight Modular RFID Tag With Integrated Energy Harvester," IEEE Transactions on Microwave Theory and Techniques, 2016, vol. 64.7, pp. 2304-2314.

Lucisano, Ph.D. Dissertation, Univ. of Calif. (San Diego), pp. xv-xvi, 8-10, 26-30, 34-36, 96-97 (made available to the public on Dec. 15, 1988)—Call No. "T3.6.L821987".

McNaught A.D., et al., "The Compendium of Chemical Terminology," The Gold Book, Second Edition, Blackwell Science,1997.

Schultz J.S., et al., "Optical Fiber Affinity Sensors," Methods in Enzymology, K. Mosbach, Ed., Academic Press,1988, vol. 137, pp. 349-366.

Takei K., et al., "Design for a 400-MHz Passive RFID Prototype System for Long Range Applications," to be published in Proc. IEEE Int. Symp. Antennas Propag. 2007.

West, Electrodeposition and Corrosion Processes, 1971.

Wong CM., et al., "Glucose Oxidase: Natural Occurrence, Function, Properties and Industrial Applications," Applied Microbiology and Biotechnology, 2008, vol. 78 (6), pp. 927-938.

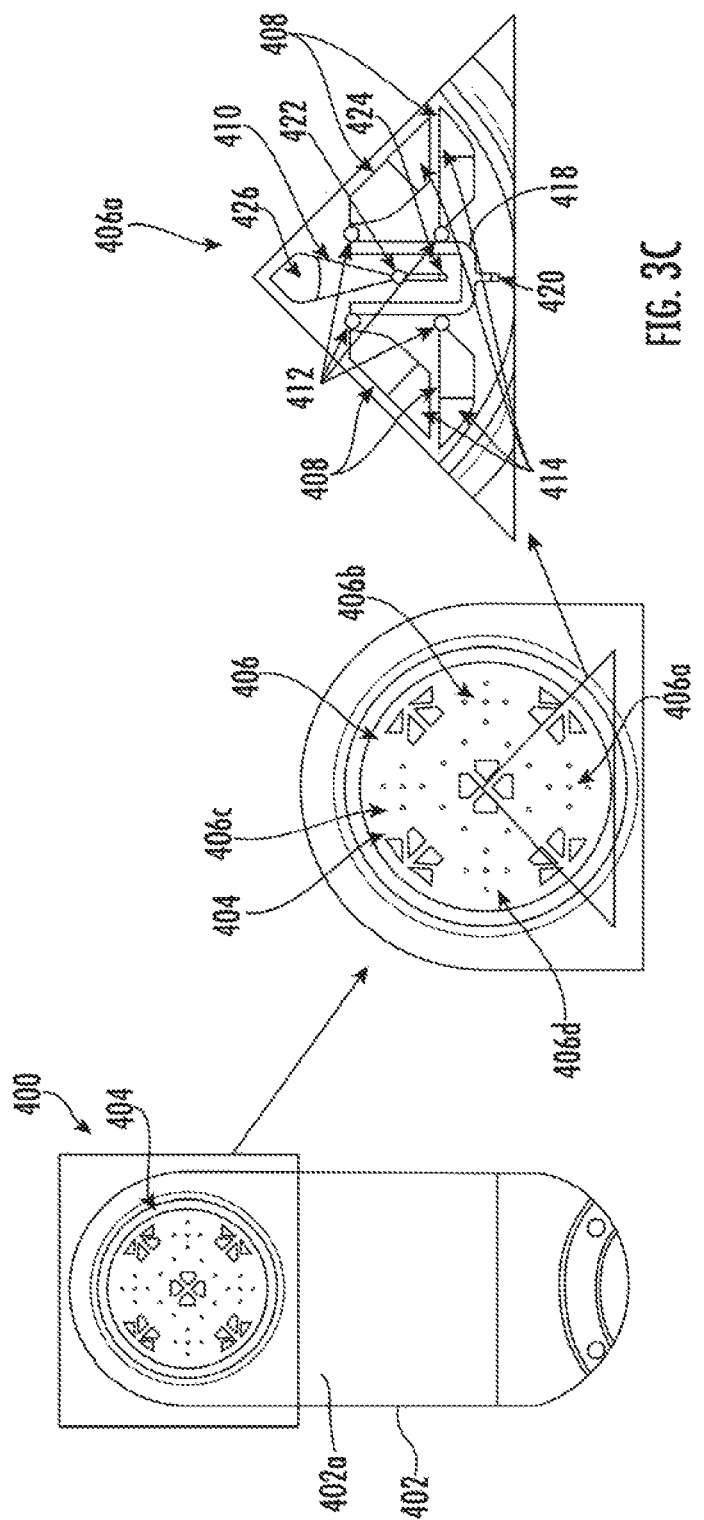

APPARATUS AND METHODS FOR ANALYTE SENSOR MISMATCH CORRECTION

PRIORITY AND RELATED APPLICATIONS

This application claims priority to co-owned U.S. Provisional Patent Application No. 62/613,695 filed on Jan. 4, 2018 and entitled "Apparatus and Methods for Analyte Sensor Mismatch Correction," which is incorporated herein by reference in its entirety.

This application is related to co-owned and co-pending U.S. patent application Ser. No. 15/853,574 filed Dec. 22, 2017 and entitled "Analyte Sensor And Medicant Delivery Data Evaluation And Error Reduction Apparatus And Methods"; Ser. No. 13/559,475 filed Jul. 26, 2012 entitled "Tissue Implantable Sensor With Hermetically Sealed Housing"; Ser. No. 14/982,346 filed Dec. 29, 2015 and entitled "Implantable Sensor Apparatus and Methods"; Ser. No. 15/170,571 filed Jun. 1, 2016 and entitled "Biocompatible Implantable Sensor Apparatus and Methods"; Ser. No. 15/197,104 filed Jun. 29, 2016 and entitled "Bio-adaptable Implantable Sensor Apparatus and Methods"; Ser. No. 15/359,406 filed Nov. 22, 2016 and entitled "Heterogeneous Analyte Sensor Apparatus and Methods"; Ser. No. 15/368,436 filed Dec. 2, 2016 and entitled "Analyte Sensor Receiver Apparatus and Methods"; Ser. No. 15/472,091 filed Mar. 28, 2017 and entitled "Analyte Sensor User Interface Apparatus and Methods"; and Ser. No. 15/645,913 filed Jul. 10, 2017 and entitled "Analyte Sensor Data Evaluation and Error Reduction Apparatus and Methods," each of the foregoing patent applications incorporated herein by reference in its entirety. This application is also related to co-owned U.S. Provisional Patent Application No. 62/687,115 filed Jun. 19, 2018 and entitled "Analyte Sensor Apparatus and Methods"; and, 62/690,745 filed on Jun. 27, 2018 and entitled "Apparatus and Methods for Analyte Sensor Spatial Mismatch Correction," each of the foregoing provisional patent applications incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

1. Technical Field

The disclosure relates generally to the field of data analysis and processing, including without limitation for sensors, therapy devices, implants and other devices (such as those which can be used consistent with human beings or other living entities), and in one exemplary aspect to methods and apparatus for accurately measuring physiological parameters such as blood analyte level, through use of error or mismatch identification, analysis, and/or correction routines or computer programs, the latter which enhance the accuracy and reliability of such physiological parameter measurements.

2. Description of Related Technology

Implantable electronics is a rapidly expanding discipline within the medical arts. Owing in part to significant advances in electronics and wireless technology integration, miniaturization, performance, and material biocompatibility, sensors or other types of electronics which once were beyond the realm of reasonable use within a living subject (i.e., in vivo) can now be surgically implanted within such subjects with minimal effect on the recipient subject, and in fact convey many inherent benefits.

One particular area of note relates to blood analyte monitoring for subjects, such as for example glucose monitoring for those with so-called "type 1" or "type 2" diabetes. As is well known, regulation of blood glucose is impaired in people with diabetes by: (1) the inability of the pancreas to adequately produce the glucose-regulating hormone insulin; (2) the insensitivity of various tissues that use insulin to take up glucose; or (3) a combination of both of these phenomena. Safe and effective correction of this dysregulation requires blood glucose monitoring.

Currently, glucose monitoring in the diabetic population is based largely on collecting blood by "fingersticking" and determining its glucose concentration by conventional assay. This procedure has several disadvantages, including: (1) the discomfort associated with the procedure, which should be performed repeatedly each day; (2) the near impossibility of sufficiently frequent sampling (some blood glucose excursions require sampling every 20 minutes, or more frequently, to accurately treat); and (3) the requirement that the user initiate blood collection, which precludes warning strategies that rely on automatic early detection. Using the extant fingersticking procedure, the frequent sampling regimen that would be most medically beneficial cannot be realistically expected of even the most committed patients, and automatic sampling, which would be especially useful during periods of sleep, is not available.

Implantable glucose sensors (e.g., continuous glucose monitoring (CGM) sensors) have long been considered as an alternative to intermittent monitoring of blood glucose levels by the fingerstick method of sample collection. These devices may be fully implanted, where all components of the sensor system reside within the body and there are no through-the-skin (i.e. percutaneous) elements, or they may be partially implanted, where certain components reside within the body but are physically connected to additional components external to the body via one or more percutaneous elements, or they may be of a hybrid nature, where one element of the sensor system is fully implanted, but another element required for operation (e.g. a power source for the implanted element) must be worn in close proximity to the implanted element, but outside of the body on the skin at all times that the system is intended to operate. Further, such devices provide users a great deal of freedom from potentially painful intermittent sampling methods such as "fingersticking." as well as having to remember and obtain self-administered blood analyte readings.

The accuracy of blood analyte detection and measurement is an important consideration for implanted analyte sensors, especially in the context of current blood glucose monitoring systems (such as e.g., fully implanted blood glucose sensor systems), and even the future development of implantable blood glucose monitoring systems (such as e.g., in support of the development of an artificial pancreas). Hence, ensuring accurate measurement for extended periods of time (and minimizing the need for any other confirmatory or similar analyses) is of great significance. In conventional sensors, accuracy can be adversely affected by a myriad of factors such as e.g., random noise, foreign body response (FBR), other tissue responses, anoxia or hypoxia in the region of the analyte sensor, blood analyte tissue dynamics, mechanical jarring, migration, the presence of confounding compounds, material and/or mechanical properties of sensor electrodes and associated membrane structures, bulk layer variations, and/or other variables.

Further, exemplary sensors (such as those of the ICGM® system manufactured by the Assignee hereof) may utilize a differential (ratiometric) measurement-based sensor for estimating tissue/blood glucose. As with typical differential (or ratiometric) measurement-based systems, the common mode signal measured in the sensors (electrodes) should be temporally synchronous to minimize noise/errors, and to allow correct extraction of the true differential component of the signal. For example, if two steady-state-calibrated sensors introduce different temporal lags while measuring a common time-varying signal (e.g. as shown in FIG. 1A), the ratiometric result (i.e., ratio of the two measurements) of the sensors will not remain at unity, but will rather consist of a systematic error pertaining to the temporal mismatch (e.g., as shown in FIG. 1B), thereby adversely affecting accuracy of the sensor.

Specifically, FIG. 1A illustrates signals measured by two sensors (i.e., Sensor 1 and Sensor 2) injecting different temporal lags from their sensing mechanism, as compared with the "true" signal. In FIG. 1B, the solid line curve represents the ratio of the measurements from Sensor 1 and Sensor 2 from FIG. 1A, while responding to the same time-varying signal. The expected ideal ratiometric measurement (ratio of Sensor 1 to Sensor 2) as a function of time is unity (the dashed line in FIG. 1B), whereas the deviation from the dashed line is due to the temporal mismatch.

Similarly, the difference between the two signals will not remain at zero over time, but will instead consist of an error due to response mismatch, as shown in FIG. 1C. Specifically, in FIG. 1C, the solid line curve represents the difference in the measurements of Sensor 1 and Sensor 2 while responding to the same time-varying signal. The expected ideal differential measurement is 0 (shown in dashed line), whereas the deviation from the dashed line is due to the temporal (response) mismatch.

Additionally, in certain cases the temporal lags injected by the sensors (during the measurement of a signal) may not remain constant over time and/or under different operating conditions, but may change as a function of time or other specified parameters. For example, the two electrodes (of a differential pair) in the exemplary ICGM sensor are subject to two different processes, measuring background oxygen in one and glucose-modulated oxygen in another, and their responses to a change in oxygen concentration as a function of time may not be assumed to be matched under all operating conditions. In an exemplary ICGM sensor design, the glucose and oxygen electrodes can be constructed in a way that their temporal responses to an oxygen change are well matched at a certain operating condition (e.g., in the absence of glucose, at glucose of 100 mg/dl, etc.). However, as the operating conditions change (e.g., glucose=200 mg/dl, etc.), the time response of the glucose electrode may deviate from that of the oxygen electrode (since only the glucose electrode responds to the presence of glucose), resulting in a temporal (response) mismatch, which reduces accuracy of any calculated glucose level determined from the collected sensor signals.

In another example, differential electrodes may have varying physical properties, such as, e.g. spatial and/or material properties of an associated membrane structure that affect temporal mismatch. A glucose-modulated detector element may include, for example, a multi-layer membrane structure disposed over its working electrode. The multi-layer membrane structure includes at least an inner silicone membrane, an intermediate membrane comprising a cross-linked protein and enzyme-embedded material, and an outer silicone membrane having a spout region with a cross-linked protein (enzyme-free) membrane disposed within an opening of the spout. In some cases, the background oxygen sensing element can have a similar structure associated with its working electrode (excluding enzyme from its intermediate membrane); however, similar membrane structures are not required. In fact, there may be design advantages (including e.g., enabling a closer proximity arrangement of differential electrodes) to having an alternative membrane structure for the background electrode, such as an entirely silicone membrane structure and/or a membrane structure of a different thickness than that of its associated analyte-modulated electrode. Such material and/or structural differences may introduce additional sources of temporal mismatch due to e.g., different permeability of the membrane structures to analyte and/or background species.

In yet another example, it may be desirable to temporally match or otherwise relate or compensate for signals from one or more other types of sensors (e.g. temperature sensors, pressure sensors, accelerometers, etc. having varying temporal signal characteristics) with signals from the analyte and background sensor elements.

Accordingly, there is a salient need for, inter alia, methods and apparatus which compensate, relate, or at least partly correct for temporal mismatch between, for example, two electrodes of a differential electrode pair and/or a group of associated sensors. Ideally, such methods and apparatus would be able to operate dynamically, including compensation, relation or correction during operation of the electrode pair(s) and/or the group of associated sensors while implanted within a living subject (i.e., in vivo). The ability for such dynamic operation to occur substantially autonomously (e.g., based on processing/algorithms operative on the implanted device alone) would also be a desirable attribute in some circumstances or applications.

SUMMARY

The present disclosure satisfies the foregoing needs by providing, inter alia, improved methods and apparatus for compensation within a physiological parameter sensor, such as e.g., a differential oxygen-based blood glucose sensor.

In a first aspect, an apparatus for use in an implantable sensor apparatus is disclosed. In one embodiment, the apparatus includes one or more differential sensor pairs configured to measure or detect an analyte, and computerized logic configured to correct individual ones of the sensors of each pair for mismatch relative to the other sensor of the same pair. In one variant, the mismatch is created via at least a differential time constant for the one sensor of the pair versus the other.

In one implementation, the sensor pair(s) is/are part of an implanted blood glucose sensor (i.e., part of a so-called "continuous glucose monitor" or CGM), and the corrected blood analyte data are corrected blood glucose concentration data (and/or corrected blood glucose rate of change (ROC) data). The glucose sensor in this implementation is an oxygen-based glucose sensor.

In another implementation, the glucose sensor is a hydrogen peroxide-based glucose sensor.

In yet another implementation, the glucose sensor includes both a hydrogen peroxide-based sensor and oxygen-based glucose sensor.

In another embodiment, the apparatus includes one or more groups of differential sensors each configured to measure or detect an analyte, and computerized logic configured to correct individual ones of the sensors of each group for mismatch relative to the other sensors of the same group. In one variant, the mismatch is created via at least a differential time constant for at least one sensor of the group versus the others. In another variant, the mismatch is created via at least a differential dead-time for at least one sensor of the group versus the others.

In one implementation, the sensor includes a single analyte (glucose)-modulated sensor element associated with multiple (e.g., four) background sensor elements, and a membrane structure (or a region of a common membrane structure) disposed over the background electrodes which has different configuration than a membrane structure (or a region of the common membrane structure) disposed over the glucose-modulated electrode.

In yet another embodiment, the apparatus includes one or more differential sensor pairs or groups configured to measure or detect an analyte, one or more non-analyte sensors, and computerized logic configured to correct individual ones of the non-analyte sensors for mismatch relative to the one or more differential sensor pairs or groups. In one variant, the mismatch is created via one or more of a dead-time (delay) and a time constant (lag) for each of the one or more non-analyte sensors versus the one or more differential sensor pairs or groups.

In one implementation, the computerized logic is further configured to utilize signals generated by various one of the one or more non-analyte sensors in a context specific operational model utilized for calculation of blood analyte from signals generated by the one or more differential sensor pairs or groups.

In another aspect, a method of operating an analyte sensor is disclosed. In one embodiment, the analyte sensor is configured to determine a concentration of a physiologic analyte, and the method includes: determining a response of a first electrode of the analyte sensor; determining a response of a second electrode of the analyte sensor, the response of the second electrode having at least one temporal response characteristic different than that of the first electrode; applying a mathematical transformation to the determined response of the second electrode to generate a transformed response; and utilizing (i) the determined response of the first electrode and (ii) the transformed response, to determine the concentration of the physiologic analyte.

In one variant, the physiologic analyte comprises blood glucose, the analyte sensor comprises an oxygen-based blood glucose sensor, and the first and second electrodes comprise background oxygen and glucose sensing electrodes respectively.

In yet another aspect of the disclosure, a method of monitoring a blood analyte level of a living being using a blood analyte sensing apparatus is disclosed. In one embodiment, the method includes: (i) characterizing one or more performance aspects of a particular analyte sensor apparatus with respect to the physiology of the particular living being; (ii) based at least on the characterizing; generating a sensor-specific transformation algorithm; and (iii) applying the generated transformation algorithm to at least one sensor element of the particular analyte sensor apparatus to correct for temporal or other mismatch of the at least one sensor element to another sensor element of the same sensor apparatus.

In another aspect, a computer readable apparatus is disclosed. In one embodiment, the computer readable apparatus comprises a storage medium (e.g., magnetic, solid state, optical, or other storage medium) having at least one computer program disposed thereon and readable by a computerized apparatus. The at least one computer program includes, in one variant, a plurality of instructions which, when executed on the computerized apparatus, cause transformation of detected response signals from one or more analyte detector electrodes in order to temporally adjust or align them to the detected response signals of one or more other electrodes, or a target temporal response.

In another aspect, a method of monitoring a blood analyte level of a living being using a blood analyte sensing apparatus is disclosed.

In yet another aspect, a method of compensating for or correcting errors caused at least in part due to differences in temporal response of two detecting electrodes is disclosed.

In yet another aspect of the disclosure, a computerized network apparatus is disclosed. In one embodiment, the network apparatus includes a cloud-based server apparatus configured to store, and optionally analyze, raw or partially processed blood analyte data obtained from a sensor implanted within a living being. In one variant, raw sensor data from one or more electrode differential pairs of the sensor are transmitted from the sensor via wireless interface either directly or indirectly to the cloud-based server apparatus for modeling, signal transformation, and blood analyte estimation, with the final estimated blood analyte level transmitted back to the sensor or other designated receiver.

In still another aspect of the disclosure, a portable electronic apparatus is disclosed. In one embodiment, the portable electronic apparatus includes a portable receiver device configured to perform data calculation and transformation operations for an internal (implanted) blood analyte sensor apparatus with which it is in data communication; e.g., via wireless interface.

In another aspect of the present disclosure, a method of operating a computerized apparatus for use with an analyte sensor is disclosed. In one embodiment, the method is for determination of a concentration of a physiologic analyte, and the method includes: determining data indicative of a response of a first detector of the analyte sensor; determining data indicative of a response of a second detector of the analyte sensor, the response of the second detector having at least one temporal response characteristic different than that of the response of the first detector; applying a mathematical transformation algorithm to the determined data indicative of the response of the second detector to generate data indicative of a transformed response; and utilizing (i) the determined data indicative of the response of the first detector and (ii) the generated data indicative of the transformed response, to determine the concentration of the physiologic analyte.

In another aspect of the present disclosure, a sensor apparatus is disclosed. In one embodiment, the sensor apparatus includes: a first detector; a second detector; storage apparatus in data communication with processor apparatus, the storage apparatus having at least one computer program stored thereon, the at least one computer program including a plurality of instructions which are configured to, when executed by the processor apparatus, cause the sensor apparatus to: determine data indicative of a signal response of the first detector; determine data indicative of a signal response of the second detector, the data indicative of the signal response of the second detector having at least one temporal response characteristic different than that of the first detector; utilize a pre-determined temporal mismatch correction algorithm on the data indicative of the determined response of the second detector to generate data indicative of a transformed response of the second detector; calculate a physiologic parameter value based at least in part on (i) the data indicative of the determined signal response of the first detector, and (ii) the data indicative of the transformed response of the second detector.

Other features and advantages of the present disclosure will immediately be recognized by persons of ordinary skill in the art with reference to the attached drawings and detailed description of exemplary embodiments as given below.

BRIEF DESCRIPTION OF THE DRAWINGS

FIG. 3A-3C are top elevation views of, respectively, (i) a second exemplary fully implantable sensor apparatus useful with the techniques of the present disclosure, (ii) an exemplary detector array, and (iii) a detector group of the exemplary array, the detector array comprising a plurality of detector element groups, each group comprising a single analyte-modulated electrode associated with a plurality of background electrodes.

Figure 1A:
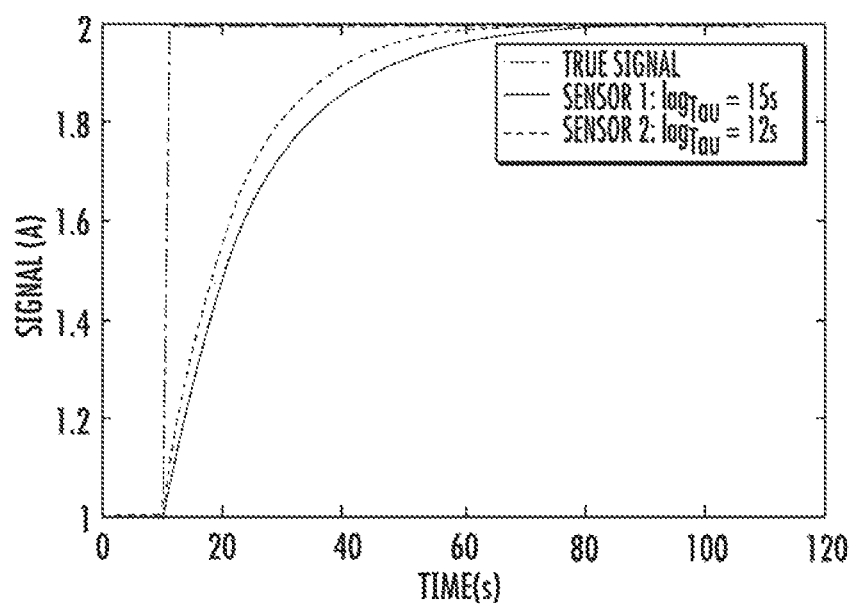
FIG. 1A is a graphical representation of signals measured by prior art sensing apparatus (including Sensor 1 and Sensor 2) as compared with the true signal.
Figure 1B:
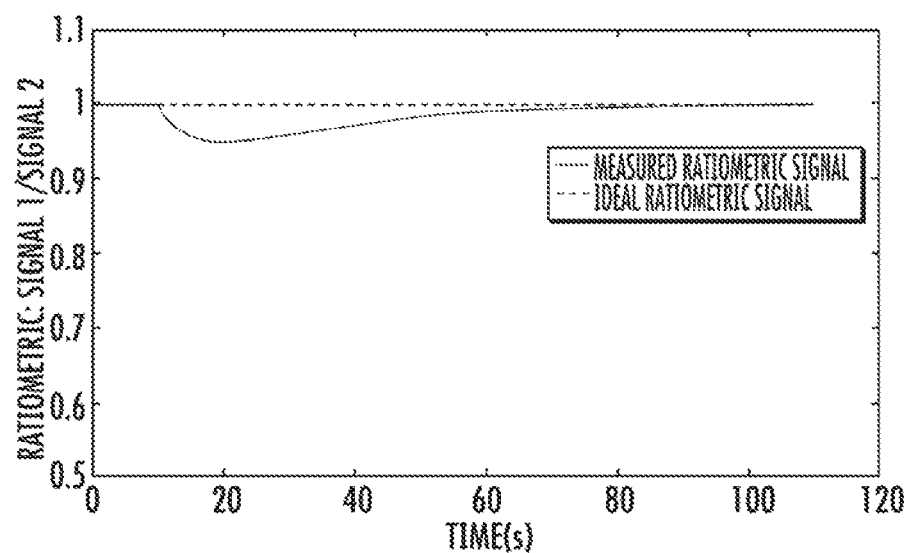
FIG. 1B is a graphical representation of the ratio of the measurements from the prior art sensing apparatus of FIG. 1A, while responding to the same time-varying signal.
Figure 1C:
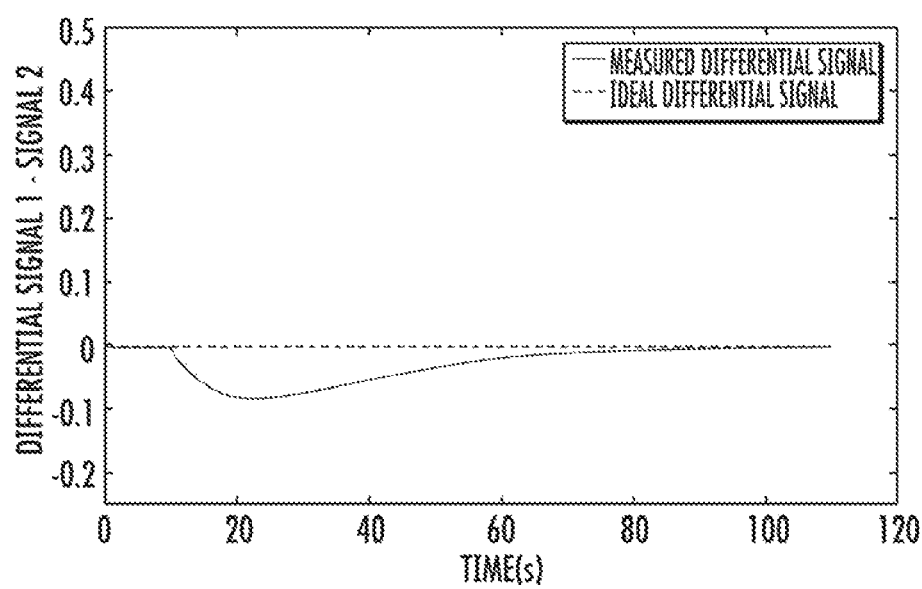
FIG. 1C is a graphical representation of the difference of the measurements from the prior art sensing apparatus of FIG. 1A, while responding to the same time-varying signal.

All Figures© Copyright 2017-2018 GlySens Incorporated. All rights reserved.

DETAILED DESCRIPTION

Reference is now made to the drawings, wherein like numerals refer to like parts throughout.

Overview

In one exemplary aspect, the present disclosure provides apparatus and methods which correct or compensate for temporal response mismatch, such as those observed in blood analyte sensing elements and/or other sensing elements (e.g., non-analyte sensing elements) associated therewith. In one embodiment, the blood analyte sensing elements are part of an implantable blood glucose monitor utilizing oxygen-based sensing, and the temporal response mismatch occurs between oxygen and glucose electrodes (e.g., arranged as differential sensor pairs as in the exemplary Model 100 analyte sensor manufactured by the Assignee hereof and described in co-owned and co-pending U.S. patent application Ser. Nos. 13/559,475, 14/982,346, 15/170,571, 15/197,104, and 15/359,406, each previously incorporated herein; or arranged as differential sensor groups as in the exemplary GEN 3 Model also manufactured by the Assignee hereof and described in co-owned U.S. Provisional Patent Application Nos. 62/687,115, and 62/690,745, each previously incorporated herein). An algorithmic approach is utilized to minimize the effect of the mismatch and, therefore, its impact on computed blood analyte levels (e.g., blood glucose concentration).

Specifically, in one implementation, a temporal mismatch model is utilized that establishes the differences in the response characteristics of two or more electrodes. For example, differential sensing elements are characterized by the foregoing model as a function of the ratio of glucose concentration to oxygen concentration. Moreover, given that the time constants and delay (dead-time) of the two or more electrodes are predictable (can be estimated via the foregoing model) at any given time, correction or compensation for the temporal response (lag and/or delay) mismatch between the two or more electrodes can be computed, thereby enabling more accurate computation of the target analyte, such as blood glucose.

In one embodiment, the foregoing model is applied in an in vitro environment to characterize delay and lag of associated sensing elements of an implantable sensor apparatus. Subsequently, the model and the determined time constants and/or dead-time are utilized to correct temporal mismatch of signals after implantation of the sensor apparatus in a tissue environment of a subject (e.g., within the abdominal region of a human subcutaneous tissue proximate the abdominal muscle fascia). In another embodiment, a sensor apparatus is first implanted and a model is applied on a set of training data utilizing pre-determined time constants and/or dead-time (e.g., time constants and/or dead-time associated with a class of sensor apparatus comprising a specific sensor element configuration) which are incrementally or otherwise step-adjusted to "train" the model for optimized sensor accuracy in a specific tissue environment. Alternatively, both methods can be carried out (i.e., initial characterization of the associated sensor elements in vitro, and subsequent training of the model in vivo.)

The apparatus and methods described here may also advantageously be applied to similarly benefit other measurement systems that utilize differential/interacting/dependent detector or sensor approaches.

DETAILED DESCRIPTION OF EXEMPLARY EMBODIMENTS

Exemplary embodiments of the present disclosure are now described in detail. While these embodiments are primarily discussed in the context of a fully implantable glucose sensor, such as those exemplary embodiments described herein, and/or those set forth in U.S. Patent Application Publication No. 2013/0197332 filed Jul. 26, 2012 entitled "Tissue Implantable Sensor With Hermetically Sealed Housing;" U.S. Pat. No. 7,894,870 to Lucisano et al. issued Feb. 22, 2011 and entitled "Hermetic Implantable Sensor;" U.S. Patent Application Publication No. 2011/0137142 to Lucisano et al. published Jun. 9, 2011 and entitled "Hermetic Implantable Sensor;" U.S. Pat. No. 8,763,245 to Lucisano et al. issued Jul. 1, 2014 and entitled "Hermetic Feedthrough Assembly for Ceramic Body;" U.S. Patent Application Publication No. 2014/0309510 to Lucisano et al. published Oct. 16, 2014 and entitled "Hermetic Feedthrough Assembly for Ceramic Body;" U.S. Pat. No. 7,248,912 to Gough et al. issued Jul. 24, 2007 and entitled "Tissue Implantable Sensors for Measurement of Blood Solutes;" and U.S. Pat. No. 7,871,456 to Gough et al. issued Jan. 18, 2011 and entitled "Membranes with Controlled Permeability to Polar and Apolar Molecules in Solution and Methods of Making Same;" and U.S. Patent Application Publication No. 2013/0197332 to Lucisano et al. published Aug. 1, 2013 and entitled "Tissue Implantable Sensor with Hermetically Sealed Housing;" PCT Patent Application Publication No. 2013/016573 to Lucisano et al. published Jan. 31, 2013 and entitled "Tissue Implantable Sensor with Hermetically Sealed Housing," each of the foregoing incorporated herein by reference in its entirety, as well as those of U.S. patent application Ser. Nos. 13/559,475, 14/982,346, 15/170,571, 15/197,104, 15/359,406, 15/368,436, 15/472,091, 15/645,913, and 15/853,574, and U.S. Provisional Patent Ser. Nos. 62/687,115, and 62/690,745, each previously incorporated herein, it will be recognized by those of ordinary skill that the present disclosure is not so limited. In fact, the various aspects of the disclosure are useful with, inter alia, other types of sensors, medicant delivery devices, and/or electronic devices, including those relating to other analytes.

Further, while the following embodiments describe specific implementations of e.g., biocompatible oxygen-based multi-sensor element devices for measurement of glucose having specific configurations, protocols, locations, and orientations for implantation (e.g., sensor implantation proximate the waistline on a human abdomen with the sensor array disposed proximate to fascial tissue); see e.g., U.S. patent application Ser. No. 14/982,346, entitled "Implantable Sensor Apparatus and Methods" and filed Dec. 29, 2015, previously incorporated herein; those of ordinary skill in the related arts will readily appreciate that such descriptions are purely illustrative, and in fact the methods and apparatus described herein can be used consistent with, and without limitation: (i) in living beings other than humans; (ii) other types or configurations of sensors (e.g., other types, enzymes, and/or theories of operation of glucose sensors, sensors other than glucose sensors, such as e.g., sensors for other analytes such as urea, lactate); (iii) other implantation locations and/or techniques (including without limitation transcutaneous or non-implanted devices as applicable); (iv) other types of differential sensing devices (regardless of the measured analyte or substance), and/or (v) other devices (e.g., non-sensors and non-substance delivery devices).

As used herein, the term "analyte" refers without limitation to a substance or chemical species that is of interest in an analytical procedure. In general, the analyte itself may or may not be directly measurable; in cases where it is not, a measurement of the analyte (e.g., glucose) can be derived through measurement of chemical constituents, components, or reaction byproducts associated with the analyte (e.g., hydrogen peroxide, oxygen, free electrons, etc.). It will be appreciated that although reference is made throughout to "blood analyte" and "blood analyte level," that the principles of the invention are not restricted to systems where the parameter is solely a blood analyte level. To that end, the terms "blood analyte" and "blood analyte level" can be taken as synonymous with "physiologic parameter" and "physiologic parameter level."

As used herein, the terms "detector" and "sensor" refer without limitation to a device having one or more elements (e.g., detector element, sensor element, sensing elements, etc.) that generate, or can be made to generate, a signal indicative of a measured parameter, such as the concentration of an analyte (e.g., glucose) or its associated chemical constituents and/or byproducts (e.g., hydrogen peroxide, oxygen, free electrons, etc.). Such a device may be based on electrochemical, electrical, optical, mechanical, thermal, or other principles as generally known in the art. Such a device may consist of one or more components, including for example, one, two, three, or four electrodes, and may further incorporate immobilized enzymes or other biological or physical components, such as membranes, to provide or enhance sensitivity or specificity for the analyte.

As used herein the term "parent platform" refers without limitation to any device, group of devices, and/or processes with which a client or peer device (including for example the various embodiments of receiver described herein and the various exemplary configurations in the aforementioned patent applications previously incorporated herein) may logically and/or physically communicate to transfer or exchange data. Examples of parent platforms can include, without limitation, smartphones, tablet computers, laptops, smart watches, personal computers/desktops, servers (local or remote), gateways, dedicated or proprietary analyte receiver devices, medical diagnostic equipment, and even other local receivers acting in a peer-to-peer or dualistic (e.g., master/slave) modality.

As used herein, the term "application" (or "app") refers generally and without limitation to a unit of executable software that implements a certain functionality or theme. The themes of applications vary broadly across any number of disciplines and functions (such as on-demand content management, e-commerce transactions, brokerage transactions, home entertainment, calculator etc.), and one application may have more than one theme. The unit of executable software generally runs in a predetermined environment; for example, the Java® environment.

As used herein, the term "computer program" or "software" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VoXML), and the like, as well as object-oriented environments such as the Common Object Request Broker Architecture (CORBA), Java® (including J2ME, Java Beans, etc.) and the like.

As used herein, the term "memory" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

As used herein, the terms "microprocessor" and "processor" or "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, state machines, reconfigurable computer fabrics (RCFs), array processors, secure microprocessors, and application-specific integrated circuits (ASICs). Such digital processors may be contained on a single unitary integrated circuit (IC) die, or distributed across multiple components.

As used herein, the term "interface" refers to any signal or data interface with a component or network including, without limitation, those of the FireWire (e.g., FW400, FW800, etc.), USB (e.g., USB 2.0, 3.0. OTG), Ethernet (e.g., 10/100, 10/100/1000 (Gigabit Ethernet), 10-Gig-E, etc.), MoCA, LTE/LTE-A, Wi-Fi (802.11), WiMAX (802.16), Z-wave, PAN (e.g., 802.15)/Zigbee, CBRS (Citizens Broadband Radio Service), Bluetooth, Bluetooth Low Energy (BLE) or power line carrier (PLC) families.

As used herein, the term "storage" refers to without limitation computer hard drives, memory, RAID devices or arrays, optical media (e.g., CD-ROMs, Laserdiscs, Blu-Ray, etc.), solid state devices (SSDs), flash drives, cloud-hosted storage, or network attached storage (NAS), or any other devices or media capable of storing data or other information.

As used herein, the term "wireless" means any wireless signal, data, communication, or other interface including without limitation Wi-Fi, Bluetooth (including BLE or "Bluetooth Smart"), 3G (3GPP/3GPP2), HSDPA/HSUPA, TDMA, CDMA (e.g., IS-95A, WCDMA, etc.), FHSS, DSSS, GSM, PAN/802.15, WiMAX (802.16), 802.20, Zigbee®, Z-wave, narrowband/FDMA, OFDM, PCS/DCS, LTE/LTE-A/LTE-U/LTE-LAA, CBRS (Citizens Broadband Radio Service), analog cellular, CDPD, satellite systems, millimeter wave or microwave systems, acoustic, and infrared (i.e., IrDA).

Exemplary Sensor Apparatus and Sensing Elements

Figure 2A:
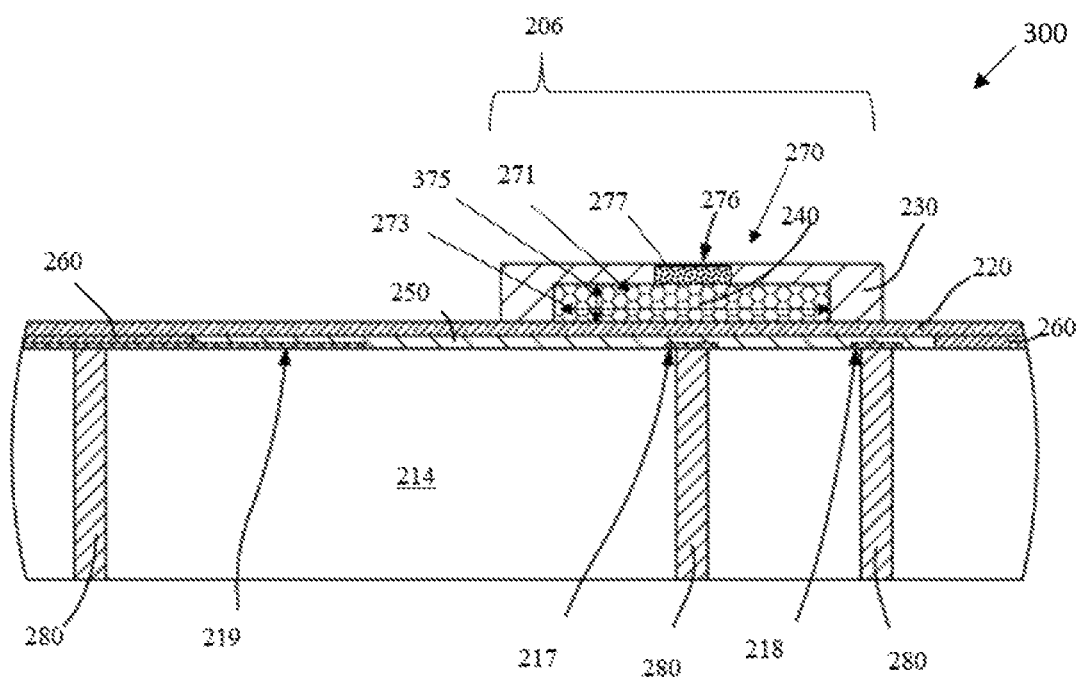
FIG. 2A is a side cross-sectional view of one exemplary detector element useful with the techniques of the present disclosure.
Figure 2B:
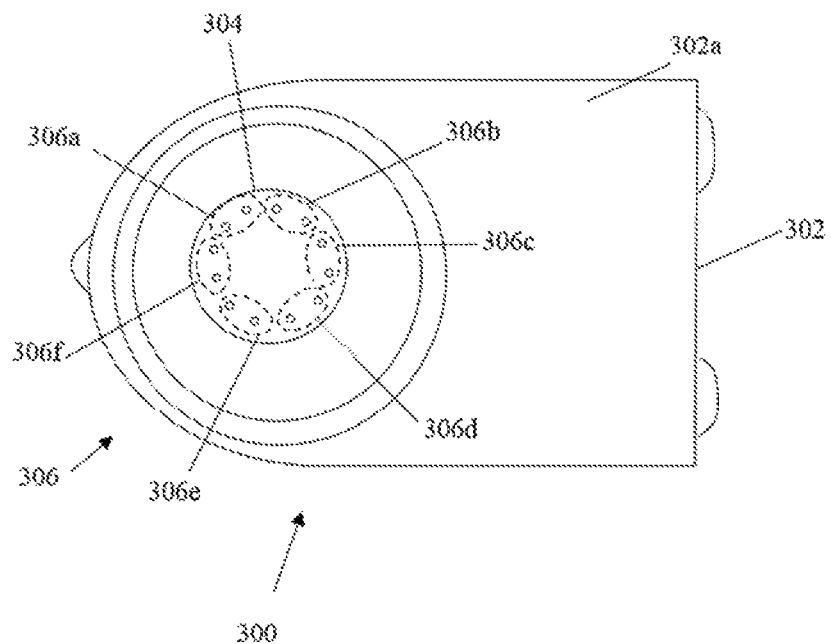
FIG. 2B is a top elevation view of a first exemplary fully implantable sensor apparatus useful with the techniques of the present disclosure, the first exemplary fully implantable sensor apparatus including an exemplary detector array comprising a plurality of paired differential detector elements, such as the exemplary detector element shown in FIG. 2A.

In one exemplary embodiment illustrated in FIGS. 2A and 2B, a sensor apparatus 300 comprises a plurality of paired sensing or detector elements, such as the paired analyte-modulated and background sensor elements utilized to determine a ratiometric or differential signal indicative of a blood analyte concentration discussed supra, as well as in U.S. patent application Ser. Nos. 13/559,475, 14/982,346, 15/170,571, and 15/197,104, 15/359,406, 15/368,436, 15/472,091, 15/645,913, and 15/853,574, previously incorporated by reference herein.

In one specific implementation, as shown in FIG. 2A, an exemplary individual detector element 206 is shown associated with detector substrate 214 (e.g. ceramic substrate), and generally comprises a plurality of membranes and/or layers, including e.g., the insulating layer 260, and electrolyte layer 250, an enzymatic gel matrix 240, an inner membrane 220, an exterior membrane shell 230, and a non-enzymatic membrane 277. Such membranes and layers are associated with the structure of each of the individual detector elements, although certain membrane layers can be disposed in a continuous fashion across the entire detector array surface or portions thereof that include multiple detectors, such as for economies of scale (e.g., when multiple detectors are fabricated simultaneously), or for maintaining consistency between the individual detector elements by virtue of making their constituent components as identical as possible, thereby e.g., minimizing temporal mismatch between paired sensing elements.

Generally, the thickness of each of the membranes disclosed herein is not particularly limited, as long as the desired permeability properties are achieved. However, particular requirements for sensor response time, glucose concentration detection range, and/or reduction of antibody response (e.g., FBR), may impose limits on the allowable membrane thickness. Membrane thickness can be, for example, about 1 micron to about 1000 microns, or more particularly, about 10 microns to about 500 microns, or more particularly about 25 microns to about 250 microns in certain applications. U.S. Pat. No. 7,336,984 and entitled "Membrane and Electrode Structure for Implantable Sensor," previously incorporated herein, describes exemplary membrane apparatus, thickness values, and computerized modeling techniques useful with the various aspects of the present disclosure, although it will be recognized that other techniques, apparatus, and methods for membrane configuration may be used consistent with the present disclosure.

As shown in FIG. 2A, the detector element 206 further comprises a working electrode 217 in operative contact (by means of the electrolyte layer 250) with a counter electrode 219 and a reference electrode 218, and their associated feedthroughs 280 (details of the exemplary feedthroughs 380 are described in U.S. Pat. No. 8,763,245 to Lucisano et al. entitled "Hermetic feedthrough assembly for ceramic body," previously incorporated by reference herein). The working electrode 217 comprises an oxygen-detecting catalytic surface producing a glucose-modulated, oxygen-dependent current (discussed infra). A reference electrode 218 comprises an electrochemical potential reference contact to electrolyte layer 250, and a counter electrode 219 is operably connected by means of electrolyte layer 250 to the working electrode 217 and reference electrode 218. An electrical potentiostat circuit (not shown) is coupled to the electrodes 217, 218, and 219 to maintain a fixed potential between the working and reference electrode by passing current between the working and counter electrodes while preferably maintaining the reference electrode at high impedance. Such potentiostat circuitry is well known in the art (for an example, see U.S. Pat. No. 4,703,756 to Gough et al. entitled "Complete glucose monitoring system with an implantable, telemetered sensor module," incorporated herein by reference in its entirety).

In one embodiment, the sensor apparatus utilizes an "oxygen-sensing differential measurement," by comparison of the glucose-dependent oxygen signal (i.e., from the primary or enzyme-containing sensor elements) to the background oxygen signal (i.e., from the secondary non-enzyme-containing sensor elements) that produces, upon further signal processing, a continuous real-time blood glucose concentration measurement.

In one variant, the enzyme-embedded membrane includes embedded glucose oxidase (GOx) and catalase enzymes and the sensor elements are configured for detection of glucose based on the following two-step chemical reaction catalyzed by GOx and catalase as described in Armour et al. (*Diabetes* 39, 1519-1526 (1990)):

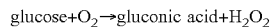
glucose+$O_2 \rightarrow$ gluconic acid+$H_2O_2$

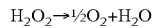
$H_2O_2 \rightarrow \frac{1}{2}O_2 + H_2O$ resulting in the overall enzyme reaction (when catalase is present):

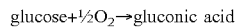
glucose+$\frac{1}{2}O_2 \rightarrow$ gluconic acid

In one specific implementation of the analyte-modulated detector element, the two enzyme types (GOx and catalase, each in an excess concentration) are immobilized within a gel matrix that is crosslinked for mechanical and chemical stability, and is in operative contact with the working electrode, which is configured to electrochemically sense oxygen. Glucose and ambient oxygen diffuse into the gel matrix and encounter the enzymes, the above reactions occur, and oxygen that is not consumed in the process is detected by the electrode. In embodiments based on "oxygen-sensing differential measurement" (i.e., comparison of an active detector element reading to a background (reference) detector element reading), after comparison of the active oxygen concentration reading with the background oxygen concentration reading, the difference is related to glucose concentration. Thus, hydrogen peroxide produced in the initial GOx catalyzed reaction is digested to oxygen and water via the subsequent catalase catalyzed reaction, and glucose concentration may be determined via detection of oxygen.

In an exemplary embodiment, the enzymatic material 240 comprises a crosslinked gel of hydrophilic material including enzymes (e.g., glucose oxidase and catalase) immobilized within the gel matrix, including a buffer agent and small quantities of a chemical crosslinking agent. The hydrophilic material 240 is permeable to both a large molecule component (e.g. glucose) and a small molecule component (e.g. oxygen). In various embodiments, specific materials useful for preparing the enzymatic material 240, include, in addition to an enzyme component, polyacrylamide gels, glutaraldehyde-crosslinked collagen or albumin, polyhydroxy ethylmethacrylate and its derivatives, and other hydrophilic polymers and copolymers, in combination with the desired enzyme or enzymes. The enzymatic material 240 can similarly be constructed by crosslinking glucose oxidase or other enzymes with chemical crosslinking reagents, without incorporating additional polymers.

The enzymatic material 240 is in operative contact with the working electrode 217 through the inner membrane 220 and the electrolyte layer 250 to allow for the electrochemical detection of oxygen at the working electrode 217 modulated by the two-step chemical reaction catalyzed by glucose oxidase and catalase discussed above. To that end, as glucose and ambient oxygen diffuse into the enzymatic material 240 from the outer (non-enzymatic) membrane 277, they encounter the resident enzymes (glucose oxidase and catalase) and react therewith; the oxygen that is not consumed in the reaction(s) diffuses through the inner membrane 220 and is detected at the working electrode 217 to yield a glucose-dependent oxygen signal. A similarly configured (excluding enzyme) background sensing element produces no reaction with diffused glucose, thereby resulting a glucose-independent oxygen signal.

A hydrophobic material is utilized for inner membrane 220, which is shown in FIG. 2A as being disposed over the electrolyte layer 250. The hydrophobic material is impermeable to the larger or less soluble molecule component (e.g. glucose) but permeable to the smaller or more soluble molecule component (e.g. oxygen). The inner membrane 220 can also be a continuous layer across the entire detector array surface, and thus be a single common layer utilized by all detectors in the detector array (assuming a multi-detector array is utilized). It is noted that the inner membrane 220, inter alia, protects the working electrode 217, reference electrode 218 and counter electrode 219 from drift in sensitivity due to contact with certain confounding phenomena (e.g. electrode "poisoning"), but the working electrode 217 will nonetheless be arranged sufficiently close to the enzymatic material to enable detection of oxygen levels therein.

The (hydrophobic) outer membrane shell 230 is disposed over at least a portion of the enzymatic material 240 (forming a cavity 271 within which the material 240 is contained), and is further configured to include an aperture within a "spout" region 270. It is contemplated that the inner membrane 220 and the membrane shell 230 can be coextensive and therefore be disposed as one continuous membrane layer in which outer membrane shell 230 and inner membrane 220 are of the same uniform thickness of membrane across the individual detector and array, although it will be appreciated that other thicknesses and configurations may be used as well, including configurations wherein the membrane shell 230 is separately provided and adhesively bonded to the inner membrane 220.

As depicted in FIG. 2A, the single spout region 270 of the (primary) detector element 206 forms a small opening or aperture 276 through the membrane shell 230 to constrain the available surface area of hydrophilic enzymatic material 240 exposed for diffusionally accepting the solute of interest (e.g. glucose) from solution. Alternatively, it is contemplated that one or more spout regions (and or apertures within a spout region) can exist per detector element.

The shape and dimension of spout region 270 aids in controlling the rate of entry of the solute of interest (e.g. glucose) into enzymatic material 240, and thus impacts the effective operational permeability ratio of the enzymatic material 240. Such permeability ratio can be expressed as the maximum detectable ratio of glucose to oxygen concentration of an enzymatic glucose sensor, where such a sensor is based on the detection of oxygen unconsumed by the enzyme reaction, and after taking into account the effects of external mass transfer conditions and the enzyme reaction stoichiometry. Detailed discussions of the relationship between membrane permeability ratio and the maximum detectable ratio of glucose to oxygen concentration of oxygen-detecting, enzymatic, membrane-based sensors are provided in "Model of a Two-Substrate Enzyme Electrode for Glucose," J. K. Leypoldt and D. A. Gough, *Analytical Chemistry*, 56, 2896 (1984) and "Diffusion and the Limiting Substrate in Two-Substrate Immobilized Enzyme Systems," J. K. Leypoldt and D. A. Gough, *Biotechnology and Bioengineering*, XXIV, 2705 (1982), incorporated herein by reference. The membranes of the exemplary detector element described herein are characterized by a permeability ratio of oxygen to glucose of about 200 to about 1 in units of (mg/dl glucose) per (mmHg oxygen). Note that while this measure of permeability ratio utilizes units of a glucose concentration to an oxygen concentration, it is nevertheless a measure of the ratio of oxygen to glucose permeability of the membrane.

As can be seen in FIG. 2B, an exemplary implantable sensor apparatus 300 includes a body 302 having a sensing region 304 disposed on a top surface 302a thereof. A plurality of sensing element pairs 306 are radially arranged and substantially evenly spaced apart within the sensing region 304. An analyte-modulated sensing element and a background sensing element are adjacent pairs of elements such that the arrangement will allow each analyte-modulated element in the pair to remain within the same relatively homogenous region (relative to its paired background element) of the otherwise heterogeneous tissue in which a sensor apparatus 300 is implanted.

It will be appreciated that the background or reference detector element (for each of the differential pairs 306) can have a substantially similar configuration to the analyte-modulated detector element 206. However, different from the analyte-modulated detector element, the background element excludes enzyme from the membrane or material disposed within the cavity (thereby making the element non-responsive to and/or affected by the presence of analyte). In such a configuration, the effective operational permeability ratio and diffusion rate of oxygen to the background detector element is expected to be similar to that of the analyte-modulated detector element. Accordingly, an expected response curve may be similar to that shown in FIG. 4A (discussed in detail infra), wherein delay is essentially identical (e.g., 0 sec) for each of the analyte-modulated and background detector elements, and the analyte-modulated detector element (e.g., such as Signal 1 having a lag of 15 sec shown in FIG. 4A) has a higher lag value than that of the background detector element (e.g., such as Signal 2 having a lag of 12 sec shown in FIG. 4A) in the presence of analyte (e.g., glucose).

In one exemplary implementation, the sensing element pairs 306 include selectively configured membrane elements and enzyme region shapes, which enable accurate detection of blood glucose level within the solid tissue of the host within desired blood analyte ranges and/or rates of response. The performance of the various detector elements (306a-306f) may be controlled through variation of one or more physical parameters of the membrane elements (e.g., dimensions, shapes, etc.), including an access or "spout" region, so as to allow for precise measurement of the target analyte. Control of response range and/or rate also permits easy "customization" of sensor elements, whether on a per-element or per-sensor apparatus basis. For example, the implantable sensor apparatus may comprise multiple heterogeneous detector elements with respective multiple ranges of sensitivity and/or rates of detection, thereby extending the dynamic range of the sensor apparatus (both in terms of analyte concentration and/or time, as desired). In such implementations, each pair of sensor elements may have a different temporal response relative to differential pairs of the sensor (e.g., different lag values requiring application of different time constants for temporal mismatch correction). The foregoing apparatus and methods of operation for sensor pairs having differing response ranges are discussed in detail in co-owned U.S. patent application Ser. No. 15/170,571, previously incorporated herein.

Turning now to FIGS. 3A-3C, in another exemplary embodiment, a sensor apparatus 400 comprises a housing 402 having a sensing region 404 disposed on a top surface 402a thereof. The sensing region 404 includes a plurality of grouped differential detector elements 406 (e.g., four groups of elements). In the illustrated embodiment of the sensor apparatus 400, the signal received from an analyte-modulated electrode is utilized to determine a ratiometric or differential signal relative to a plurality of background electrodes (two or more background electrodes) in order to determine a blood analyte concentration. Such a configuration for a glucose sensor advantageously reduces error in common-mode (background oxygen) signals due to the dispersed spatial arrangement of the background sensing elements relative to the glucose-modulated sensing element, and thereby increases overall accuracy of the sensor. The foregoing sensor element configurations are further disclosed in co-owned U.S. Provisional Patent Application Nos. 62/687,115 and 62/690,745, previously incorporated by reference herein.

Specifically, as can be seen in the detailed view shown in FIG. 3C, the exemplary group of sensing elements 406a includes multiple background sensing elements 408 (e.g., four background oxygen elements) associated with and proximate to a single analyte-modulated sensing element 410 (e.g., one glucose-modulated oxygen element). In alternate embodiments, the sensor face may in include additional or fewer groups of sensors, and/or additional or fewer background (oxygen) elements associated with each analyte-modulated (glucose) element. Additionally, in the embodiment shown in FIGS. 3A-3C, each of the sensor element groups has a configuration (discussed infra) which is substantially similar to other sensor groups; however, in alternate embodiments, the sensor elements within each group may have a different configuration/arrangement than that of the other groups (e.g., group 406b having a different configuration than group 406a).

Also shown in FIG. 3C, the four background oxygen elements each include a background oxygen (BO) working electrode 412 associated with a BO counter electrode 414. The BO counter electrodes 414 are substantially disposed at opposing lateral sides (proximate to an outer perimeter) of the sensing element group 406. The orientation of the BO counter electrodes toward the outer perimeter of the sensing element group enables a closer arrangement of the BO working electrodes to the glucose sensing element. Specifically, the BO working electrodes 412 are evenly-spaced and arranged around the glucose-modulated (GM) working electrode 422 (discussed infra) in a substantially square-shaped configuration, thereby enabling measurement of background oxygen generally within the same microenvironment as the GM electrode. Each of the BO working electrodes is disposed on a U-shaped filament 418, which is configured for association of each of the BO working electrodes 412 to a single (shared) BO reference electrode 420. The BO reference electrode 420 is proximate to the outer perimeter of the sensor group 406a and an outer perimeter of the sensor face. In alternate embodiments, each of the BO working electrodes may be associated with a separate BO reference electrode; however, utilization of a shared BO reference electrode advantageously enables a reduced size of the sensor face.

Also shown in FIG. 3C, the GM sensing element 410 comprises the aforementioned GM working electrode 422, a GM reference electrode 424, and a GM counter electrode 426. The GM electrode 410 is linearly arranged, where the GM counter electrode 426 is disposed proximate to a center of the sensor face, the GM reference electrode 426 is disposed proximate to the BO reference electrode 420, and the GM working electrode 422 is disposed therebetween (i.e., between the GM counter and reference electrodes). In the present embodiment, the GM working electrode 422 and reference electrode 424 are disposed between the arms of the U-shaped filament 418, while the GM counter electrode 4260 is outside of the filament. Similar to the orientation of the BO counter electrodes, such arrangement of the GM counter electrode enables a "closer" spatial arrangement or proximity of the GM working electrode to the BO working electrodes (with e.g., an approximate distance of 68 mils therebetween in one particular implementation, although this value may be varied in other implementations).

Figure 3D:
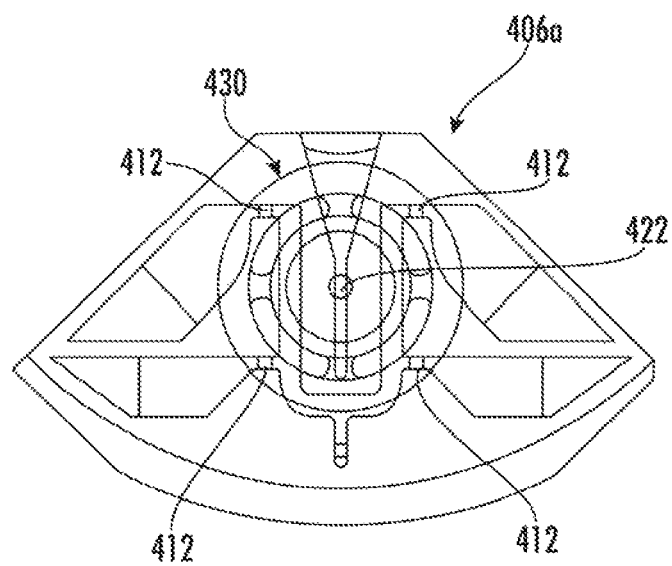
FIG. 3D is a top elevation view of an exemplary membrane structure for use with and overlaid on the detector element group of 3C.
Figure 3E:
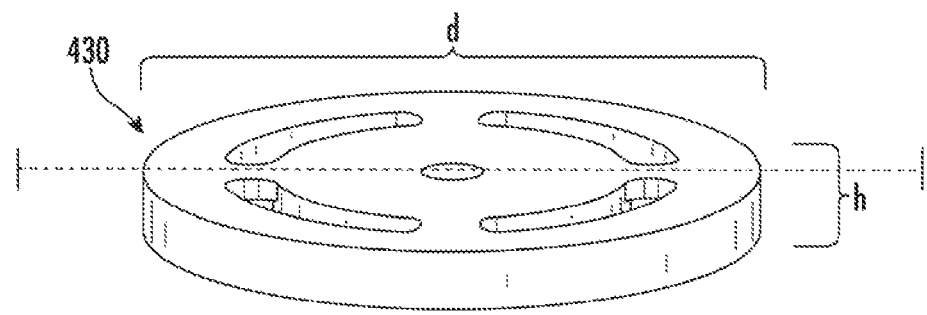
FIGS. 3E and 3F are, respectively, a front perspective view and a cross-sectional view of the exemplary membrane structure of FIG. 3D.
Figure 3F:
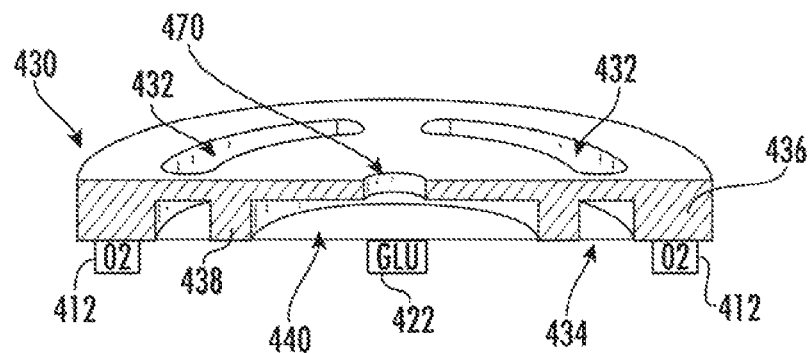

As shown in the exemplary configuration of FIG. 3D, an oxygen permeable membrane structure 430 is diposed on the sensor face 404 over at least a portion of the group of sensing elements 406a. As can be seen in FIGS. 3E and 3F, the membrane structure 430 (e.g., a silicone membrane structure) includes a substantially cylindrical and planar (i.e., disc-shaped) body of diameter d (in this embodiment, on the order of 0.16 inch) and a height h (in this embodiment, on the order of 0.02 inch). The exterior (i.e., non-bonded) face of the membrane structure comprises four outer (peripheral) openings 432 and a central opening (i.e., spout) 470. Each of the four outer openings communicates with a common channel 434 formed within the membrane structure, while the central opening 470 communicates with a central chamber 440 within the membrane structure.

The central chamber 440 is, in one embodiment, configured to be filled with enzyme material (e.g., glucose oxidase (GOX) and catalase enzymes immobilized within a cross-linked albumin (i.e., an "enzyme-embedded" membrane)), and aligned with an active face of the GM working electrode (as illustrated in FIG. 3C). Due to the reaction between glucose and oxygen in the presence of GOX, the glucose electrode senses glucose-modulated oxygen. The central opening or spout 470 of the membrane is, in one variant, configured to have cross-linked albumin or another such material disposed therein, thereby forming an exterior "enzyme-free" membrane, which retains or limits outward diffusion of reaction by-products (such as e.g., hydrogen peroxide) from the enzyme-embedded membrane and the central chamber 440. Outward diffusion of hydrogen peroxide is further limited via its consumption in the presence of the catalase enzyme. For example, the central chamber and enzyme-embedded and enzyme-free membranes may have the configurations and methods of formation similar to the membranes 240 and 277 discussed supra with reference to FIG. 2A, and/or the enzyme-embedded and non-enzyme membranes described in U.S. patent application Ser. Nos. 15/170,571 and 15/359,406, each previously incorporated herein.

As illustrated in FIGS. 3E and 3F, the membrane structure 430 further comprises a cylindrical ring 436 (an outer perimeter of the membrane structure) configured to be disposed over active faces of the four BO working electrodes (shown in FIG. 3F), and to enable diffusion of oxygen thereto while providing a electrical current barrier to protect surrounding tissue. Further, the cylindrical silicone ring 436 of the membrane 430 is physically connected to a central "riser" area 438 of the membrane structure (which defines the central chamber 440), thereby creating a single silicone membrane seat.

In one implementation, the outer periphery openings 432 and the channel 434 are filled with an oxygen-impermeable material (e.g., ceramic, a metallic material, etc.), and the oxygen-impermeable material limits diffusion of oxygen from an area of the central chamber 440 to the active face of the BO working electrodes.

In other implementations, the outer periphery openings 432 and the channel 434 are filled with an oxygen-permeable material (e.g., cross-linked albumin, silicone, etc.) or the membrane structure 430 excludes the outer periphery openings and the channel, and instead comprises a solid silicone structure between the cylindrical ring 436 and the central riser 438. In these latter implementations, due to (i) the close proximity between the GM working electrode and the BO working electrodes (discussed supra), and (ii) the absence of an oxygen diffusion barrier between the silicone ring and the central riser, the oxygen concentration at the silicone ring may be somewhat influenced by the relative amount of glucose concentration at the central chamber.

In any of the above implementations of the membrane structure 430, the permeability and diffusion rate of oxygen to the the background detector elements (i.e., BO working electrodes) is expected to be greater than that of the analyte-modulated detector element, as permeability of oxygen through the silicone material is greater than the permeability of oxygen through cross-linked protein material. In one example, solubility of oxygen in silicone is approximately 15 times greater than solubility of oxygen in cross-linked protein. Accordingly, an expected response curve may be similar to that shown in FIG. 4B (discussed in detail infra), wherein the analyte-modulated detector element (e.g., such as Sensor 1 having a delay of 5 sec and a lag of 15 sec shown in FIG. 4B) has higher delay and lag values than that of a background detector element (e.g., such as Sensor 2 having a delay of 0 sec and a lag of 12 sec shown in FIG. 4B) in the presence of analyte (e.g., glucose). Although not specifically shown, it will be appreciated that, in one implementation, each of the groups of sensing elements 406a-406d has a separate and similarly configured membrane structure associated therewith (such as, e.g., the membrane structure 430 shown in FIGS. 3D-3F). As the membranes are similarly configured in the foregoing implementation, a response curve for each of the groups of sensing elements is expected to be fairly similar to other groups (i.e., comprising similar delay and lag values).

In alternate implementations, each group may have a separate and differently configured membrane structure associated therewith (such as e.g., membrane structures each having a different spout size and shape and/or having a different exterior membrane size and shape disposed within the spout). In such implementations, the sensing element groups may each be configured to operate under a different optimal analyte concentration range as defined by e.g., spout diameter and shape and/or external membrane thereof for regulation analyte diffusion rate toward an active face of the analyte modulated working electrode. For example, various spout and membrane configurations which regulate diffusion rate are shown and described in co-owned U.S. patent application Ser. No. 15/170,571, previously incorporated herein.

In yet another implementation, a single (continuous) membrane structure may substantially cover all of the electrode groups. In the latter implementation, the configuration of various areas of the membrane structure which are each associated with one of the sensing element groups may be similar (e.g., similar spout diameters) or different (e.g., different spout diameters). For a sensor having different membrane configurations (e.g., different spout diameters) associated with the individual sensor groups (whether comprising separate membrane structures or a unitary membrane structure), the expected response curves may vary between the different groups of sensor elements (e.g., the analyte-modulated sensing elements may have different delay and/or lag values as compared to other groups).

Although not specifically depicted in FIGS. 2A-3F, each of the sensors 300 and 400 may include additional non-analyte sensors, such as temperature sensors, accelerometers, pressure sensors, pulse meters, chemical/ionic sensors (e.g., pH), etc. In one embodiment, signals from one or more of the additional non-analyte sensors may be evaluated against the analyte sensor signals and/or external blood analyte reference data in order to develop an operational model for the sensor or another device (e.g., a medicant pump) in data communication therewith. For example, problems with providing accurate blood analyte data can be due to a lack of an ability to account or correct for "unmodeled" variable errors. Further, error in a blood analyte sensor signal due to such unmodeled variables is often user-specific and/or only determinable in vivo (i.e., after implantation of the sensor). Such disabilities can be mitigated or even completely eliminated via personalized and dynamic detection of blood analyte level and compensation for associated errors, including when the sensor is implanted within the user, via in vivo development of a sensor operational model for use during analyte detection.

For example, the sensor apparatus may employ (i) a training mode of operation, whereby the apparatus (or processing logic associated therewith, whether on-board or off-board) conducts "machine learning" to model one or more errors (e.g., unmodeled variable system errors) associated with the blood analyte measurement process, and (ii) generation of an operational model (based at least in part on data collected/received in the training mode), which is applied to correct or compensate for the errors during normal operation and collection of blood analyte data, thereby enhancing device signal stability and accuracy over extended periods of implantation, including through in situ "personalization" of the sensor apparatus via the aforementioned training mode and subsequent operational model generation.

In one implementation, the implantable sensor (e.g., an oxygen-based sensor for detection of blood glucose level) and/or an associated receiver apparatus are configured for operation in a "training mode" after implantation of the sensor. During operation in the "training mode", the sensor system collects and calculates time-stamped blood analyte level data ($BA_{cal}$ data), and receives external time-stamped blood analyte level reference data ($BA_{ref}$ data) such as e.g., blood analyte data obtained from "fingersticking", or other laboratory or in situ testing. The system may additionally collect and utilize other non-$BA_{cal}$ data, such as e.g., data collected from each of the other sensors (non-analyte sensors), non-$BA_{cal}$ data collected from the implanted sensor, and/or data input by a user or medical professional.

After collection of a statistically relevant amount of data, the blood analyte reference data and the calculated blood analyte level data are utilized to calculate blood analyte error data ($BA_{error}$ data), and one or more parameters (e.g., time of day, range of the target blood analyte concentration, temperature, sensor element or origin, heart rate, motion, pressure exerted on the implanted sensor, other blood analyte concentrations, other sensor detector signals or features thereof, such as for example first or second derivatives of sensor signals, or measures of sensor signal variability) which have a high correlation to blood analyte error are identified via application of one or more "machine learning algorithms." This information is used to generate a user-specific operational model, which is subsequently utilized during normal operation of the sensor system in an analyte detection and reporting mode to predict error due to unmodeled system variables (i.e., user and/or context-specific variables). Thus, the output blood analyte level readings advantageously account and/or correct for the predicted unmodeled variable error (and, in some examples, random noise error), thereby providing significantly improved accuracy in terms of, e.g., mean absolute relative difference (MARD) between the sensor output and a comparison or calibrated measurement, or by the frequency of outliers in such comparisons or calibrations, as compared to conventional implantable blood analyte sensor systems. The foregoing apparatus and methods for sensor operational model generation are discussed in detail in co-owned U.S. patent application Ser. No. 15/645,913, previously incorporated by reference herein.

Additionally, many of the above-described disabilities in providing accurate blood analyte data carry over into automatic calculation of an appropriate amount, time, and/or rate for medicant delivery based on blood analyte data are due to a lack of an ability to account or correct for otherwise "unmodeled" variable errors in calculation of medicant dosing data (as well as calculation of blood analyte data) which occur when implanted sensors and associated implanted or non-implanted medicant pumps (or even non-pump medicant delivery mechanisms) are utilized in vivo. Further, similar to blood analyte sensor data, the error in medicant dosing data due to such unmodeled variables is often user-specific and/or only determinable after implantation of the sensor and/or pump. Such disabilities can addressed via personalized and dynamic calculation of medicant dosage and/or compensation for associated errors when the pump is activated and utilized (whether partially implanted, fully implanted, or non-implanted) by the specific user, in addition to the above described personalized and dynamic detection of blood analyte level and compensation for associated errors when the sensor is implanted within the user.

Accordingly, in another implementation, an exemplary implantable sensor and pump system comprises employs receipt of accurate blood analyte data (e.g., corrected sensor data from a processing apparatus associated with an implanted sensor, or reference blood analyte data from an external source, such as blood analyte levels obtained by fingersticking) at a processing apparatus which controls the pump. The received corrected sensor data and/or reference blood analyte data are utilized by the pump during a training mode of operation, whereby the processing apparatus associated with the pump (or processing logic associated therewith, whether on-board or off-board) conducts "machine learning" on analyte data and non-analyte data (e.g., time of day, range of the target blood analyte concentration, temperature, sensor element or origin, heart rate, motion, pressure exerted on the implanted sensor, other blood analyte concentrations, other sensor detector signals or features thereof, such as for example first or second derivatives of sensor signals, or measures of sensor signal variability, other pump characteristics, such as for example a medicant reservoir fill level, medicant flow characteristics, etc.) to model one or more unmodeled variable system errors associated with the medicant dispensement data calculation, and generation of a pump error correction operational model (based at least in part on data collected/received in the training mode), which is applied to correct or compensate for the errors during an auto-dispense mode operation of implanted pumps or an auto-calculate mode operation of non-implanted pumps or other manual medicant delivery mechanisms. The foregoing apparatus and methods for medicant delivery operational model generation are discussed in detail in co-owned U.S. patent application Ser. No. 15/853,574, previously incorporated by reference herein.

In each of the exemplary embodiments discussed supra, any signals from associated non-analyte sensors (such as temperature sensors, accelerometers, pressure sensors, pulse meters, chemical/ion sensors, etc.) utilized for collection of parameter data may have temporal mismatch (i.e., delay and/or lag) relative to the analyte sensor elements, thereby affecting accuracy of the operational models utilizing the non-analyte sensor signals. Accordingly, in one salient aspect of the present disclosure, application of the temporal mismatch correction methods and apparatus disclosed herein can be advantageously be utilized to correct or compensate for signal delay and/or lag not only in differentially paired or grouped analyte-modulated and background sensors, but also to correct for signal delay and/or lag of non-analyte sensors associated therewith. Correction of temporal mismatch between the analyte and non-analyte sensor elements can improve accuracy of the foregoing sensor and/or medicant delivery operational models.

Exemplary methods and apparatus for temporal mismatch correction for use with the above described exemplary sensor elements are discussed in detail below.

Model Generation and Transformation

As noted above, one aspect of the present disclosure comprises generation and utilization of a model that characterizes the differences in the time responses of different electrodes (e.g., two electrodes of a differential sensing pair, two or more electrodes in an associated differential group, or other types of (non-analyte) sensors associated with a differential pair or group), and applies this characterization to temporally align the different signals. For example, in the exemplary oxygen-based blood glucose sensor described herein, the temporal responses of the different electrodes (analyte and background oxygen) are characterized as a function of glucose to oxygen concentration ($C_g/C_o$) for different thicknesses of bulk layer (i.e., different thicknesses of a substantially stagnant fluid region immediately surrounding the sensor face, such as e.g., a stagnant solvent layer in an in vitro environment or a stagnant blood and other bodily fluid layer in an in vivo environment). Predictable dead-time and/or time constants associated with each of the two electrodes are used within an algorithmic framework in order to correct or reconcile the temporal response (delay and lag) mismatch between the two (or more) electrodes, and thereby enable more accurate computation of glucose through the differential (ratiometric) computational methods applied to the signals from the electrodes.

Figure 4A:
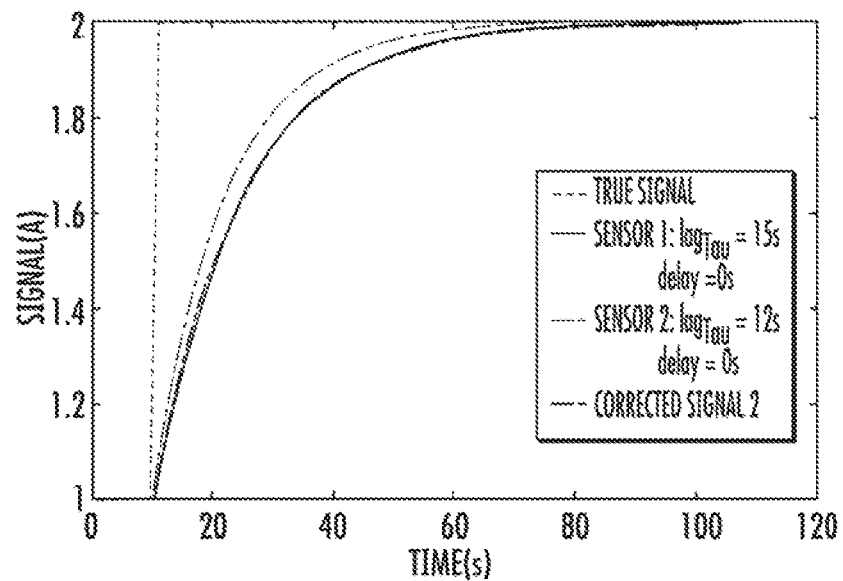
FIG. 4A is a first graphical representation of an exemplary algorithmic transformation to correct for lag of the signal from Sensor 2, so as to match the signal of Sensor 1, according to one embodiment of the present disclosure.

FIG. 4A (discussed supra) illustrates the application of one such correction, where a signal from Sensor 2 (generated by e.g., one or more background detector elements) is mathematically transformed so that it more closely matches the response of Sensor 1 (generated by e.g., an analyte modulated detector element) to correct for lag of Sensor 1. Specifically, the native Sensor 1 signal has a $lag_{Tau}$ of 15 sec (and a delay of 0 sec), while the native Sensor 2 signal has a $lag_{Tau}$ of 12 sec (and a delay of 0 sec). Via application of a temporal mismatch correction algorithm, the Sensor 2 signal is corrected or adjusted to a $lag_{Tau}$ of 15 sec such that the lag value thereof matches that of Sensor 1.

Figure 4B:
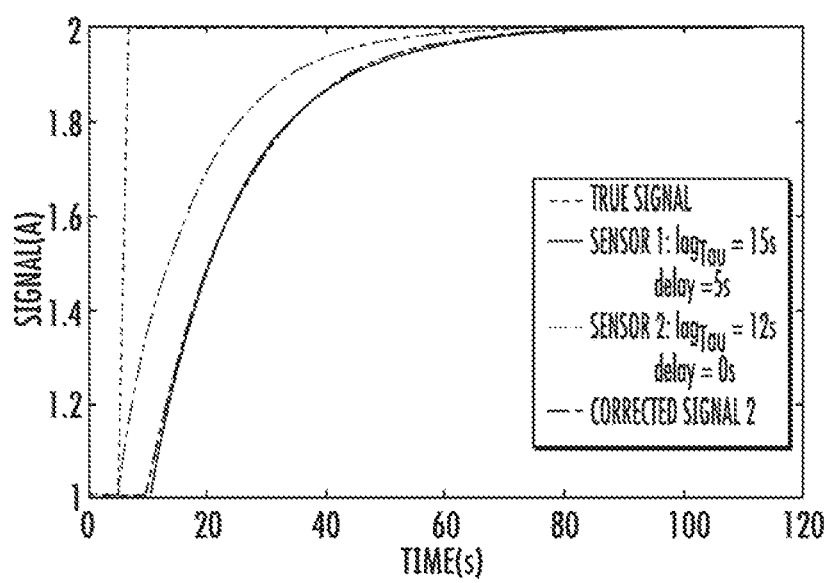
FIG. 4B is second graphical representation of an exemplary algorithmic transformation to correct for delay and lag of the signal from Sensor 2, so as to match the signal of Sensor 1, according to another embodiment of the present disclosure.

FIG. 4B (discussed supra) illustrates the application of another such correction, where a signal from Sensor 2 (generated by e.g., one or more background detector elements) is mathematically transformed so that it more closely matches the response of Sensor 1 (generated by e.g., an analyte modulated detector element) to correct for delay and lag of Sensor 1. Specifically, the native Sensor 1 signal has a $lag_{Tau}$ of 15 sec and a delay of 5 sec, while the native Sensor 2 signal has a $lag_{Tau}$ of 12 sec and a delay of 0 sec. Via application of a temporal mismatch correction algorithm, the Sensor 2 signal is corrected or adjusted to a delay of 5 sec and a $lag_{Tau}$ of 15 sec such that the delay and lag values thereof match those of Sensor 1.

Notably, the "true" or actual analyte values in FIGS. 4A and 4B (here respectively modeled as a step response) are only approximated by the Sensor 1 and (transformed) Sensor 2 curves, due to the inherent temporal response (delay and lag) of the detector electrodes. However, by aligning or reconciling the differing temporal responses of the two sensor elements, more accurate determination of analyte (blood glucose) level is possible, since it is derived from the combined measurements (differential, ratiometric, etc.) of the paired sensor elements. Stated differently, temporal synchronization of the two signals permits more accurate analyte concentration determination, since the conditions reported by each temporally-synchronized sensor element corresponds (temporally) to the conditions reported by the other sensor element, rather than attempting to compare or utilize one output which is time-delay and/or time-shifted (or time-lagged) from the other in terms of actual physiologic conditions.

It will be appreciated that while the foregoing examples (and other embodiments described herein) apply a transformation from one sensor element with a smaller temporal delay and/or lag (e.g., Sensor 2) in order to temporally align or reconcile it to the other electrode having a greater temporal delay and/or lag (e.g., Sensor 1) of a differential pair, the various aspects of the present disclosure are in no way limited to: (i) transformation of the earlier or less latent signal to "match" the more latent signal; in fact, the opposite transformation (e.g., from Sensor 1 to Sensor 2 in the foregoing example) may be made (and may, in certain implementations, obviate one or more processes such as "de-noising" of the raw signals prior to application of the transformation); (ii) differential pairs of sensor electrodes; for instance, the aforementioned correction(s) may be applied to multiple "reference" electrodes associated with a single sensing electrode (e.g., Sensor 1, Sensor 2, Sensor 3, Sensor 4, and Sensor 5, wherein Sensors 2-5 are reference electrode signals each with unique or differing temporal response and hence different transformations relative to Sensor 1 of the analyte-modulated sensing electrode, such as in the exemplary sensor apparatus 400 shown in FIGS. 3A-3D); or (iii) identical or similar types of electrodes. For example, a peroxide-based sensing electrode as well as an O2-based differential pair of sensing electrodes may be utilized in a sensor assembly. The glucose signal reported by the peroxide-based electrode of such sensor assembly may have different lag/delay in comparison to the glucose signal reported by the O2-based sensor (due to, for example, factors inherent in their respective sensing mechanisms, such as, e.g., different enzyme formulations, different membrane structure and/or material properties, etc.). Therefore, the glucose measurements from the two sensors/electrodes could be temporally aligned according to the techniques described herein before being combined (by e.g., weighted average, Kalman filter based fusion, etc.) to obtain a more robust estimate.

In another exemplary embodiment, if one or more analyte-modulated sensor elements and/or background sensing elements is dependent on the operating temperature of the sensor (or another factor or combination of factors, such as those discussed supra utilized for sensor operational model generation and application), a temperature sensing element can be included in the sensor. The temperature sensing element may introduce its own characteristic combination of lag and delay while measuring the sensor temperature. In such a scenario, temporally aligning the temperature with the analyte-modulated and/or background measurement will allow the application of correct calibration parameters and/or correction of unmodeled systemic error, advantageously resulting in lower measurement error.

In Vitro Modeling Methods

Figure 5A:
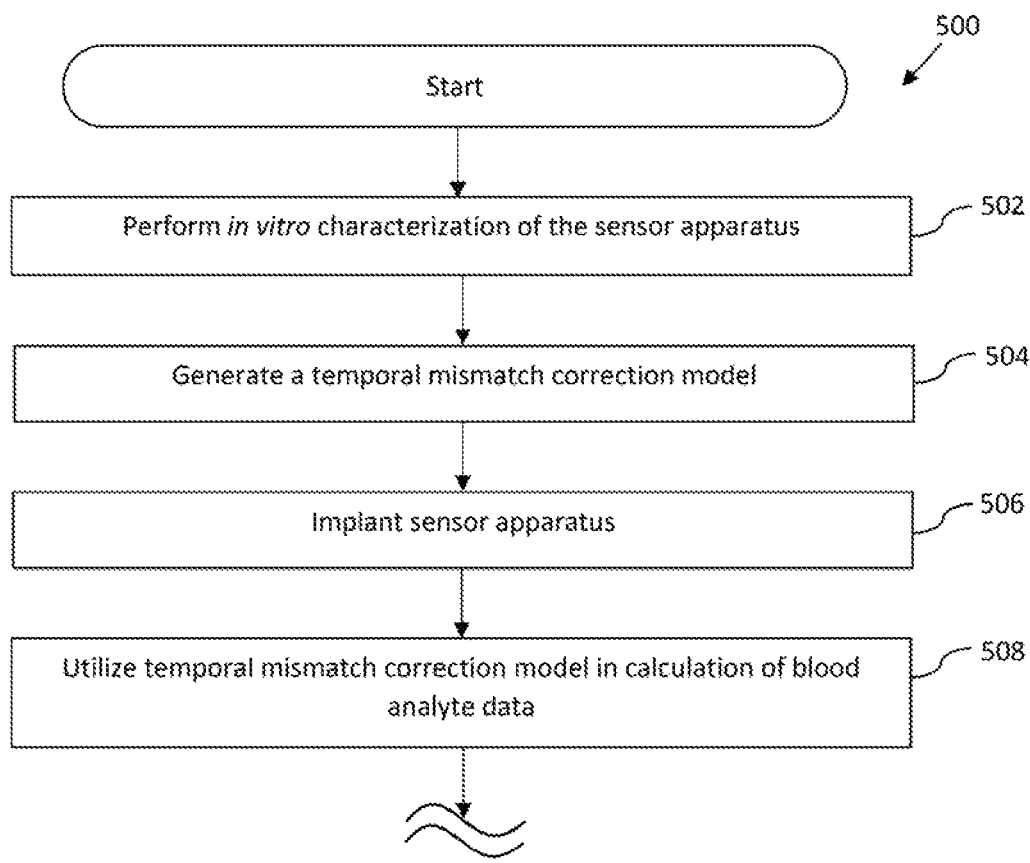
FIG. 5A is a logical flow diagram representing an exemplary generalized method of temporal mismatch correction, according to one embodiment of the present disclosure.

Turning now to FIG. 5A, an exemplary generalized method 500 for in vitro characterization and temporal mismatch correction between associated sensing element/detector signals (and subsequent sensor implantation) is shown and described. First, at step 502, an in vitro characterization of the sensing elements of the sensor apparatus is performed. Based at least in part on the in vitro characterization, a temporal mismatch correction model is generated, per step 504. The sensor apparatus is then implanted in a subject (step 506), and the previously generated temporal mismatch correction model is utilized for determination of blood analyte data (and/or data related to other physiological parameters, at step 508.

Figure 5B:
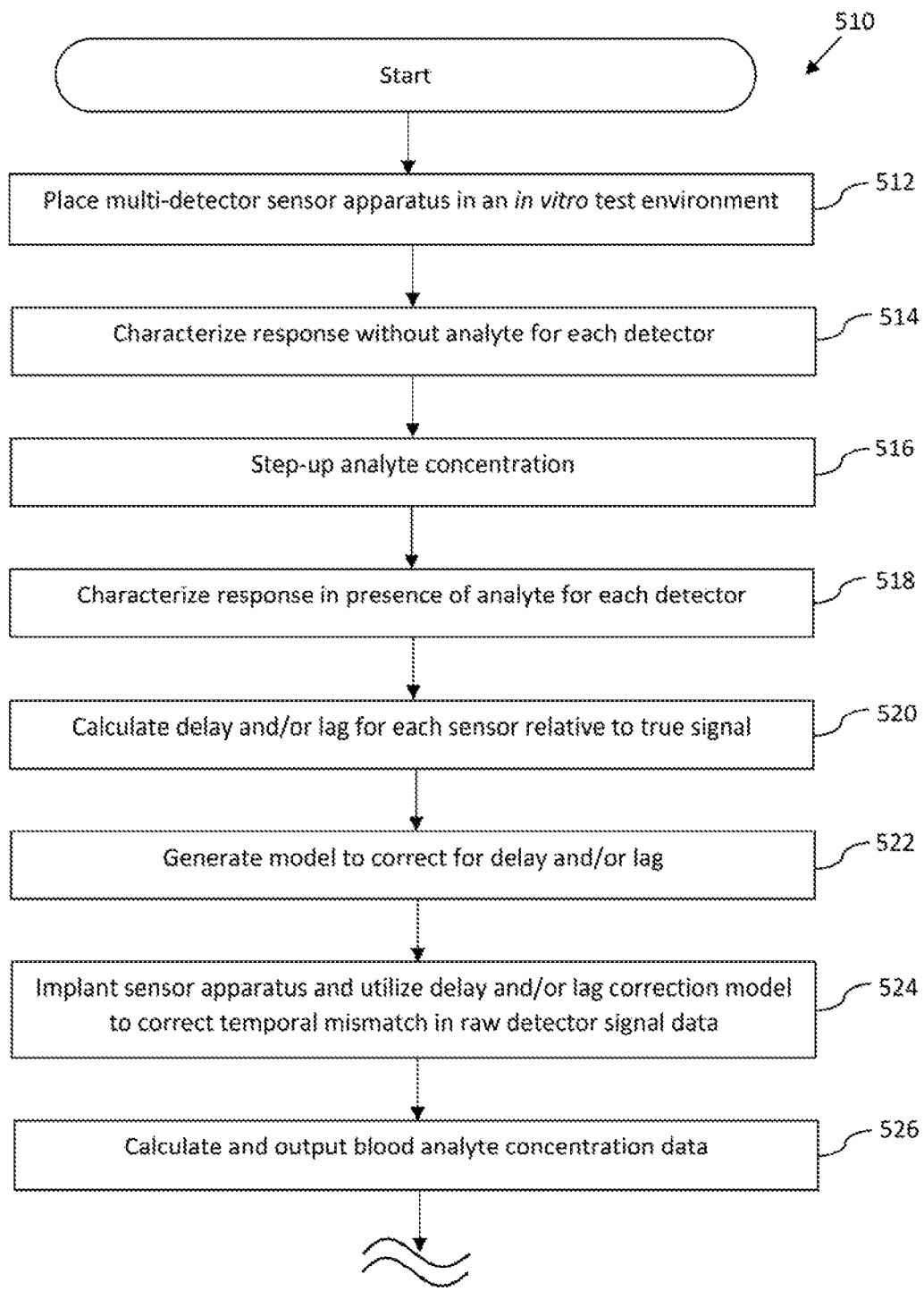
FIG. 5B is a logical flow diagram illustrating one particular implementation of the method of FIG. 5A.

Referring now to FIG. 5B, one specific implementation of the generalized method 500 of FIG. 5A is shown. First, at step 512 of the method 510, a multi-detector sensor apparatus (such as one of the exemplary sensor apparatus discussed supra) is placed in an in vitro testing environment. For example, the sensor apparatus is mounted or otherwise stably positioned in a buffer fluid, such as a mixture of: high purity deionized water (19 L), sodium chloride (110 g), Potassium Phosphate Monobasic (5.4 g) and anhydrous Potassium Phosphate Dibasic (41.3 g).

Next, per step 514, the oxygen step response, without the presence of analyte, is characterized for each of the reference and analyte-modulated detectors. Specifically, in the test regime, in addition to the analyte-modulated and background sensing elements discussed supra, one or more "bare" (i.e. lacking any membranes) electrodes are included in the sensor apparatus to allow the measurement of true pO2 during the test without introducing significant delay or lag. In other words, delay (dead time) as well as a lag (i.e., due to time constant) of signals of the glucose and oxygen electrodes (in response to the oxygen step) are characterized via comparison to the signals of the bare electrodes. Per steps 516 and 518, each of the detectors is similarly characterized via analyte (glucose) step response.

Similarly, the non-analyte sensor elements, such as a temperature sensor, can be characterized by including a known reference system in the in vitro testing environment. For example, a commercial-off-the-shelf (COTS) temperature probe of known transient specification can be included to measure the true temperature during in vitro characterization. Delay (dead time) and lag (i.e., due to time constant) of signals of the on-board temperature sensor (e.g., an on-board temperature sensor of the Model 100 Sensor or an on-board temperature sensor of the Gen 3 Model Sensor), as well as glucose-modulated and background oxygen electrodes (in response to the temperature step) are characterized via comparison to the signals of the COTS temperature sensor.

The in vitro test data is then utilized to calculate time constants (lag) and dead-time (delay) for each of the sensing elements (step 520), and a model is generated to correct for temporal mismatch (delay and/or lag) between the sensor elements (step 522). Per step 524, the characterized sensor apparatus or a same class of sensor apparatus (a sensor having e.g., an identical or similar membrane configuration for each of its sensing elements, an identical or similar spatial arrangement of the sensing elements, and an identical or similar sensor element composition to the in vitro tested sensor) is implanted in a subject, such as via the implantation methods described in co-owned U.S. patent application Ser. No. 14/982,346, previously incorporated herein. As a brief aside, any "bare" sensor elements are excluded from or are not active an implanted sensor in order to protect the surrounding tissue from e.g., exposure to active electrical currents.

After implantation, the temporal mismatch correction model and the determined dead-time and time constant values are utilized to transform or match associated raw detector signals/data for use in sensor apparatus calculations, such as calculation of a blood analyte level and/or a rate of change (ROC) of blood analyte. Per step 526, one or more values of interest determined from the temporal mismatch corrected data are output to a receiver apparatus (e.g., a user's smart phone) or another communicative device (e.g., a medicant pump and/or its associated receiver apparatus).

It will also be appreciated that the foregoing analysis can be performed indigenously or substantially autonomously (i.e., within the sensor element and its onboard logic itself), and/or "off-board," such as via processing power and algorithms operative to run on an external receiver, parent platform (e.g., user smartphone), and/or cloud server apparatus in data communication with the (implanted) sensor.

Exemplary analytical framework, specific test parameters, and calculations for the above generalized in vitro methods 500 and 510 are discussed in detail below.

Analytical Framework

Figure 8:
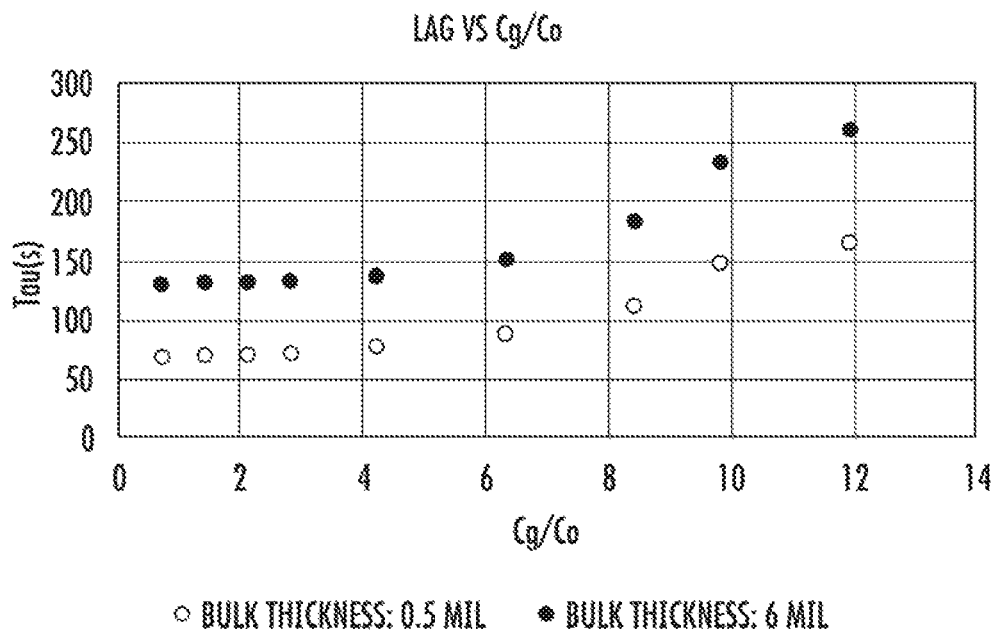
FIG. 8 is a graphical representation of a time constant (s) vs Cg/Co of an exemplary glucose electrode at two different bulk layer thicknesses, as simulated using COMSOL®, according to one embodiment of the present disclosure.

For the exemplary analysis, the temporal responses of glucose and oxygen electrodes in an oxygen-based differential electrode pair (i.e., that of the exemplary Model 100 fully implantable blood glucose sensor manufactured by the Assignee hereof) were simulated, when subject to a step-change in oxygen concentration at different bulk layer thicknesses and Cg/Co conditions (see FIG. 8). Data from controlled in vitro experiments with Model 100 sensors were also obtained and utilized in conjunction with COMSOL-based simulations (COMSOL Multiphysics® Version 5.3) to identify an approximate mathematical model (e.g., First Order Plus Dead-Time: FOPDT) for the step response. It is noted in passing that computer simulation with the COMSOL commercial software package is a recognized standard in finite element/volume modeling, although it will be appreciated that other simulation packages may be used with equal success.

The exemplary embodiment of the mathematical model-based theoretical solution was used to transform the response of an oxygen reference or background electrode (having a faster response/smaller time constant) to a larger time constant (i.e., an approximated time constant of a Cg glucose-sensing electrode).

The exemplary algorithm further assumes a uniform concentration of molecular species at the outer surface of a uniformly-thick bulk layer around each electrode, although more complex concentration and bulk layer modeling may be used consistent with the disclosure with proper adaptation, by those of ordinary skill given the present disclosure.

The response of the electrodes for a step-change in oxygen concentration (as in FIG. 7) was modeled to be sigmoidal in nature. Therefore, the system was modeled as a higher-order overdamped system, and the sigmoidal response approximated as a First Order Plus Dead Time (FOPDT) in the exemplary embodiment. The FOPDT parameters (time constant and dead-time) of a given electrode for a step-up vs. step-down were observed to be approximately equal, although the present disclosure contemplates cases where the foregoing are not equal in time constant (lag) and/or dead time (delay), and may be modeled accordingly. For example, a first transformation model can be generated for a step-up scenario, while a second transformation model can be generated for a step-down scenario. After implantation of the sensor (such as in steps 514 and 516 of method 500 discussed supra), each of the first and second transformation models can be alternatively applied depending on an in vivo condition (i.e., one of a step-up condition and a step-down condition).

Moreover, the FOPDT parameters of the Model 100's O2 electrode were modeled as a function of equivalent bulk layer thickness, while the FOPDT parameters of the Model 100's Cg electrode were modeled as a function of both (i) equivalent bulk layer thickness, and (ii) Cg/Co. At a constant equivalent bulk layer thickness, the time constant increases with an increase in Cg/Co (FIG. 9), whereas dead-time only shows a very small change.

In the exemplary analysis, at a constant bulk layer thickness, Cg and O2 electrodes have comparable dead-time and, therefore, the time delay in their response is assumed to be matched, although the present disclosure also contemplates cases where the dead-times (time delay) are not matched between the electrode pair, and may be corrected accordingly in addition to the lag correction (such as in the example shown in FIG. 4B).

Test Conduct and Procedures

Figure 6A:
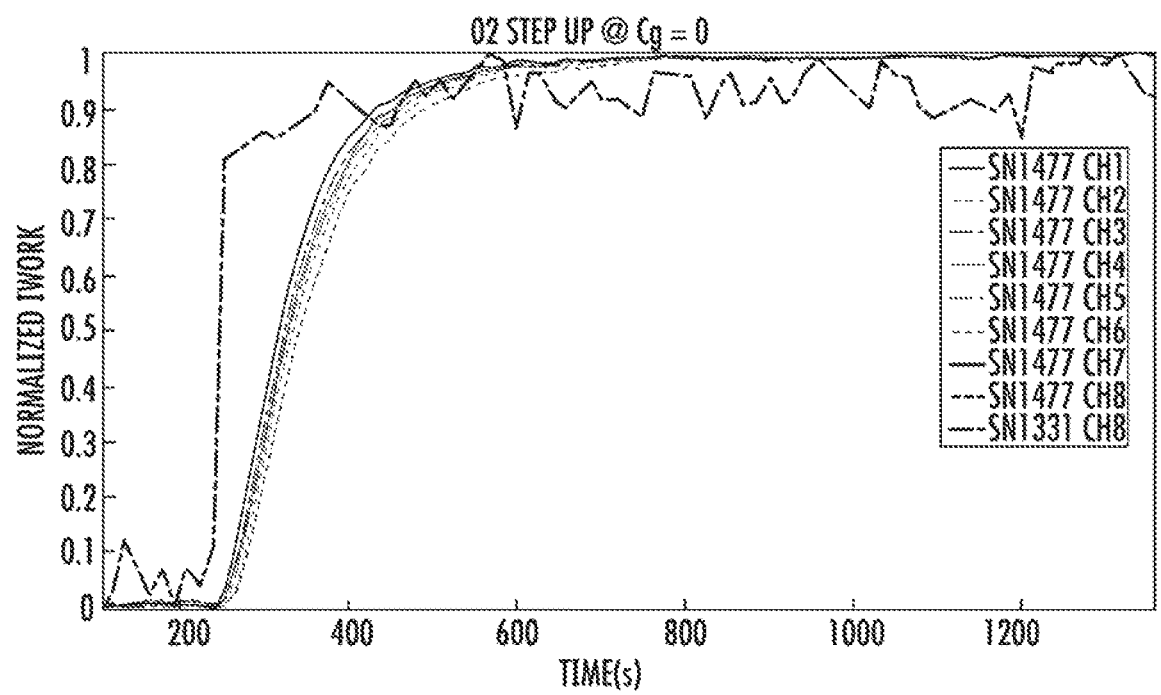
FIG. 6A is a graphical representation of $O_2$ step-up at Cg=0 and $O_2$=2% to 2.4%, according to one embodiment of the present disclosure.
Figure 6B:
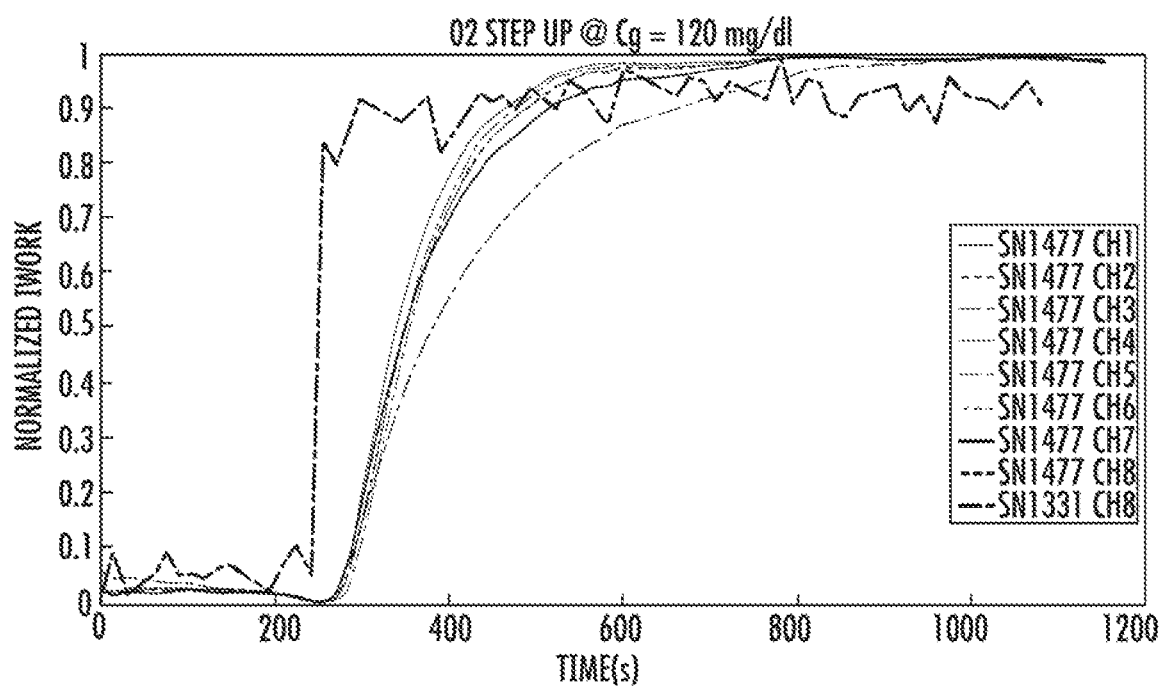
FIG. 6B is a graphical representation of $O_2$ step-up at Cg=120 and $O_2$=2% to 2.4%, according to one embodiment of the present disclosure.

The sensors were prepared and placed in vitro to characterize the oxygen step response for each of the reference and analyte electrodes. Specifically, in the test regime, one "bare" (i.e. lacking any membranes) electrode (ch8) was utilized from Sensor SN009001331, to allow the measurement of true pO2 during the test without introducing significant delay or lag (FIGS. 6A and 6B). All the sensors were configured to sample and transmit data every 15 seconds.

As part of the in vitro testing, the steps in oxygen were performed from 2% O2 to 2.4% O2 at both Cg=0 and Cg=120 mg/dl. The measured currents (Iwork) for each channel (for each step) were normalized to transition between 0 and 1 during the step as shown in FIG. 6A. Specifically:

$$\text{Normalized\_Iwork} = (\text{Iwork}(t) - \text{min\_Iwork}) / (\text{max\_Iwork} - \text{min\_Iwork}) \quad \text{Eqn. (1)}$$

where:
min_Iwork=Minimum recorded steady-state Iwork seen immediately prior to the step; and
max_Iwork=Maximum recorded steady-state Iwork reached after the step.

Test Results and Data

Utilizing the analytical framework and test procedures/setup described above, the following results were obtained by the Assignee hereof.

Specifically, as shown in FIG. 6A (O2 step-up at Cg=0 and O2=2% to 2.4%), the glucose and oxygen electrodes showed a delay (dead time) as well as a lag (i.e., due to time constant) in their response to the oxygen step when compared to the bare electrodes (i.e., those of Sensor SN009001331). As shown in FIG. 6A, delay (dead time) is the time elapsed between the change in current at the bare electrode (black dashed line, at time 225 sec) to the beginning of change in currents at the other specified electrodes (at time 250 sec). Similarly, lag is the time elapsed during the transitioning of the non-bare electrode's current from one steady-state (Normalized 0) to the other steady-state (Normalized 1). When glucose was present, the lag was observed to be the largest for Channel 3 (glucose electrode) followed by the oxygen electrodes (i.e., the reference or background electrodes, without enzyme), as shown in FIG. 6B herein (O2 step-up at Cg=120 and O2=2% to 2.4%).

The ratio Cg/Co (within an electrode's enzyme-containing membrane) can also be defined/measured using another parameter $I/I_0$, where I is the glucose-modulated current measured at the electrode under a specified condition, and $I_0$ is the expected current measured under the same specified condition but at zero glucose concentration. As an example, since the oxygen electrode does not respond to the presence of glucose, measured $I/I_0$ for an oxygen electrode is always expected to be 1 under all conditions. Similarly, in a glucose electrode, the glucose-modulated current decreases with an increase in glucose while other conditions are kept constant (constant pO2, temperature, etc.), leading to lower $I/I_0$ at higher glucose concentrations. As evidenced by the responses seen in FIG. 6B compared to the responses seen in FIG. 6A, as the value of the ratio 140 decreased (i.e., Cg/Co increased), a higher lag was observed in the glucose electrode.

As discussed supra, the given relationships described above may change as a function of different constructions of the electrode(s), such as for example where a different "spout" size (i.e., aperture configuration for permeation of glucose molecules to the components of the sensor element), and/or other spatial characteristic of the membrane structure, and/or a different membrane composition (e.g., silicone vs. crosslinked albumin) is utilized. Even under such variations in construction, however, the methodology described above advantageously remains applicable and may be accordingly adapted by those of ordinary skill given the present disclosure.

Next, COMSOL model parameters were updated/validated to match the results from in vitro experiments discussed above. Specifically, to characterize the oxygen transient response of the sensor electrodes at different operating conditions, an equivalent COMSOL model for the sensor electrodes was developed. As shown in Table 1, the COMSOL model substantially matched (within an acceptable variation) in vitro results from Model 100 sensors with respect to the O2 step rise-time at different Cg/Co conditions.

TABLE 1 in vitro experiment @ O2 step = 2% to 2.4%

| Channel | In vitro Results | | COMSOL Results (Bulk: 1.5 mil) | |
|---|---|---|---|---|
| | Time to 63% @ Cg = 0 | Time to 63% @ Cg = 120 | Time to 63% @ Cg = 0 | Time to 63% @ Cg = 120 |
| O2 | 136 s | 136 s | 134 s | 134 s |
| Cg | 117 s | 189 s | 116 s | 183 s |

Figure 7:
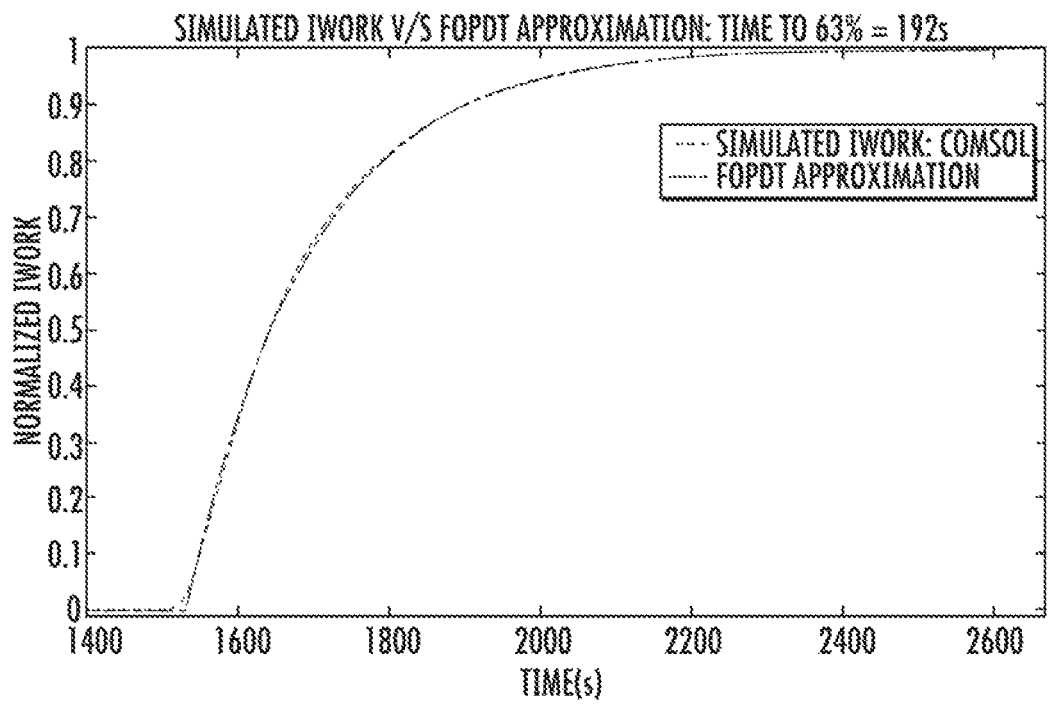
FIG. 7 is a graphical representation of a COMSOL®-simulated sensor response to a step change input vs. a First Order Plus Dead-Time (FOPDT) approximation for an exemplary electrode configuration, according to one embodiment of the present disclosure.

The step response of the sensors' electrodes was observed to be a sigmoid, typical of a higher-order overdamped system. A First Order Plus Dead-Time (FOPDT) model is often utilized to approximate the sigmoidal responses of a higher order system, and hence in the exemplary embodiment, an FOPDT model was utilized to characterize the delay (dead-time) and lag (due to the time constant) observed in the sensor electrodes. As shown in FIG. 7 herein, a MATLAB®-based FOPDT approximation provided a good fit to the sensor response simulated using COMSOL.

Further analysis of the effect of Cg/Co (I/I$_0$) on dead-time and time constants of the O2 and Cg electrodes was also conducted. As shown in Table 2, the dead-time (delay) of the sensor electrodes differed by only 7 sec as I/I$_0$ decreased from a value of 1 (unity) to a value of 0.15. However, the lag (as represented by the time constant) of the sensor electrodes changed by ~37 sec between the same conditions. Therefore, the temporal mismatch between the oxygen and glucose electrodes is assumed to be primarily due to the time constant mismatch at different levels of Cg/Co, whereas the pure delay aspect (i.e. the dead-time) is considered to be well-matched (within an acceptable range of variation).

TABLE 2

COMSOL simulation results for O2 step (2% to 2.4%) at Cg = 120 mg/dl (I/I$_0$ = 0.15)

| Channels | Dead-time (s) | Time Constant (s) |
|---|---|---|
| O$_2$ Electrode | 45 | 87 |
| Cg Electrode | 52 | 124 |
| Difference (Cg − O2) | 7 | 37 |

Figure 9:
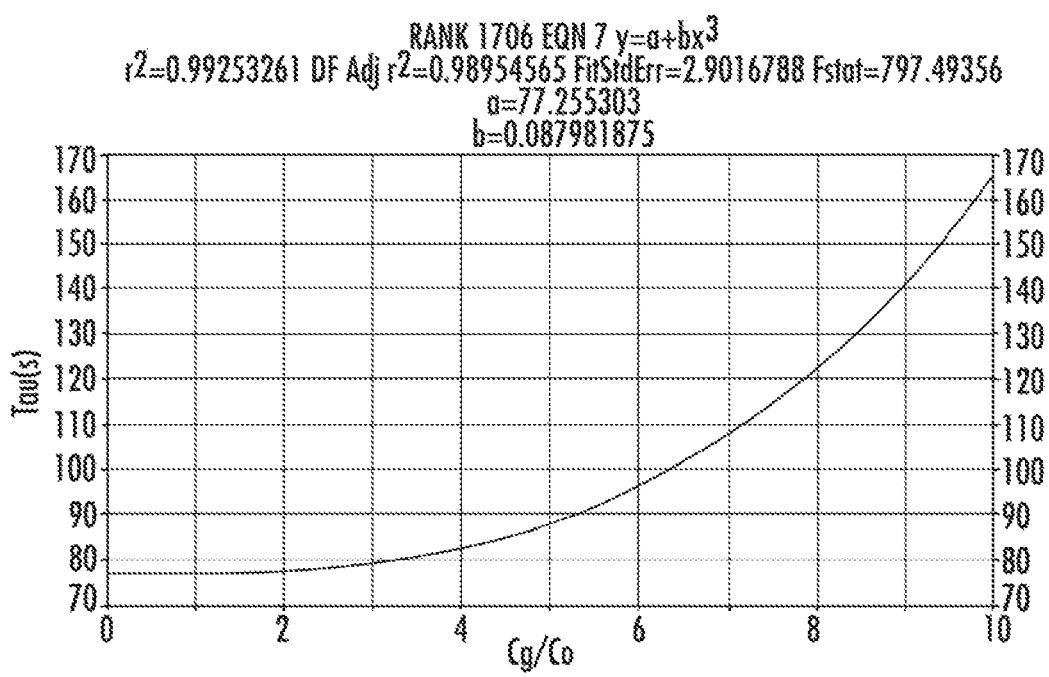
FIG. 9 is a graphical representation of a time constant fit as a function of Cg/Co yielded r2=0.99, according to one embodiment of the present disclosure.

Additionally, an oxygen step simulation at various Cg/Co and bulk layer thicknesses was conducted; i.e., to assess the lag (owing to time constant) vs. Cg/Co at different bulk layer thickness values. Specifically, oxygen steps were simulated in COMSOL for a matrix of operating conditions comprising different oxygen, glucose and bulk layer thickness parameters. FIG. 8 herein shows the estimated time constants calculated for a representative glucose electrode at different Cg/Co conditions and at two bulk layer thicknesses of 0.5 mils and 6 mils. The observed results show, inter alia, a possible functional form-based dependence between glucose electrode time constant and Cg/Co at a fixed equivalent bulk layer thickness. Moreover, as shown in FIG. 9, a cubic function (y=a+bx$^3$ in the illustrated example) provides a good fit for the time constant (Tau) as a function of Cg/Co values; as noted, such functional model yielded an r$^2$ (coefficient of determination) value of 0.99, thereby indicating that the functional model accurately describes a very high percentage of the observed data behavior.

The foregoing information can then be utilized to develop mathematical equations for lag correction; i.e., a transform for the time constant(s). Specifically, assuming the change between two consecutive samples to be approximately linear, any given system (in this example, pO2) with a time response of τ1 can be transformed to exhibit the time response equal to τ2 using the following equations (2)-(4):

$$pO2\_step(n) = \left(1 - e^{-\left(\frac{\Delta t}{\tau_2}\right)}\right) * pO2(n-1) \quad \text{Eqn. (2)}$$

$$pO2\_ramp(n) = \quad \text{Eqn. (3)}$$
$$\left(\Delta t - (\tau_2 - \tau_1) + \left((\tau_2 - \tau_1) * e^{-\left(\frac{\Delta t}{\tau_2}\right)}\right)\right) * \frac{(pO2(n) - pO2(n-1))}{\Delta t}$$

$$\text{Corrected\_pO2}(n) = pO2\_step\,(n) + \quad \text{Eqn. (4)}$$
$$pO2\_ramp\,(n) + \left(e^{-\left(\frac{\Delta t}{\tau_2}\right)} * \text{Corrected\_pO2}(n-1)\right)$$

Where:
Δt is the elapsed time between two samples measured by the system;
τ$_2$ is the target time constant for the system;
τ$_1$ is the observed time constant of the system;
pO2(n) is the nth measurement of the system; and
n is the current sample being processed.

Figure 10:
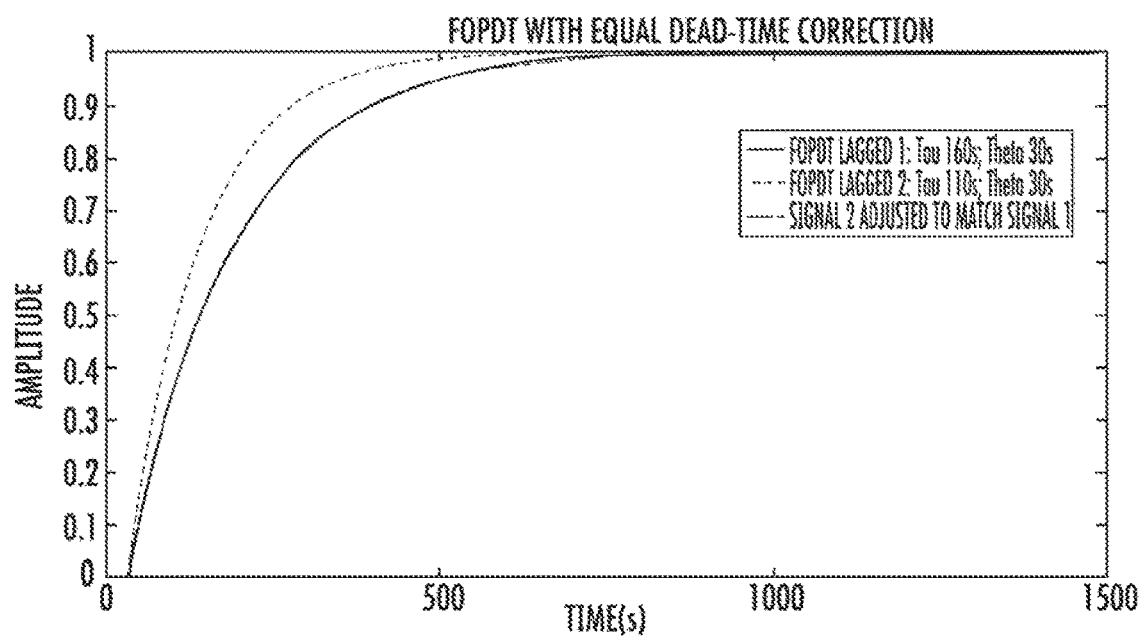
FIG. 10 is a graphical representation of two simulated test signals (in response to a step change input), wherein one signal has been mathematically transformed to match the other signal, according to one embodiment of the present disclosure.
Figure 11:
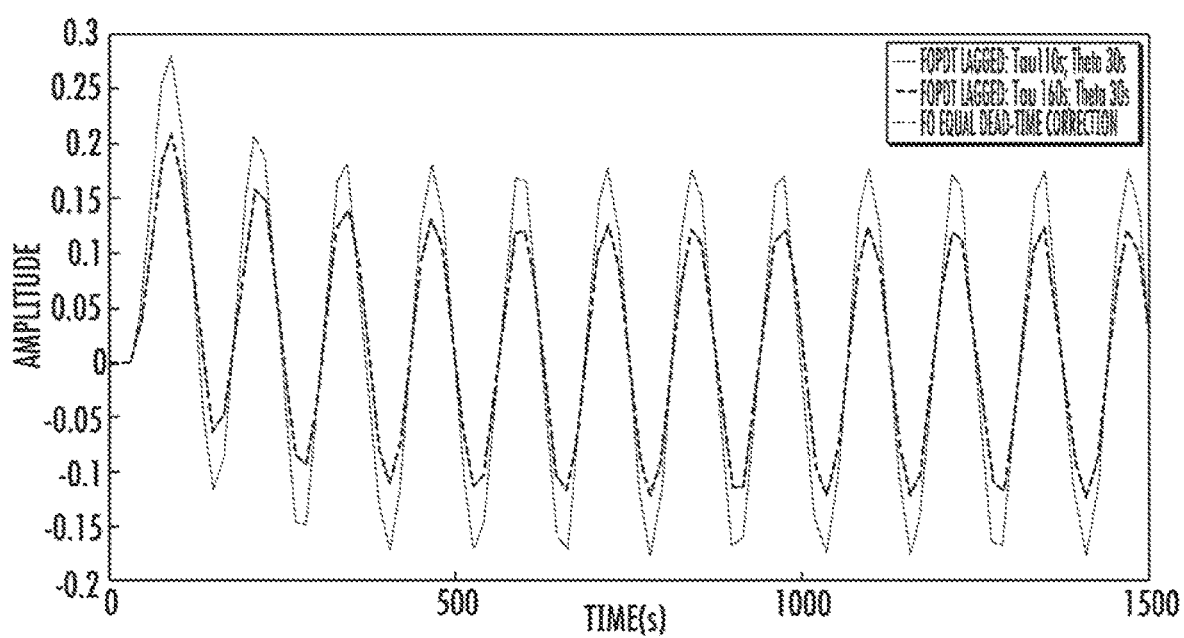
FIG. 11 is a graphical representation of two simulated test signals (in response to a sinusoid input), wherein one signal has been mathematically transformed to match the other signal, according to one embodiment of the present disclosure.

As shown in FIGS. 10 and 11 herein, the application of the above mathematical transform on a step and sinusoidal signal, respectively, correctly resulted in the desired target signal. Specifically, in FIG. 10, two simulated test systems, where time responses for the first system of τ=110 sec, θ=30 sec (τ: Time constant, θ: time delay or dead-time), and the second of τ=160 sec, θ=30 sec, were subjected to a step stimulus. The output signal from the first system was mathematically transformed to match the second, more latent signal. Similarly, in FIG. 11, the two simulated test systems (response characteristics described above) were subjected to a sinusoid stimulus. The first signal was mathematically transformed to match the second, more latent signal.

Hence, summarizing the foregoing observations:
(1) The dead-times for the exemplary O2 and Cg electrodes are reasonably well-matched assuming similar/consistent bulk layer thickness around the two electrode membrane structures.
(2) For any given bulk layer thickness, the temporal mismatch in the exemplary Model 100 sensor is substantially due to time constant mismatch.
(3) For any given bulk layer thickness: (i) the time constant of the oxygen (reference) electrode is constant over any Cg/Co; and (ii) the time constant of the glucose electrode is well-approximated by a cubic function of Cg/Co.
(4) If the time constants of the glucose electrode and its paired oxygen (reference) electrode are known, the signal from the oxygen electrode can be transformed to match the temporal response of the glucose electrode (or vice versa).

In developing the exemplary embodiment of the "mismatch correction" algorithm described herein (see e.g., the exemplary methodology of FIG. 12), the following assumptions are also made:
(1) At any given time, the equivalent bulk layer thickness around the glucose (analyte) electrode membrane is equal to that around its paired oxygen electrode(s).
(2) At any given bulk layer thickness, the time responses of the glucose electrode and the oxygen electrode are well-matched at zero glucose (Cg/Co=0). Therefore, in conjunction with assumption (1) above, the time constant difference between the oxygen and glucose electrodes at any instant is only dependent on the ratio Cg/Co (in this example).
(3) Sampling time is comparable to or smaller than the time constants of the electrodes, and a Cg estimate can be assumed to be a good approximation for periods of time (e.g., ~180 sec).

Per the above findings and assumptions, pO2 measured by the less-latent oxygen (reference) electrode (or vice versa) can be transformed to match the time response of glucose electrode, provided that (i) the time constant of the oxygen electrode, (ii) the operating level of Cg/Co, and (iii) the dependence of the time constant on Cg/Co, are known.

Based on the in vitro data and COMSOL simulations shown above, as well as four months of subsequent in vivo data obtained via human clinical trials, the time constant parameters under a typical 1.5 mil-2 mil bulk layer thickness are as shown in Table 3 as follows:

TABLE 3

| Parameter | Value |
|---|---|
| $\tau_{O2}$ | 90 s |
| B | 0.1 |

Where:

$$\tau_{Cg} = \tau_{O2} + B^{*}(\text{true } Cg/Co)^3 \qquad \text{Eqn. (5)}$$

Figure 14:
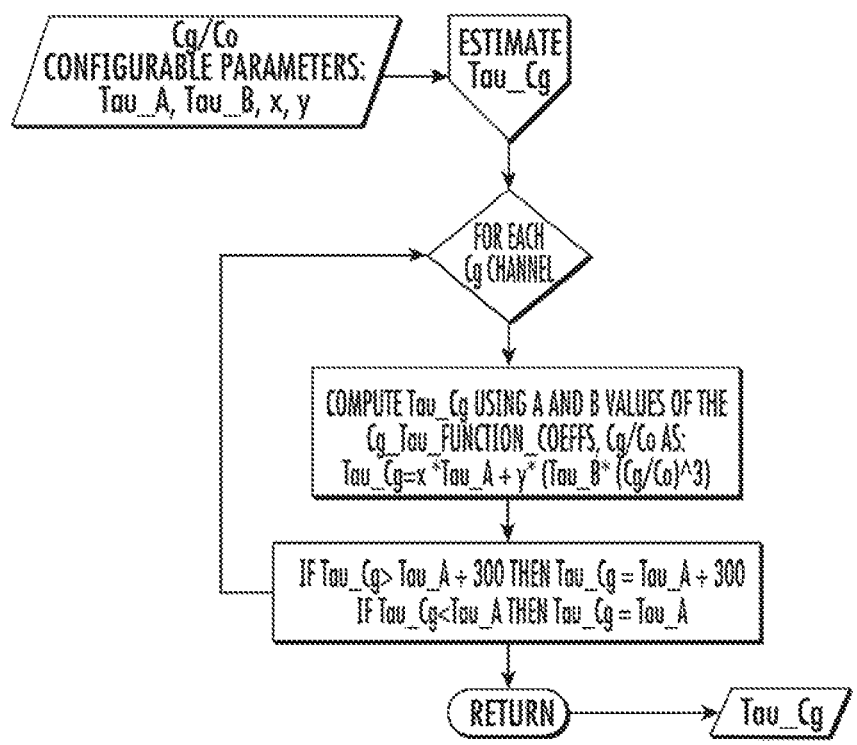
FIG. 14 is a logical flow diagram illustrating an exemplary embodiment of a process for estimating the parameter tau Cg according to the present disclosure.

FIG. 14 illustrates the exemplary embodiment of estimating $\tau_{Cg}$ (including Eqn. (5) above), where the additional configurable parameters are as specified in Table 4 below. Specifically, the configurable parameters for the Model 100 sensor are:

TABLE 4

| Parameter | Default Value | Range | Resolution |
|---|---|---|---|
| w1, w2, w3, w4, w5 | 1, 0, 0, 0, 0 | 0-1 | 0.001 |
| x | 1 | 0-1 | 0.01 |
| y | 1 | 0-1 | 0.01 |
| z | 1 | 0-1 | 0.01 |
| Tau_A | 90 | 0-300 | 1 |
| Tau_B | 0.1 | 0-0.5 | 0.01 |
| t_avg | 180 sec | 0-900 | 15 |

Figure 12:
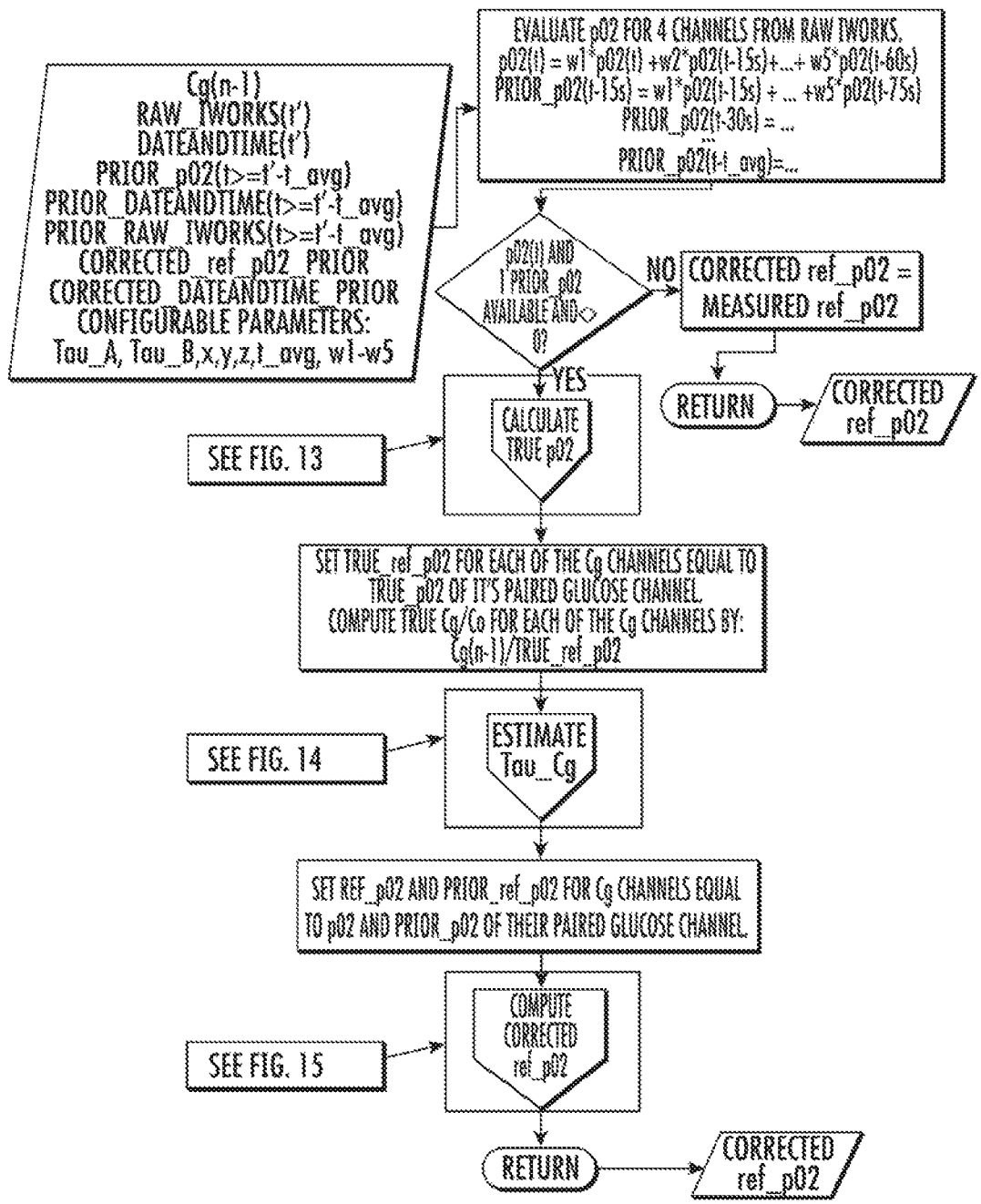
FIG. 12 is a logical flow diagram illustrating an exemplary embodiment of a process for dynamic mismatch compensation according to the present disclosure.
Figure 13:
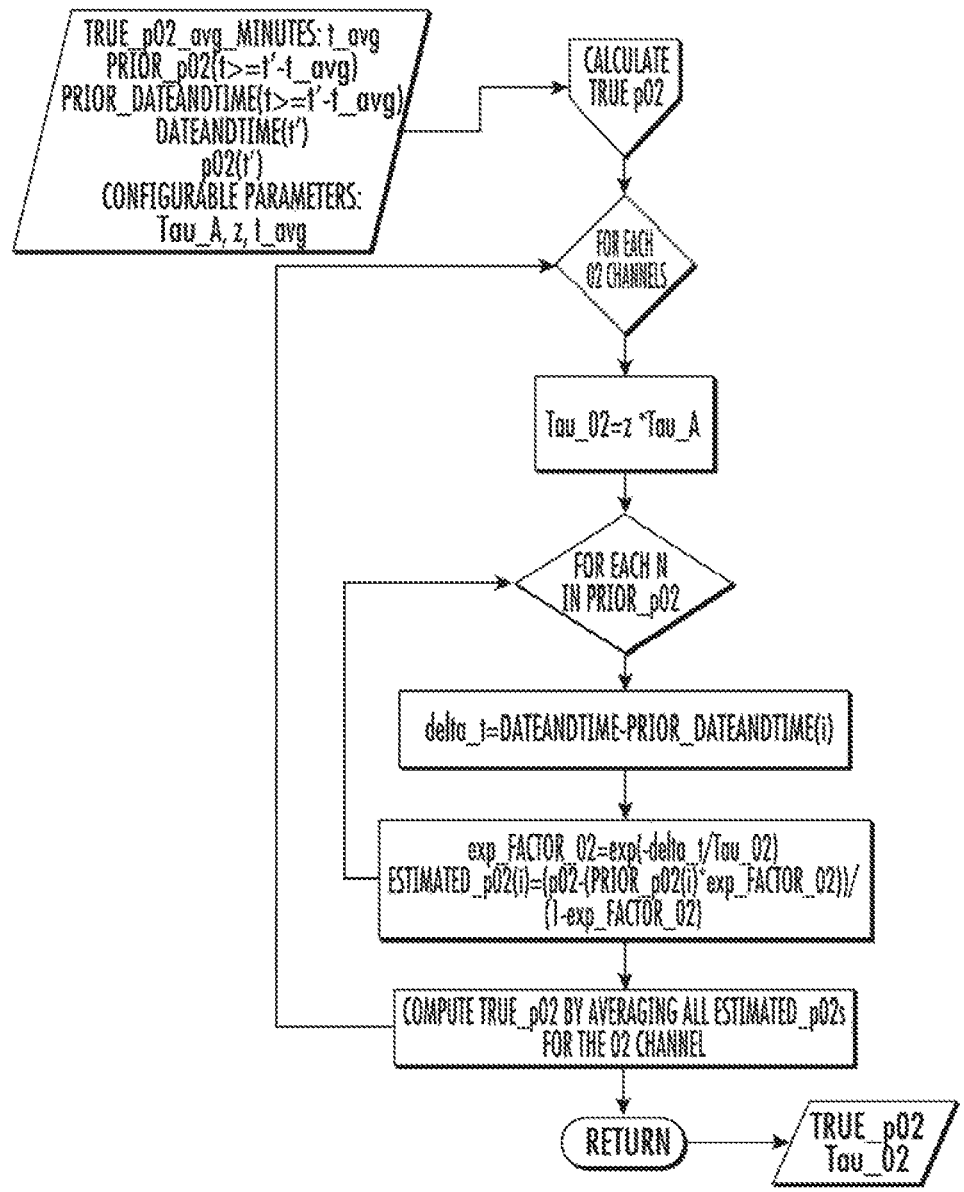
FIG. 13 is a logical flow diagram illustrating an exemplary embodiment of a process for calculating actual or "true" pO2 according to the present disclosure.

Where, t_avg is the window size used to filter/smooth the estimate of true pO2, as shown in FIGS. 12 and 13; and, w1 to w5 are weight parameters that help correct for time delay mismatch of up-to 60 sec, as shown in FIG. 12.

A sample of exemplary MATLAB code language is included in Appendix I.

Figure 15:
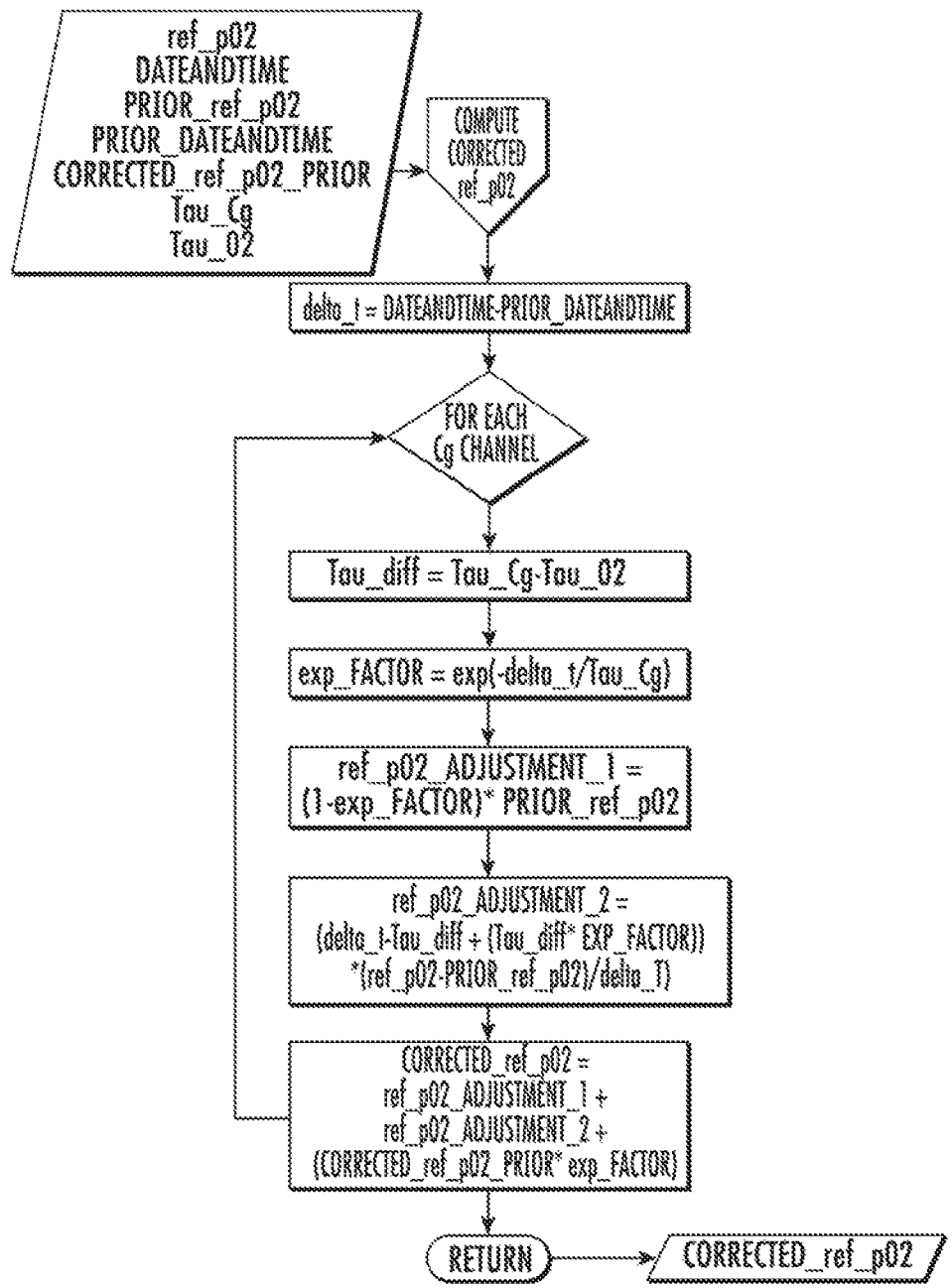
FIG. 15 is a logical flow diagram illustrating an exemplary embodiment of a process for computing corrected reference pO2 according to the present disclosure.

Therefore, per the equations and parameters presented thus far, an estimate of the actual or "true" Cg/Co at any given time advantageously allows for the calculation of $\tau_{Cg}$ (the time constant of the glucose or analyte detector element) and, therefore, enables the transformation of the measured pO2 to a corrected pO2 based on the equations presented herein (see FIG. 15).

For calculation of the true Cg/Co (see FIG. 12), the measured glucose from the last sample (if sampled within the past 180 sec, consistent with assumption (3) above) can be divided by an approximation of the true pO2. True pO2 can be approximated from the measured pO2 using Eqn. (6) provided below:

$$\text{true } pO2(n) = \frac{\left(pO2(n) - \left(pO2(n-1) * e^{-\left(\frac{\Delta t}{\tau_{O2}}\right)}\right)\right)}{1 - e^{-\left(\frac{\Delta t}{\tau_{O2}}\right)}} \qquad \text{Eqn. (6)}$$

See FIG. 13 herein, where an exemplary embodiment of a true pO2 calculation methodology is illustrated.

It will also be recognized that while described primarily in the context of the foregoing examples of temporal correction or alignment of a first sensor element to a second (e.g., a reference oxygen electrode to glucose electrode to), the various techniques and apparatus described herein may readily be adapted to correct or align two (or more) electrodes to a third temporal or other reference. For instance, in one such implementation, both the signals from the exemplary blood glucose differential sensor pair described above are transformed to a third common (target) temporal sequence (e.g., τ1=120 sec and τ2=140 sec are both transformed to τ=130 sec).

Temporal Mismatch Correction Applications

Figure 16:
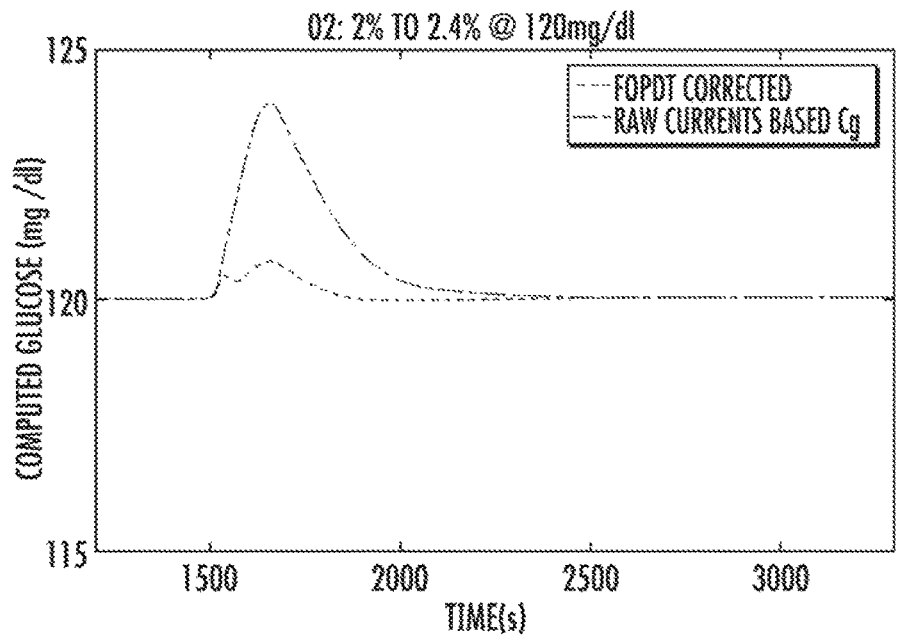
FIG. 16 is a graphical representation of a temporal mismatch correction as applied to exemplary COMSOL simulation data, according to one embodiment of the present disclosure.

The exemplary temporal mismatch correction algorithm was applied to the simulated and experimental data collected in vitro as well as in vivo. FIG. 16 shows the application of the algorithm on the data collected from a COMSOL-based step simulation. The simulation was performed at constant Cg (120 mg/dl), where pO2 was stepped up from 14.3 mmHg to 17.1 mmHg. The uncorrected signal showed an error of 4 mg/dl (3.33%) in computed glucose, whereas the corrected signal showed an error of ~0.5 mg/dl (0.4%), thereby demonstrating the enhanced accuracy of the corrected signal over the uncorrected signal.

Figure 17:
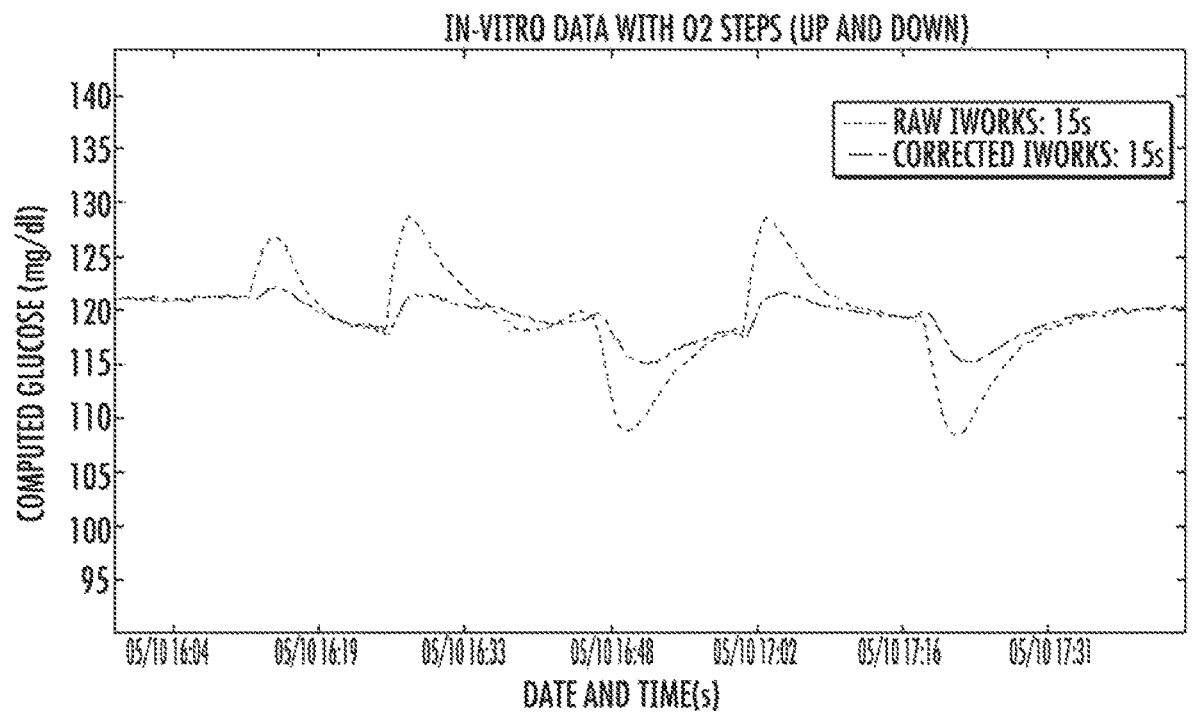
FIG. 17 is a graphical representation of a temporal mismatch correction as applied to exemplary in vitro data, according to one embodiment of the present disclosure.

The results from application of the exemplary temporal mismatch correction algorithm to in vitro data under similar operating conditions—i.e., constant Cg (120 mg/dl) and pO2 steps between 14.3 mmHg to 17.1 mmHg—are shown in FIG. 17. The in vitro results validated the observations made from COMSOL simulations, where equivalent improvements were seen for oxygen steps in both directions.

Figure 18:
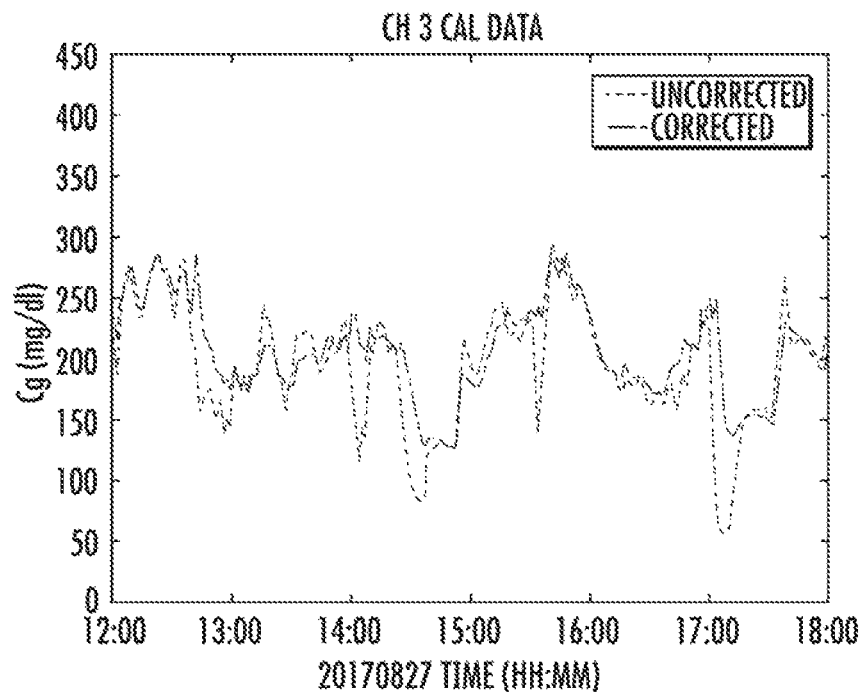
FIG. 18 is a graphical representation of a temporal mismatch correction as applied to first exemplary in vivo data, according to the present disclosure.
Figure 19:
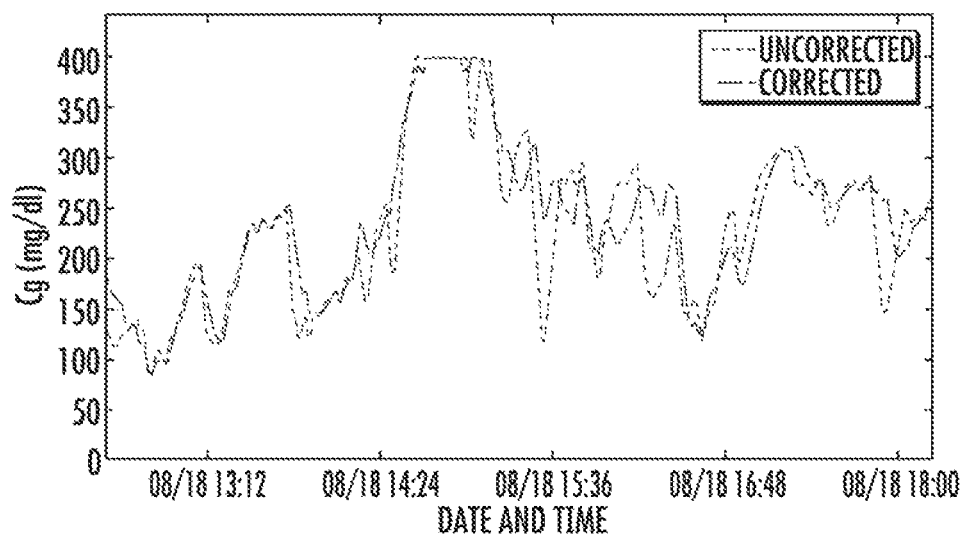
FIG. 19 is a graphical representation of a temporal mismatch correction as applied to second exemplary in vivo data, according to the present disclosure.

Once the algorithm was validated via in vitro experiments, the algorithm was tested on in vivo data (i.e., actual living subject data) received from a Frequency Augmented Sensor Transmission (FAST) trial. FIGS. 18 and 19 herein show examples of results obtained from the application of the temporal mismatch correction algorithm to the aforementioned in vivo data, illustrating reduction in spurious spikes/rapid changes (at non-physiologic rates) in the measured glucose signal. The glucose signal in human subjects is expected to contain frequencies of 8.3 mHz (T=20 min) or lower. As shown in FIG. 18, the corrected signal shows attenuation of rapid changes in the signal, where the rapid changes can be attributed to non-physiologic artifacts.

Sensor Apparatus

Figure 20:
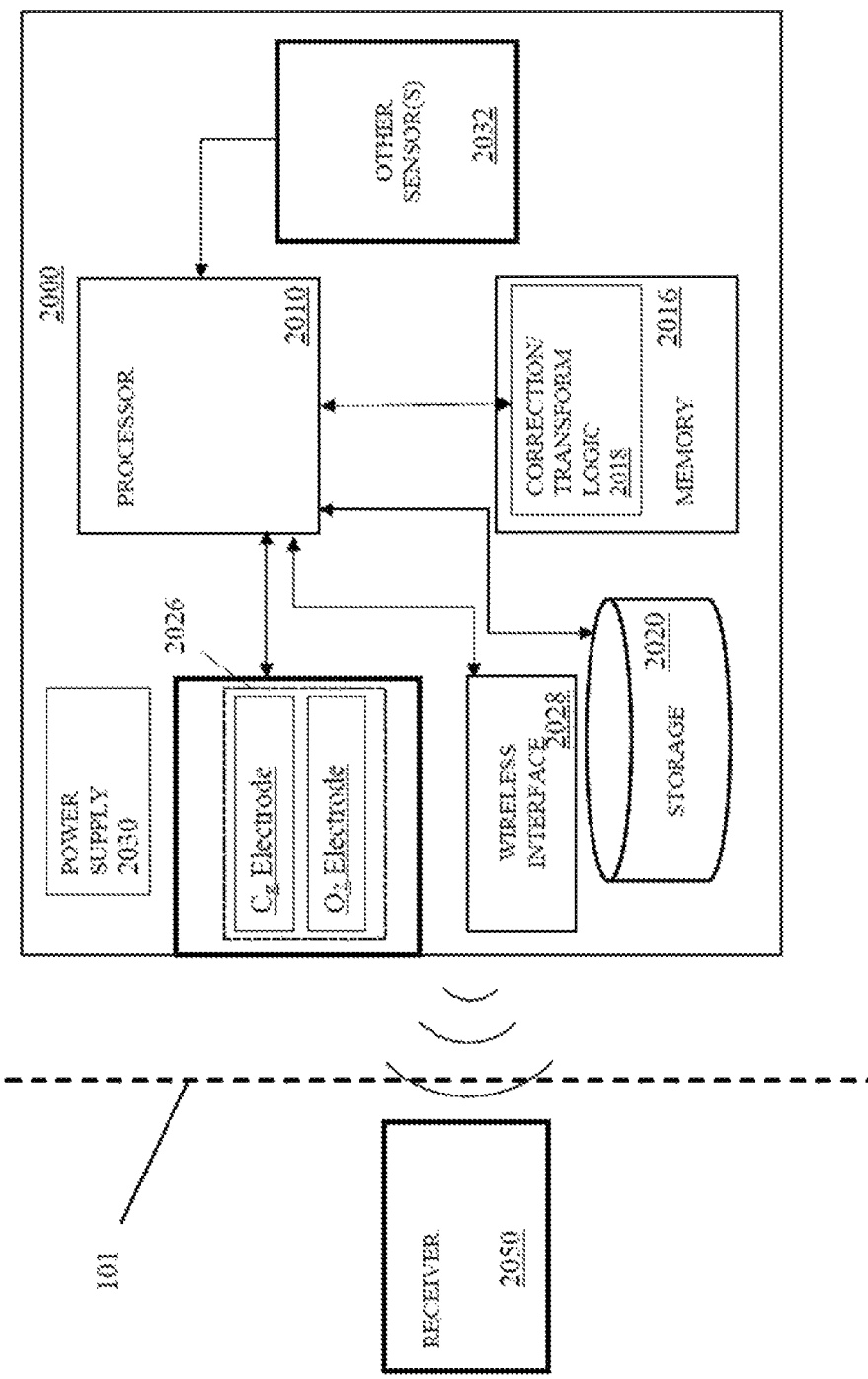
FIG. 20 is a functional block diagram illustrating an exemplary implantable sensor apparatus and receiver apparatus useful with the various aspects of the present disclosure.

FIG. 20 is a functional block diagram illustrating an exemplary implantable sensor apparatus 2000 and receiver and processor apparatus 2050 according to one embodiment of the present disclosure. As shown, the sensor apparatus 2000 includes a processor 2010 (e.g., digital RISC, CISC, and/or DSP device), and/or a microcontroller (not shown), memory 2016, software/firmware 2018 operative to execute on the processor 2010 and stored in e.g., a program memory portion of the processor 2010 (not shown), or the memory 2016, a mass storage device 2020 (e.g., NAND or NOR flash, SSD, etc. to store collected raw or preprocessed data or other data of interest), blood glucose and oxygen (reference) detector elements as part of a differential sensor element pair or a differential sensor element group 2026, a wireless interface 2028 (e.g., narrowband, PAN such as Bluetooth, or other), and a power supply 2030 (e.g., a primary Lithium or rechargeable NiMH or Lithium ion battery). Exemplary configurations of sensor and external receiver/parent devices are described in detail in co-pending U.S. patent application Ser. Nos. 15/853,574, 13/559,475, 14/982,346, 15/170,571, 15/197,104, 15/359,406, 15/368, 436, 15/472,091, and 15/645,913, each of the foregoing previously incorporated herein by reference in its entirety.

Also depicted in FIG. 20, the sensor apparatus 2000 can optionally include one or more additional internal sensors 2032. The internal sensor(s) 2032 may be any of a temperature sensor, an accelerometer, a pressure sensor, a pulse meter, a conductivity meter, pH (i.e., hydronium ion concentration), electric field sensor, and/or other (non-target) analyte-detection sensors (e.g., other blood analytes). In an alternate embodiment, the one or more internal sensors can be located in a separate implantable apparatus positioned proximate to the sensor 2000 during implantation.

As can be appreciated by those of ordinary skill given the present disclosure, any number of different hardware/software/firmware architectures and component arrangements can be utilized for the sensor apparatus 2000 of FIG. 20, the foregoing being merely illustrative. For instance, a less-capable (processing, sensing, and/or data storage-wise) or "thinner" configuration may be used (e.g., excluding the one or more additional internal sensors), or additional functionality not shown added (e.g., including additional types of other sensors and/or components).

In the illustrated embodiment, the logic 2018 is configured to execute on the processor 2010 to implement the foregoing algorithmic correction (transformation) operations on data generated by the O2 detector element(s) (part of detector pair or group 2026) and temporally "align" the signals with those of the Cg detector element and/or the signals of the internal sensors 2032, as previously described herein.

Additional Embodiments

It will be appreciated that the following additional embodiments can be used alone or in combination with the aforedescribed examples.

Correction of Delay

While the exemplary analytical framework, test data, and resulting applications described herein correct for the lag owing to a mismatch in time constants, the various principles of this disclosure can be extended to systems where the temporal mismatch is due to other factors, such as e.g., delay or a combination of (i) delay and (ii) lag mismatch (as in the exemplary transformation shown in FIG. 4B). In the case of pure delay mismatch, one signal is simply offset in time to account for the delay mismatch. For example, if signal 'y' is delayed by 15 sec in comparison to signal 'x', a delay-matched signal can be obtained as shown below in Eqn. (7):

$$\dot{x}(t)=x(t-15)=y(t) \quad \text{Eqn. (7)}$$

In the case of discrete signals, if the signal 'x' was not recorded at the precise time (t−15), then the estimate $\dot{x}(t)$ can be obtained via interpolation (linear, quadratic, etc.) from other measured (and timestamped) samples of 'x.' Furthermore, if the signals have both delay and lag mismatch, the signals can be first matched for the delay (as shown above), followed by the lag correction as shown and described in detail previously herein.

In Vivo Modeling Methods

As noted above, a salient aspect for temporal mismatch correction is the accurate estimation of the time constants and/or dead-time of the sensors (e.g., those of the exemplary Model 100 ICGM sensor, and the exemplary Model Gen 3 sensor described above). Since sensors implanted in different living subjects may be exposed to different physiological environments (i.e. subject-to-subject variability), and/or a sensor implanted in one subject may be exposed to variations in conditions over time (due to change in Body Mass Index, tissue encapsulation around the implanted sensor due to e.g., so-called foreign body response or FBR, or yet other factors), models of the time constant (Tau) and/or dead-time (delay) as a function of Cg/Co or sensor element and/or environmental characteristics may deviate from that as shown previously herein.

In one such variant, the deviation can be reflected by expressing Tau using a different functional form dependence on Cg/Co. Alternatively (or in combination), just the parameters ($\tau_{O2}$ and B) of the functional form can be changed on a sensor-by-sensor basis, and/or with respect to time. For example, in one such case, each of the sensors can be first operated in a "training mode," where the parameters and/or functional form of the time constant equation are estimated by analyzing the raw data collected in vivo. Hence, each sensor's response can be individually characterized, thereby advantageously allowing for a sensor-specific transformation function to be generated.

As one specific example of the above-described "parameter estimation" concept, consider data from a fixed time period (e.g., 6 hours), which are evaluated with different combinations of candidate function parameters ($\tau_{O2}$ and B) to determine a combination of parameters that minimizes a pre-defined error cost function (e.g., power in high frequency of the differential signal at frequencies higher than 0.002 Hz).

Alternatively, candidate functions can be chosen in addition to the candidate parameters for the minimization problem. This training mode can be executed at pre-defined fixed time intervals (e.g., daily, weekly, etc.), or as determined by the system, such as being event-driven (e.g., when large errors are observed in the computed glucose, etc.), as well as when instigated by the user, and/or a medical practitioner.

Figure 21A:
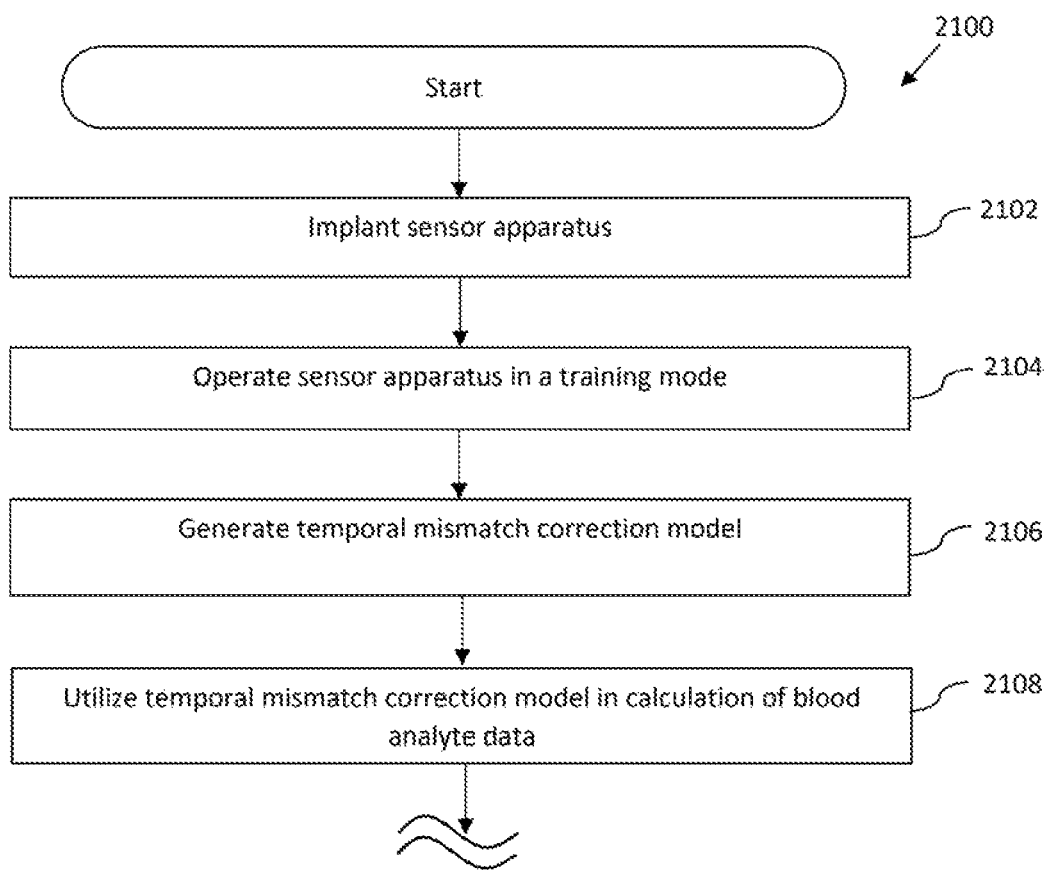
FIG. 21A is a logical flow diagram representing an exemplary method of temporal mismatch correction, according to another embodiment of the present disclosure.

Turning now to FIG. 21A, an exemplary generalized method 2100 for in vivo characterization and temporal mismatch correction between associated sensing element/detector signals is shown and described. First, at step 2102, a sensor apparatus (having two or more detector elements) is implanted in a subject. After implantation, the sensor apparatus is operated in a training mode where in vivo signals and/or data are collected from the detector elements over a period of time, per step 2104. A temporal mismatch correction algorithm is generated based at least in part on the data collected in the training mode operation (step 2106), and the generated temporal mismatch correction model is utilized for determination of blood analyte data (and/or data related to other physiological parameters), at step 2108.

Figure 21B:
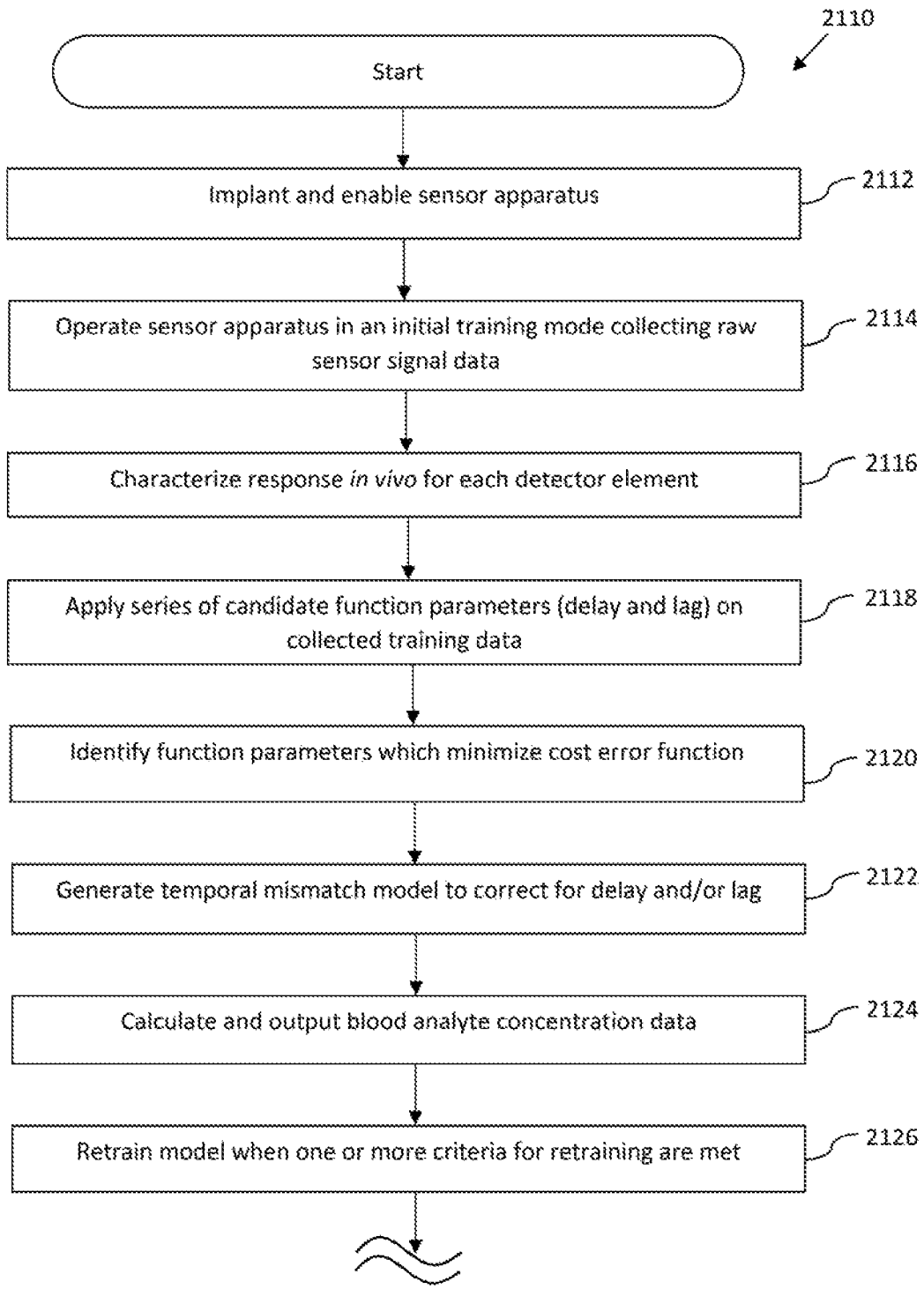
FIG. 21B is a logical flow diagram illustrating one particular implementation of the method of FIG. 21A.

Referring now to FIG. 21B, one specific implementation of the generalized method 2100 of FIG. 21A is shown. First, at step 2112 of method 2110, a multi-detector sensor apparatus (such as those discussed supra) is implanted in a subject, such as via the implantation methods described in co-owned U.S. patent application Ser. No. 14/982,346, previously incorporated herein. The implanted sensor apparatus (or an associated processing apparatus) comprises logic including a pre-stored temporal mismatch correction model and initial model parameters (e.g., Tau, dead-time, $\tau_{O2}$ and B, etc.). Per step 2114, after implantation, the sensor apparatus is operated in a "temporal mismatch training mode," where signal data from each detector (e.g., analyte-modulated, background, non-analyte detectors) is collected and stored for subsequent evaluation. It will be appreciated that the sensor apparatus is operated in the training mode until a statistically significant amount of data is collected.

Per step 2116, response characteristics are determined for each detector, and a series of candidate function parameters to correct for delay and/or lag are applied to the training data (step 2118) in order to identify a combination of parameters that minimizes the aforementioned pre-defined error cost function (step 2120). Based on the foregoing analysis of the training data, a context and/or user-specific temporal mismatch model is generated (i.e., the pre-stored model is adjusted based on the analysis) (step 2122). Subsequently, per step 2124, the context and/or user-specific temporal mismatch model is is utilized to transform or match associated raw detector signals/data for use in sensor apparatus calculations, such as calculation of a blood analyte level and/or an (ROC) of blood analyte. As discussed supra, the model can be re-trained (as necessary based on e.g., specified time intervals, detection of an event, or user and/or medical provider selection) via subsequent temporal mismatch training mode operation of the implanted sensor (step 2126).

It will also be appreciated that the foregoing analysis can be performed indigenously or substantially autonomously (i.e., within the sensor element and its onboard logic itself), and/or "off-board," such as via processing power and algorithms operative to run on an external receiver, parent platform (e.g., user smartphone), and/or cloud server apparatus in data communication with the (implanted) sensor.

For example, use of a cloud-based approach advantageously allows data from multiple different sensors (and presumably from multiple different individuals with varying physiologies) to be evaluated as part of, e.g., the above-described parameter estimation process. For instance, certain types of sensor response data may lend themselves to certain types/combinations of candidate functions and/or parameter values, and hence a newly implanted or "trained" device can benefit from the prior analytics conducted with respect to prior patients/sensors, as well as the higher off-board processing power and data storage capability (and connectivity) of a cloud-based system.

Additional or Alternative Sensor Elements

As discussed elsewhere herein, it will be additionally appreciated that the techniques and apparatus described herein can be utilized with other types of blood glucose or other analyte sensors, including those utilizing a peroxide-based operational model. For example, if a peroxide-based sensor is sensitive to another process/parameter (e.g., the presence of acetaminophen or other compounds in the subject's blood or tissue, local temperature, etc.), another sensor can be utilized "differentially' that predicts and/or measures the specific parameter (e.g., acetaminophen, temperature, etc.) either directly or indirectly (such as via measurement of a resulting substance from the other process) in the body. The measurements or predictions from this differential (e.g., acetaminophen, temperature, etc.) sensor may be temporally adjusted before application to the peroxide-based measurements.

In one example, sensor response to temperature can be characterized by including a known external reference system in the in vitro testing environment. As discussed supra, a commercial-off-the-shelf (COTS) temperature probe of known transient specification can be included to measure the true temperature during in vitro characterization. In this example, delay and a lag of signals of the on-board temperature sensor and peroxide-based electrode (in response to the temperature step) are characterized via comparison to the signals of the COTS temperature sensor. The delay and lag of the on-board temperature sensor and peroxide-based sensing electrode are utilized to generate a model for correcting temporal mismatch (delay and/or lag) between the temperature and peroxide-based sensing elements. This model may then be utilized in vivo to temporally match temperature measurements before application to the peroxide-based measurements.

It will be recognized that while certain embodiments of the present disclosure are described in terms of a specific sequence of steps of a method, these descriptions are only illustrative of the broader methods described herein, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure and claimed herein.

While the above detailed description has shown, described, and pointed out novel features as applied to various embodiments, it will be understood that various omissions, substitutions, and changes in the form and details of the device or process illustrated may be made by those skilled in the art without departing from principles described herein. The foregoing description is of the best mode presently contemplated. This description is in no way meant to be limiting, but rather should be taken as illustrative of the general principles described herein.

APPENDIX I

Exemplary Computer Code for Transforming Signal with
Time-Varying Time Constant
© 2017-2018 GlySens, Inc. All rights reserved

```
Sample Code for (Tau_timeConstant) to a fixed and known time constant
(timeConstant_O2electrode):
Iworks_channels = size(sensorO2Iworks,2);
O2_Iworks(1,:) = sensorO2Iworks(1,:);
numIterations = size(sensorO2Iworks,1);
TauDiff = Tau_timeConstant − timeConstant_O2electrode;
for i = 1: numIterations
    if(Tau_timeConstant(i,:) == 0)
        O2_Iworks(i,:) = measured_pO2(i,:);
        continue
    end
    j = find(sensorO2Iworks(1:i−1) ~= 0, 1, 'last');
    samplesTimeDiff = DateAndTime(i) − DateAndTime(j);
    secondsInDay = 24*3600;
    timeElapsedBetweenSamples =
samplesTimeDiff*secondsInDay;
    exponentialCoeff = (−
timeElapsedBetweenSamples./Tau_timeConstant(i,:));
    deltaIworks = (1 − (1.*exp(exponentialCoeff))) .*
(sensorO2Iworks(j,:));
    deltaIworks2 =
(repmat(timeElapsedBetweenSamples,1,Iworks_channels) −
TauDiff(i,:) + (TauDiff(i,:) .* exp(exponentialCoeff))) .*
...
                                ((sensorO2Iworks(i,:) −
sensorO2Iworks(j,:))./timeElapsedBetweenSamples);
    O2_Iworks(i,:) = deltaIworks + deltaIworks2 +
(O2_Iworks(j,:) .* (1.*exp(exponentialCoeff)));
end
```

What is claimed is:

1. A method of operating a computerized apparatus for use with an analyte sensor, the method for determination of a concentration of a physiologic analyte, the method comprising:
   determining data indicative of a response of a first detector of the analyte sensor;
   determining data indicative of a response of a second detector of the analyte sensor, the first and second detectors configured to, when used in conjunction, enable output of data representative of the concentration of the physiologic analyte relative to a concentration of a background physiologic analyte, the response of the second detector having at least one temporal response characteristic different than that of the response of the first detector;
   applying a mathematical transformation algorithm to the determined data indicative of the response of the second detector to generate data indicative of a transformed response, the mathematical transformation algorithm dynamically determined based at least in part on a ratio of first intrinsic data relating to the physiologic analyte, to second intrinsic data relating to the background physiologic analyte, the transformed response having at least one temporal response characteristic that substantially matches that of the response of the first detector; and
   utilizing (i) the determined data indicative of the response of the first detector and (ii) the generated data indicative of the transformed response, to determine the concentration of the physiologic analyte.

2. The method of claim 1, wherein (i) the physiologic analyte comprises blood glucose, (ii) the analyte sensor comprises an oxygen-based blood glucose sensor, (iii) the first detector comprises a glucose-modulated sensing element, (iv) the second detector comprises an oxygen sensing element, and (v) the background physiologic analyte comprises oxygen.

3. The method of claim 1, wherein the applying of the mathematical transformation algorithm to the determined data indicative of the response of the second detector to generate the data indicative of the transformed response at least in part comprises applying the mathematical transformation to correct for a lag value between the data indicative of the response of the first detector and the data indicative of the response of the second detector, the lag value indicative of a slower response characteristic in the presence of the physiologic analyte for analyte-modulated detection relative to background species detection within the analyte sensor.

4. The method of claim 1, wherein the applying of the mathematical transformation algorithm to the determined data indicative of the response of the second detector to generate the data indicative of the transformed response at least in part comprises applying the mathematical transformation to correct for a delay value between the data indicative of the response of the first detector and the data indicative of the response of the second detector, the delay value indicative of a faster response characteristic due to a greater background species diffusion rate for background species detection relative to analyte-modulated detection within the analyte sensor.

5. The method of claim 1, further comprising determining a function for use in the mathematical transformation algorithm via use of an in vitro test environment, the determining comprising:
   collecting response data from the analyte sensor while in vitro, the collecting of the response data comprising collecting at least:
      data relating to an in vitro baseline response for the first detector;
      data relating to an in vitro baseline response for the second detector;
      data relating to an in vitro step-up response in an increased analyte condition for the first detector; and
      data relating to an in vitro step-up response in the increased analyte condition for the second detector;
   calculating one or more correction values from the collected response data; and
   generating the mathematical transformation algorithm based at least in part on the one or more correction values.

6. The method of claim 5, wherein the first detector comprises an analyte-modulated detector having a first membrane structure associated therewith, and the second detector element comprises a background species detector having a second membrane structure associated therewith; and
   the collecting of the in vitro response data further comprises collecting (i) data relating to an in vitro baseline for a third detector, and (ii) data relating to an in vitro step-up response in the increased analyte condition for the third detector, the third detector comprising no membrane structure.

7. The method of claim 6, wherein the calculating one or more correction values from the collected response data comprises calculating one or more of a lag value or a delay value for each of the first detector element and the second detector element relative to the third detector element.

8. The method of claim 1, further comprising determining the mathematical transformation algorithm via an in vivo environment, the determining comprising:

collecting response data during a training mode operation of the analyte sensor while in vivo, the collecting of the response data comprising collecting at least:

data relating to a first series of in vivo responses for the first analyte detector over a prescribed period of time; and data relating to a second series of in vivo responses for the second analyte detector over the prescribed period of time;

evaluating the data relating to the first series of in vivo responses and the data relating to the second series of in vivo responses with at least a plurality of candidate parameter values;

identifying one or more of the plurality of candidate parameter values, the one or more candidate parameter values identified from the plurality of candidate parameter values and resulting in a minimum value of a pre-defined error cost function; and generating the mathematical transformation algorithm based at least in part on the identified one or more of the plurality of candidate parameter values.

9. The method of claim 8, wherein the evaluating the data relating to the first series of in vivo responses and the data relating to the second series of in vivo responses with the plurality of candidate parameter values at least in part comprises evaluating the data relating to first series of in vivo responses and the data relating to the second series of in vivo responses with each of a plurality of candidate time constant values and each of a plurality of candidate delay values; and the identifying one or more of the plurality of candidate parameter values comprises identifying at least one of the plurality of candidate time constant values and at least one of the plurality of candidate delay values which each minimize the pre-defined error cost function.

10. The method of claim 8, wherein the determining the mathematical transformation algorithm via the in vivo environment further comprises:

based at least in part on meeting one or more re-evaluation criteria, re-evaluating the identified one or more of the plurality of candidate parameter values which minimizes the pre-defined error cost function; and generating an updated mathematical transformation function based at least in part on the re-evaluating.

11. The method of claim 1, wherein:

the determining the data indicative of the response of the first detector of the analyte sensor comprises receiving first raw sensor signals from the first detector, and processing the first raw sensor signals to generate the data indicative of the response of the first detector element; and the determining the data indicative of the response of the second detector of the analyte sensor comprises receiving second raw sensor signals from the second detector, and processing the second raw sensor signals to generate the data indicative of the response of the second detector element.

12. The method of claim 1, wherein the dynamic determination of the mathematical transformation algorithm based at least in part on a ratio of first intrinsic data relating to the physiologic analyte, to second intrinsic data relating to the background physiologic analyte, further comprises dynamic determination of at least one time constant parameter (B).

13. A computerized analyte sensor apparatus configured to determine a concentration of a physiologic analyte, the computerized analyte sensor apparatus comprising:

a first detector;

a second detector;

signal processing logic in communication with the first detector and the second detector, the signal processing logic configured to:

determine first data indicative of a response of the first detector, the response of the first detector having at least a first temporal response characteristic;

determine second data indicative of a response of a second detector, the response of the second detector having at least a second temporal response characteristic, the second temporal response characteristic being different in at least one respect than the first temporal response characteristic;

determine a mathematical transformation algorithm, the determination based at least in part on a ratio of first intrinsic data relating to a physiologic analyte, to second intrinsic data relating to a background physiologic analyte;

apply the mathematical transformation algorithm to at least the second determined data to generate third data indicative of a transformed response, the transformed response having at least one temporal response characteristic corresponding at least in part to the first temporal response characteristic; and utilize (i) the first determined data indicative of the response of the first detector and (ii) the generated third data, to determine a concentration of the physiologic analyte.

14. The computerized analyte sensor apparatus of claim 13, wherein a) the physiologic analyte comprises blood glucose, b) the computerized analyte sensor apparatus comprises an implantable oxygen-based blood glucose monitoring device, c) the first detector comprises a glucose-modulated sensing element, d) the second detector comprises an oxygen sensing element, and e) the background physiologic analyte comprises oxygen.

15. The computerized analyte sensor apparatus of claim 13, wherein the application of the mathematical transformation algorithm to the second determined data comprises applying the mathematical transformation to correct for a lag value between the first determined data and the second determined data, the lag value relating to a slower response characteristic in the presence of the physiologic analyte for analyte-modulated detection relative to background species detection within the computerized analyte sensor apparatus.

16. The computerized analyte sensor apparatus of claim 13, wherein the application of the mathematical transformation algorithm to the second determined data at least in part comprises application of the mathematical transformation to correct for a delay value between the first determined data and the second determined data, the delay value relating to a background species diffusion rate for background species detection relative to analyte-modulated detection within the computerized analyte sensor apparatus.

17. The computerized analyte sensor apparatus of claim 13, wherein the mathematical transformation algorithm comprises an algorithm determined at least in part via use of an in vitro test environment, the determination at least in part comprising:

collection of response data from the computerized analyte sensor apparatus while in vitro, the collection of the response data comprising collection of at least:

data relating to an in vitro baseline response for the first detector;

data relating to an in vitro baseline response for the second detector;

data relating to an in vitro step-up response in an increased analyte condition for the first detector; and data relating to an in vitro step-up response in the increased analyte condition for the second detector; and determination of one or more correction values from the collected response data.

18. The computerized analyte sensor apparatus of claim 13, wherein the first detector comprises an enzymatic analyte-modulated detector having a first membrane structure associated therewith, and the second detector element comprises a non-enzymatic background species detector having a second membrane structure associated therewith.

19. The computerized analyte sensor apparatus of claim 13, wherein:

the determination of the first data comprises receipt of first raw sensor signals from the first detector, and processing of the first raw sensor signals to generate the first data; and the determination of the second data comprises receipt of second raw sensor signals from the second detector, and processing of the second raw sensor signals to generate the second data.

20. The computerized analyte sensor apparatus of claim 13, wherein the determination of the mathematical transformation algorithm based at least in part on a ratio of first intrinsic data relating to the physiologic analyte, to second intrinsic data relating to the background physiologic analyte, further comprises determination of at least one time constant parameter.

21. A non-transitory computer readable apparatus comprising a storage medium, the storage medium having at least one computer program disposed thereon, the at least one computer program configured to, when executed on digital processing apparatus, determine a concentration of blood glucose by at least:

determination of first data indicative of a response of at least one glucose-modulated oxygen detector, the response of the at least one glucose-modulated oxygen detector having at least a first temporal response characteristic;

determination of second data indicative of a response of at least one background oxygen detector, the response of the at least one background oxygen detector having at least a second temporal response characteristic which is different in at least one respect from the first temporal response characteristic;

determination of a mathematical transformation algorithm, the determination based at least in part on a ratio of at least one blood glucose concentration to at least one background oxygen concentration;

application of the mathematical transformation algorithm to at least the second determined data to generate third data indicative of a transformed response, the transformed response having at least one temporal response characteristic corresponding at least in part to the first temporal response characteristic; and utilization of (i) the first determined data indicative of the response of the first detector and (ii) the generated third data to determine a corrected blood glucose concentration.

22. The non-transitory computer readable apparatus of claim 21, wherein:

the digital processing apparatus is disposed on an implantable blood glucose sensor; and at least the determination of the mathematic transformation algorithm is performed while the implanted blood glucose sensor is disposed in vivo within a living subject.

* * * * *